(12) United States Patent
Masliah et al.

(10) Patent No.: US 10,947,302 B2
(45) Date of Patent: Mar. 16, 2021

(54) COMPOSITIONS TARGETING 3-REPEAT TAU FOR THE TREATMENT OF NEURODEGENERATIVE DISORDERS, AND METHODS FOR MAKING AND USING THEM

(71) Applicant: The Regents of the University of California, Oakland, CA (US)

(72) Inventors: Eliezer Masliah, La Jolla, CA (US); Brian Spencer, La Jolla, CA (US); Edward Rockenstein, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 32 days.

(21) Appl. No.: 16/347,114

(22) PCT Filed: Nov. 3, 2017

(86) PCT No.: PCT/US2017/059928
§ 371 (c)(1),
(2) Date: May 2, 2019

(87) PCT Pub. No.: WO2018/085653
PCT Pub. Date: May 11, 2018

(65) Prior Publication Data
US 2020/0181245 A1 Jun. 11, 2020

Related U.S. Application Data

(60) Provisional application No. 62/417,535, filed on Nov. 4, 2016.

(51) Int. Cl.
*C07K 16/18* (2006.01)
*A61P 25/00* (2006.01)
(Continued)

(52) U.S. Cl.
CPC ............ *C07K 16/18* (2013.01); *A61K 9/0019* (2013.01); *A61K 9/1075* (2013.01); *A61K 9/127* (2013.01);
(Continued)

(58) Field of Classification Search
None
See application file for complete search history.

(56) References Cited

U.S. PATENT DOCUMENTS

2014/0294724 A1  10/2014  Chain
2015/0038409 A1   2/2015  Tezapsidis et al.

OTHER PUBLICATIONS

De Silva et al., "Pathological inclusion bodies in tauopathies contain distinct complements of tau with three or four microtubule-binding repeat domains as demonstrated by new specific monoclonal antibodies" Neuropathology and Applied Neurobiology, 2003, v 29, p. 388-302.

(Continued)

*Primary Examiner* — Aurora M Fontainhas
(74) *Attorney, Agent, or Firm* — Greer, Burns & Crain, Ltd.; Gregory P. Einhorn

(57) ABSTRACT

In alternative embodiments, provided are compositions such as antibodies, e.g., single chain antibodies, that target 3-repeat (3R) Tau for the treatment of neurodegenerative disorders and taupathies such as Alzheimer's Disease (AD), Pick's Disease (PiD) and Fronto-temporal lobar degeneration (FTLD), or any disorder or condition associated with a 3R Tau accumulation, and methods for making and using them. In alternative embodiments, provided are brain-penetrating antibodies that specifically recognize 3R Tau, and methods of using them to treat, ameliorate, prevent or decrease the symptoms of neurodegenerative disorders including taupathies such as Alzheimer's Disease (AD), Pick's Disease (PiD) and Fronto-temporal lobar degeneration (FTLD), or any disorder or condition associated with a (Continued)

3R Tau accumulation. Provided are methods for diagnosing a neurodegenerative disorder or a taupathy or any disorder or condition associated with a 3R Tau accumulation, and optionally the taupathy is Alzheimer's Disease, Pick's Disease or Fronto-temporal lobar degeneration.

18 Claims, 31 Drawing Sheets

Specification includes a Sequence Listing.

(51) Int. Cl.
    *A61K 9/127*    (2006.01)
    *G01N 33/68*    (2006.01)
    *A61P 25/28*    (2006.01)
    *A61K 9/00*     (2006.01)
    *A61K 9/107*    (2006.01)
    *A61K 9/51*     (2006.01)
    *A61K 39/00*    (2006.01)

(52) U.S. Cl.
    CPC ................ *A61K 9/51* (2013.01); *A61P 25/28* (2018.01); *A61K 2039/505* (2013.01); *C07K 2317/21* (2013.01); *C07K 2317/24* (2013.01); *C07K 2317/565* (2013.01); *C07K 2317/622* (2013.01)

(56) References Cited

OTHER PUBLICATIONS

Young, Written Opinion for PCT/US2017/059928, dated Mar. 2, 2018.
Young, International Search Report for PCT/US2017/059928, dated Mar. 13, 2018.

FIG. 4

```
ATGCCCATGGGGTCTCTGCAACCGCTGGCCACCTTGTACCTGCTGGGGATGCTGGTCGCTTCCTGCCT
CGGAGGCATGGAGCAGGTCAACTTAAGGGAGTCTGGGGCCGAGGTGAAGAAGCCTGGGGCCTCAG
TAAAGGTCTCCTGCAAGGTTTCTGGATACACCTTCACCGGCTACTATATGCACTGGGTGCGACAGGCC
CCTGGACAAGGACTTGAGTGGATGGGATGGATCAACTCTAACAGTGGTGCCACAAAGTATGCACAGA
AGTTTCAGGGCAGGGTCACCATGACCAGGGACACGTCCATCACCACAGCCTACATGGAGTTGAGCAG
CCTGAGATCTGACGACACGGCCGTGTATTACTGTGCGAGAGGTGCGAGAGATGGCTACGGATTTGAC
TACTGGGGCCAGGGAACCCTGGTCACCGTCTTGGCCGGTGGCGGTGGCAGCGGCGGTGGTGGGTCC
GGTGGCGGCGGATCTGGCGCGCCATCCTATGTGCTGACTCAGCCACCCTCAGCGTCTGGGACCCCG
GGCAGAGGGTCACCATCTCTTGTTCTGGAGGCAGCTCCAACATCGGAAGTAATGCTGTAAGCTGGTA
CCAGCAGCTCCCAGGAACGGCCCCCAAACTCCTCATCTTTACTAATGATCAGCGGCCCTCAGGGGTCC
CTGACCGATTCTCTGGCTCCAAGTCTGGCACCTCAGCCCCCCTGGCCATCAGTGGGCTCCAGTCAGAG
GATGAGTCTGATTATTACTGTGCAACATGGGATGACAGCCTGAATGGTTGGGTGTTCGGCGGAGGGA
CCAAGGTCACCGTCGGGCCCTTCGAAGGTAAGCCTATCCCTAACCCTCTCCTCGGTCTCGATTCTACGC
GTACCGGTGTTGACTCATCTGTCATTGATGCACTGCAGTACAAATTAGAGGGCACCACAAGATTGACA
AGAAAAAGGGGATTGAAGTTAGCCACAGCTCTGTCTCTGAGCAACAAATTTGTGGAGGGTAGT
```

Water maze test

COMPOSITIONS TARGETING 3-REPEAT TAU FOR THE TREATMENT OF NEURODEGENERATIVE DISORDERS, AND METHODS FOR MAKING AND USING THEM

This U.S. National Phase Patent Application claims priority under 35 U.S.C. § 371 to Patent Convention Treaty (PCT) International Application PCT/US2017/059928, filed Nov. 3, 2017, now pending, which claims the benefit of priority under 35 U.S.C. § 119(e) to U.S. Provisional Application Ser. No. 62/417,535, now expired, filed Nov. 4, 2016. The aforementioned applications are expressly incorporated herein by reference in their entirety and for all purposes.

GOVERNMENT RIGHTS

This invention was made with government support under grants AG5131, AG018440, AG051839, awarded by the National Institutes of Health (NIH). The government has certain rights in the invention.

TECHNICAL FIELD

This invention generally relates to medicine, neurodegenerative disorders and immunotherapy. In alternative embodiments, provided are antibodies, and compositions comprising antibodies, e.g., single chain antibodies, that target or specifically bind to 3-repeat (3R) Tau for the treatment of neurodegenerative disorders and conditions, including taupathies such as Alzheimer's Disease (AD), Pick's Disease (PiD) and Fronto-temporal lobar degeneration (FTLD), or any disorder or condition associated with a 3R Tau accumulation, and methods for making and using them. In alternative embodiments, provided are brain-penetrating, single chain antibodies that specifically recognize 3R Tau, and methods of using them to treat, ameliorate, prevent or decrease the symptoms of a neurodegenerative disorder or condition, including taupathies such as Alzheimer's Disease (AD), Pick's Disease (PiD) and Fronto-temporal lobar degeneration (FTLD), or any disorder or condition associated with a 3R Tau accumulation. Also provided are antibodies, methods and kits for the diagnosis of a taupathy, including Alzheimer's Disease (AD), Pick's Disease (PiD) and Fronto-temporal lobar degeneration (FTLD), comprising use of antibodies, e.g., single chain antibodies, that target or specifically bind to 3-repeat (3R) Tau.

BACKGROUND

Neurodegenerative disorders with Tau accumulation are a common cause of dementia in the aging population. Alzheimer's Disease (AD), Pick's Disease (PiD) and Fronto-temporal lobar degeneration (FTLD) are examples of neurodegenerative disorders with Tau accumulation and are also jointly referred as "taupathies". Alzheimer's disease is the most common form of dementia and involves the accumulation of Aβ and Tau. There are currently more than 5 million AD patients in the United States and over 35 million patients worldwide. This number is expected to double every 20 years due to the increased aging population. AD is the 6th leading cause of death in this country and the only cause of death among the top ten in the United States that cannot be prevented, cured or even slowed. Based on mortality data from 2000-2008, death rates have declined for most major diseases while deaths from AD have risen 66% during the same period {Alzheimer's Association, 2013 #865}.

Alzheimer's disease is caused by the progressive accumulation of Aβ into oligomers and plaques leading to synaptic loss, neuronal dysfunction and death. In addition, intra-neuronal Tau aggregates form characteristic neurofibrillary tangles that contribute to neuronal death {Terry, 1994 #333}. Tau (tubulin-associated unit) is a major neuronal cytoskeletal protein found in the CNS encoded by the gene MAPT {del, 2005 #1080}. Alternative splicing can generate two different major forms of Tau containing either three or four (3 or 4) 32 amino acid repeats, or 3R or 4R Tau species, respectively (Andreadis, 1992 #1081) (FIG. 1). These 3R or 4R Tau species (FIG. 1) are differentially expressed in neurodegenerative diseases with Corticobasal degeneration (CBD) and Progressive supranuclear palsy (PSP) primarily expressing the 4R Tau isoform while PiD primarily expresses the 3R Tau isoform (FIG. 1). Interestingly, both 3R and 4R Tau isoforms can be found accumulating in Alzheimer's disease and Fronto-temporal Dementia (FTDP-17T) {Dickson, 2011 #1082} (FIG. 1). Pick's disease is a less common cause of dementia and is characterized by cortical atrophy associated with neuronal loss, gliosis and formation of Tau-positive, globular, intra-neuronal inclusions in the neocortex and limbic system denominated Pick bodies (PB's). The clinical presentation with behavioral variant fronto-temporal dementia (bvFTD) is seen in PiD with fronto-temporal degeneration [8] while fronto-parietal atrophy presents with apraxia [9]. Mutations in the Tau gene microtubule associated protein Tau (MAPT) account for the majority of familial PiD cases [10,11,12]

Tau protein can also occur as numerous post-translational species in the CNS. These include: phosphorylation, O-glycosylation and acetylation {Simic, 2016 #1078}. Abnormal post-translational modifications have been linked to increased aggregations and Tau tangles. Pharmacologic approaches to block the phosphorylation of Tau through the Glycogen Synthase Kinase-3 have been attempted in the clinic; however, side effects from the small molecular inhibitor have slowed progress {Pedersen, 2015 #1079}. Tau pathology occurs intra-neuronally; however, recent evidence suggests that the protein can also propagate from cell to cell {Simic, 2016 #1078}. Tau oligomers or aggregates injected into wild-type or Tau transgenic mice show propagation and tau aggregation from the site of injection and in vitro cultures show spread of Tau from cell to cell {Simic, 2016 #1078}. Thus, Tau protein can exist outside of the cell and would be a viable target for therapeutics. Therefore a number of strategies for targeting Tau for AD and other taupathies has been proposed including small molecules preventing aggregation, anti-sense nucleotides to reduce tau expression and more recently immunotherapy.

Immunotherapy approaches for the reduction of Tau in AD have focused on both active and passive immunization. However, to date no immunization therapy has been developed for PiD. Active immunization protocols utilize a peptide of Tau which then elicit a generalized immune response against all Tau species {Pedersen, 2015 #1079; Valera, 2015 #1068}. Similarly, passive immunization strategies have been developed targeting either total 4R Tau protein {Pedersen, 2015 #1079; Valera, 2015 #1068} or phosphorylated or acetylated Tau. While this may prove to be effective at reducing total Tau protein, studies with Tau knocked out in mice {Ikegami, 2000 #1083; Harada, 1994 #1085} and in neurons in vitro {Dawson, 2001 #1084} have shown that this strategy might have some deleterious effects. Furthermore, down-regulation of Tau in oligodendrocytes by siRNA has been shown to reduce the expression of MBP protein leading to reduced myelination {Seiberlich, 2015

1086}. Thus, targeting total Tau for reduction may not be best therapeutic approach. Moreover since these antibodies mostly target 4R Tau or phospho-epitopes they might not be suitable for the treatment of other taupathies such as PiD. To date, there has been little or no effort to specifically target the 3R Tau protein.

SUMMARY

In alternative embodiments, provided are methods for the treatment, amelioration, prevention or reduction of symptoms, of a neurodegenerative disorder or a condition, wherein optionally the neurodegenerative disorder or a condition is a taupathy or any disorder or condition associated with a 3-repeat (3R or 3-R) accumulation, and optionally the taupathy is Alzheimer's Disease (AD), Pick's Disease (PiD) or Fronto-temporal lobar degeneration (FTLD), comprising:

administering to an individual in need thereof an antibody that specifically targets, or specifically binds to, a 3-repeat (3R) Tau polypeptide and does not specifically recognize or bind to a 4-repeat (4R) Tau polypeptide, and optionally the antibody is a human or a humanized antibody, or a synthetic scAb, and optionally the antibody is a single chain antibody (scAb), and optionally the scAb is a human scAb or a humanized scAb, or a synthetic scAb, and optionally the scAb is encoded by a sequence comprising or consisting of SEQ ID NO:1, or has a sequence comprising or consisting of SEQ ID NO:2, and optionally the antibody comprises or consists of an amino acid sequence compr and optionally the antibody or scAb comprises or consists of an amino acid sequence comprising:

optionally, an amino terminal secretory signaling sequence, or an amino terminal CD5 secretory signaling sequence (or the amino terminal 25 residues of SEQ ID NO:2, or MPMGSLQPLATLYLLGMLVASCLGG (SEQ ID NO:3);

a $V_H$ domain MEQVNLRESGAEVKKP-GASVKVSCKVSGYTFTGYY MHWVRQAPGQ-GLEWMGWINSNSGATKYAQKFQGRVT-MTRDTSITT AYMELSSLRSDDTAVYYCARGA-RDGYGFDYWGQGTLVTVL (SEQ ID NO:4);

a hinge domain, or a hinge domain, optionally comprising or consisting of AGGGGSGGGGSGGGGSGAP (SEQ ID NO:5);

a $V_L$ domain SYVLTQPPSASGTPGQRVTISCSG-GSSNIGSNAVS WYQQLPGTAPK LLIFT-NDQRPSGVPDRFSGSKSGTSAPLAISGLQS EDESDYYCATWDDSLNGWVFGGGTKVTV (SEQ ID NO:6);

and optionally, a blood brain barrier- (BBB-) transport domain, or an Apo B LDL-receptor binding domain (or DSSVIDALQYKLEGTTRLTRKRGL KLATALSL-SNKFVEGS (SEQ ID NO:8), and optionally the antibody or the scAb comprises or consists of an s3RTV5-apoB scAb antibody lacking an amino terminal CD5 secretory signaling sequence or an Apo B LDL-receptor binding domain, or lacking both an amino terminal CD5 secretory signaling sequence and an Apo B LDL-receptor binding domain, and optionally the antibody or the scAb comprises or consists of an amino acid sequence comprising: SEQ ID NO:4, SEQ ID NO:5 and SEQ ID NO:6, or an amino acid encoded by SEQ ID NO:10;

and optionally the antibody or the scAb comprises or consists of an antigen binding site, or Complement Determining Regions (CDRs), capable of binding to an epitope comprising or consisting of the amino acid sequence (SEQ ID NO: 11)
DAGLKAEEAGIGDTPSLED EAAG.

In alternative embodiments of the methods provided herein:

(a) the antibody is contained within, or on, or is formulated with, a nanoparticle, a particle, a liposome or a micelle; or (b) the antibody, nanoparticle, particle, liposome or micelle, is linked or conjugated to, or otherwise displays on its surface, a blood brain barrier (BBB)-, central nervous system (CNS)- or brain-penetrating moiety, wherein optionally the moiety comprises a fragment of an apoB protein.

In alternative embodiments of the methods provided herein:

the antibody is formulated as a pharmaceutical composition, optionally formulated for intrathecal (i.t.) or intravenous (i.v.) administration; or the antibody is administered orally, by inhalation, intrathecally (i.t.) or intravenously (i.v.), or from an implant comprising the antibody.

In alternative embodiments provided are pharmaceutical compositions, a nanoparticle, a particle, a liposome or a micelle, or an implant, comprising an antibody that specifically targets, or specifically binds to, a 3-repeat (3R) Tau polypeptide and does not specifically recognize or bind to a 4R Tau polypeptide, and optionally the antibody is a single chain antibody (scAb), and optionally the scAb is encoded by a sequence comprising SEQ ID NO:1, or has a sequence comprising SEQ ID NO:2, and optionally the antibody, nanoparticle, particle, liposome or micelle, is linked or conjugated to, or otherwise displays on its surface, a blood brain barrier (BBB)-, central nervous system (CNS)- or brain-penetrating moiety, wherein optionally the moiety comprises a fragment of an apoB protein.

In alternative embodiments provided are recombinant or synthetic single chain antibodies (scAb) encoded by a sequence comprising SEQ ID NO:1, or has a sequence comprising SEQ ID NO:2.

In alternative embodiments provided are kits comprising an antibody that specifically targets, or specifically binds to, a 3-repeat (3R) Tau polypeptide and does not specifically recognize or bind to a 4R Tau polypeptide, and optionally the antibody is a single chain antibody (scAb), and optionally the scAb is encoded by a sequence comprising SEQ ID NO:1, or has a sequence comprising SEQ ID NO:2, and optionally the kit is a diagnostic kit, and the antibody is linked to or conjugated to a detectable moiety, or the kit comprises a detectable antibody that specifically binds to the antibody that targets, or specifically binds to, a 3-repeat (3R) Tau polypeptide, and optionally the kit comprises components for carrying out an ELISA assay.

In alternative embodiments provided are kits comprising a pharmaceutical composition, a nanoparticle, a particle, a liposome or a micelle, or an implant as provided herein, or a recombinant or synthetic single chain antibody (scAb) as provided herein.

In alternative embodiments provided are Uses of a pharmaceutical composition, a nanoparticle, a particle, a liposome or a micelle, or an implant as provided herein, or a recombinant or synthetic single chain antibody (scAb) as provided herein, or a kit as provided herein, for the treatment, amelioration, prevention or reduction of symptoms, of a neurodegenerative disorder or a condition, wherein optionally the neurodegenerative disorder or a condition is a taupathy or any disorder or condition associated with a 3R Tau accumulation, and optionally the taupathy is Alzheimer's Disease (AD), Pick's Disease (PiD) or Fronto-temporal lobar degeneration (FTLD).

In alternative embodiments provided are methods for diagnosing a neurodegenerative disorder or a condition comprising a taupathy or any disorder or condition associated with a 3R Tau accumulation, and optionally the taupathy is Alzheimer's Disease (AD), Pick's Disease (PiD) or Fronto-temporal lobar degeneration (FTLD), comprising:

(a) providing a sample from an individual, wherein optionally the sample is a blood, serum, cerebral spinal fluid (CSF) or tissue sample, wherein optionally the tissue sample is a nerve or a brain tissue sample or histological section;

(b) reacting or testing the sample with a composition capable of an antibody that specifically targets, or specifically binds to, a 3-repeat (3R) Tau polypeptide and does not specifically recognize or bind to a 4R Tau polypeptide, and optionally the antibody is a single chain antibody (scAb), and optionally the scAb is encoded by a sequence comprising SEQ ID NO:1, or has a sequence comprising SEQ ID NO:2; and (c) detecting the specific binding of the antibody with a 3-repeat (3R) Tau polypeptide in or from the sample, wherein detection of the 3-repeat (3R) Tau polypeptide in the sample diagnoses the presence of a neurodegenerative disorder or a condition comprising a taupathy or any disorder or condition associated with a 3R Tau accumulation, and optionally the taupathy is Alzheimer's Disease (AD), Pick's Disease (PiD) or Fronto-temporal lobar degeneration (FTLD).

In alternative embodiments provided are methods for determining the effectiveness of treatment of a neurodegenerative disorder or a condition comprising a taupathy or any disorder or condition associated with a 3R Tau accumulation, and optionally the taupathy is Alzheimer's Disease (AD), Pick's Disease (PiD) or Fronto-temporal lobar degeneration (FTLD), comprising:

(a) providing at least two comparable samples from an individual: wherein a first sample is taken before a treatment begins and a second sample is taken after the treatment begins, or the first and the second samples are taken at two different time points after a treatment begins, wherein optionally the sample is a blood, serum, cerebral spinal fluid (CSF) or tissue sample, wherein optionally the tissue sample is a nerve or a brain tissue sample or histological section;

(b) reacting or testing the samples with a composition capable of an antibody that specifically targets, or specifically binds to, a 3-repeat (3R) Tau polypeptide and does not specifically recognize or bind to a 4R Tau polypeptide, and optionally the antibody is a single chain antibody (scAb), and optionally the scAb is encoded by a sequence comprising SEQ ID NO:1, or has a sequence comprising SEQ ID NO:2; and (c) detecting the specific binding of the antibody with a 3-repeat (3R) Tau polypeptide in or from the samples, wherein detection of less 3-repeat (3R) Tau polypeptide in the second sample as compared to the first sample determines that the treatment is effective.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

Figures are described in detail herein.

FIG. 2C, exposure time 15 min.); 2-fold dilutions of 3R Tau or 4R Tau were separated on polyacrylamine gel and blotted before being probed with the 3RT scFV; sSecondary biotin labeled anti-human was used to detect the scFV. The 3RT scFV selectively recognizes 3RTau in neuronal cell models (FIG. 2D), transgenic mouse brains (FIG. 2E) and in the brains of patients with AD and PiD (FIG. 2F), as further discussed in Example 1, below.

FIG. 4 illustrates the nucleotide sequence encoding the exemplary single chain antibody 3RT-apoB, including secretory sequence and V5 tag (SEQ ID NO:1), as further discussed in Example 1, below.

FIG. 5 illustrates the amino acid sequence of the exemplary single chain antibody s3RTV5-apoB (SEQ ID NO:2): beginning from the 5' end, blue letters indicated the CD5 secretory signaling sequence (or the amino terminal 25 residues, or MPMGSLQPLATLYLLGMLVASCLGG (SEQ ID NO:3)); highlighted sequences indicated the 3RT scFV with the blue highlighted region the $V_H$ domain MEQVNLRESGAEVKKPGASVKVSCKVSGYTFTGYYMHWVRQAPGQGLEW MGWINSNSGATKYAQKFQGRVTMTRDTSITTAYMELSSLRSDDTAVYYCAR GARDGYGFDYWGQGTLVTVLA (SEQ ID NO:4), yellow region the hinge domain (or GGGGSGGGGSGGGGSGAP (SEQ ID NO:5), and green region the $V_L$ domain (or SYVLTQPPSASGTPGQRVTISCSGGSSNIGSNAVSWYQQLPGTAPKLLIFT NDQRPSGVPDRFSGSKSGTSAPLAISGLQSEDESDYYCATWDDSLNGWVFGG GTKVTV (SEQ ID NO:6); Green letters indicate the V5 epitope tag (or KPIPNPLLGLDS (SEQ ID NO:7) and the red letters indicate the Apo B LDL-receptor binding domain (or DSSVIDALQYKLEGTTRLTRKRGLKLATALSLSN KFVEGS (SEQ ID NO:8)), as further discussed in Example 1, below.

(SEQ ID NO: 2)
MPMGSLQPLATLYLLGMLVASCLGGMEQVNLRESGAEVKKPGASVKVSCK

VSGYTFTGYYMHWVRQAPGQGLEWMGWINS NSGATKYAQKFQGRVTMTR

DTSITTAYMELSSLRSDDTAVYYCARGARDGYGFDYWGQGTLVTVLAGGG

GSGGGGSGGGGSGAPSYVLTQPPSASGTPGQRVTISCSGGSSNIGSNAVS

WYQQLPGTAPKLLIFTNDQRP SGVPDRFSGS KSGTSAPLAISGLQSED

ESDYYCATWDDSLNGWVFGGGTKVTVGPFEGKPIPNPLLGLDSTRTGVDS

SVIDALQYKLEGTTRLTRKRGLKLATALSLSNKFVEGS

Figure 6:
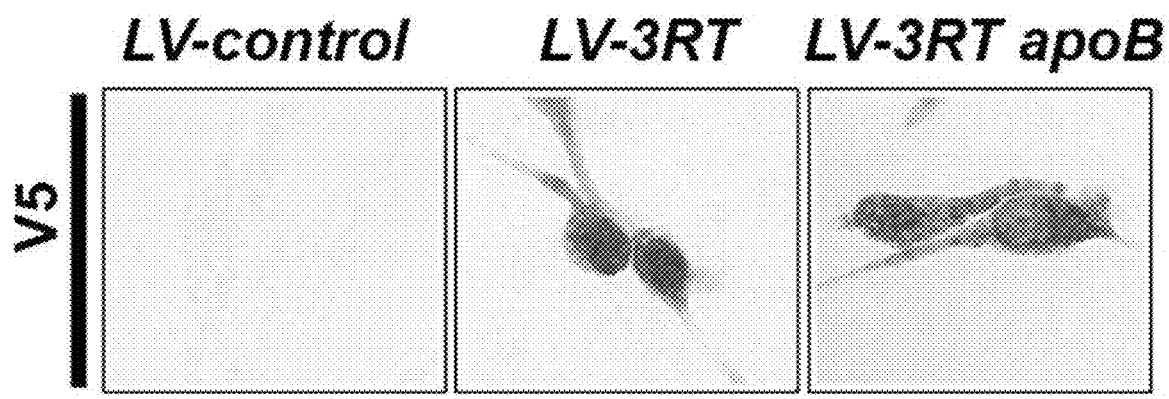

FIG. 6 illustrates images of an immunocytochemical analysis with anti-V5 antibody of coverslips with neuronal cells infected with LV-control, 3RT and 3RT-apoB; cells infected with LV-bobi were negative; while cells infected with LV-3RT and 3RT-apoB displayed strong V5 immunoreactivity in over 90% of the cells, as further discussed in Example 1, below.

Figure 7:
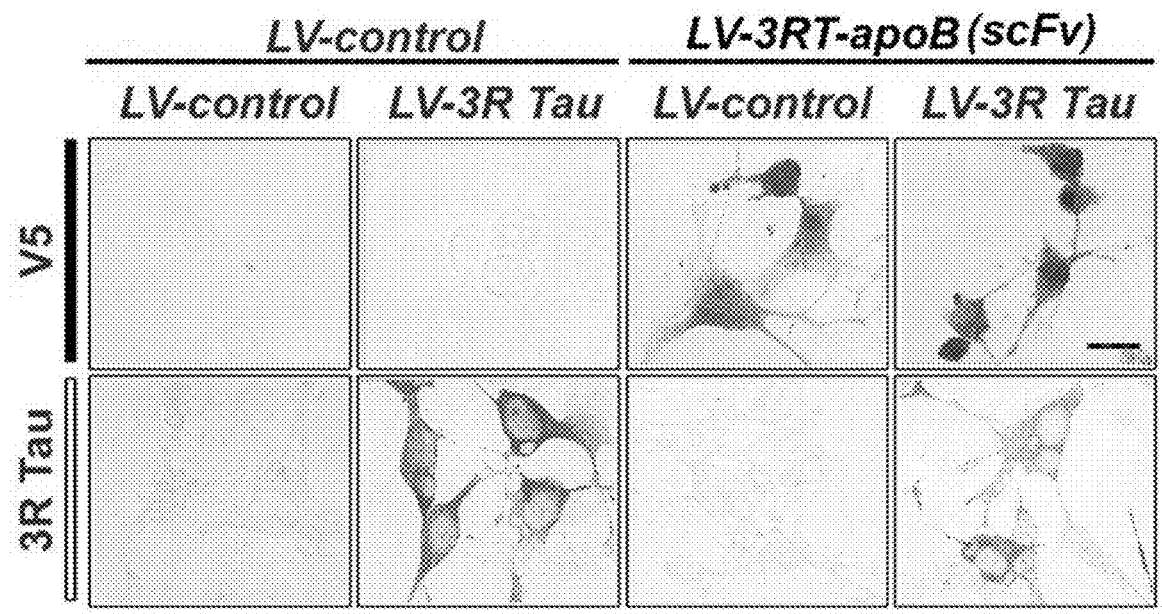

FIG. 7 illustrates images of an immunocytochemical analysis of 3RTau in B103 neuronal cells co-infected with a lentivirus vector over-expressing 3RTau along with a lentivirus vector expressing single chain antibody 3RT alone (LV-s3RTV5) or with the apoB BBB transport tag (LV-s3RTV5-apoB); a control virus was included (LV-control); both scFv coding vectors expressed equivalent amounts of the 3RT scFV and were able to reduce the accumulation of 3RTau in the neuronal cells; the control vector (LV-control) did not appear to have an effect on the neuronal accumulation of 3RTau, as further discussed in Example 1, below.

FIG. 8A-E illustrate images of an immunocytochemical analysis of 3R Tau in chamber experiments: the LV-s3RTV5, LV-s3RTV5-apoB and LV-control lentivector expressing cells were cultured in the top chamber and the LV-3R Tau expressing cells were cultured in the bottom chamber (FIG. 8A); analysis of the cells in the lower chamber showed similar levels of uptake of the exemplary scFvs for LV-s3RTV5 and LV-s3RTV5-apoB infected cells; both the exemplary s3RTV5 and s3RTV5-apoB significantly reduced the accumulation of 3R Tau similar to the co-infection experiment (FIG. 8B), as further discussed in Example 1, below. (FIG. 8C) Relative fluorescence was analyzed to determine the level of 3RTau. (FIG. 8D) Lower chamber coverslips were immunostained for against V5 (3RT scFV) (green). (FIG. 8E) Relative fluorescence was analyzed to determine the level of V5. #indicates statistical significance p<0.05 compared to LV-control by one-way ANOVA with post hoc Tukey-Kramer. Scale bar represents 10 μm.

FIG. 9A-F graphically (FIG. 9C, F) and schematically (FIG. 9A-B, D-E) illustrate the 3RTau mutant transgenic animal model mimicking the pathology of Pick's Disease, Alzheimer's and other taupathies: mice display accumulation of 3RTau in the necortex and limbic system, tangles and pick body like formation, phosphorylation of Tau with memory and learning deficits, as further discussed in Example 1, below.

Figure 9A:
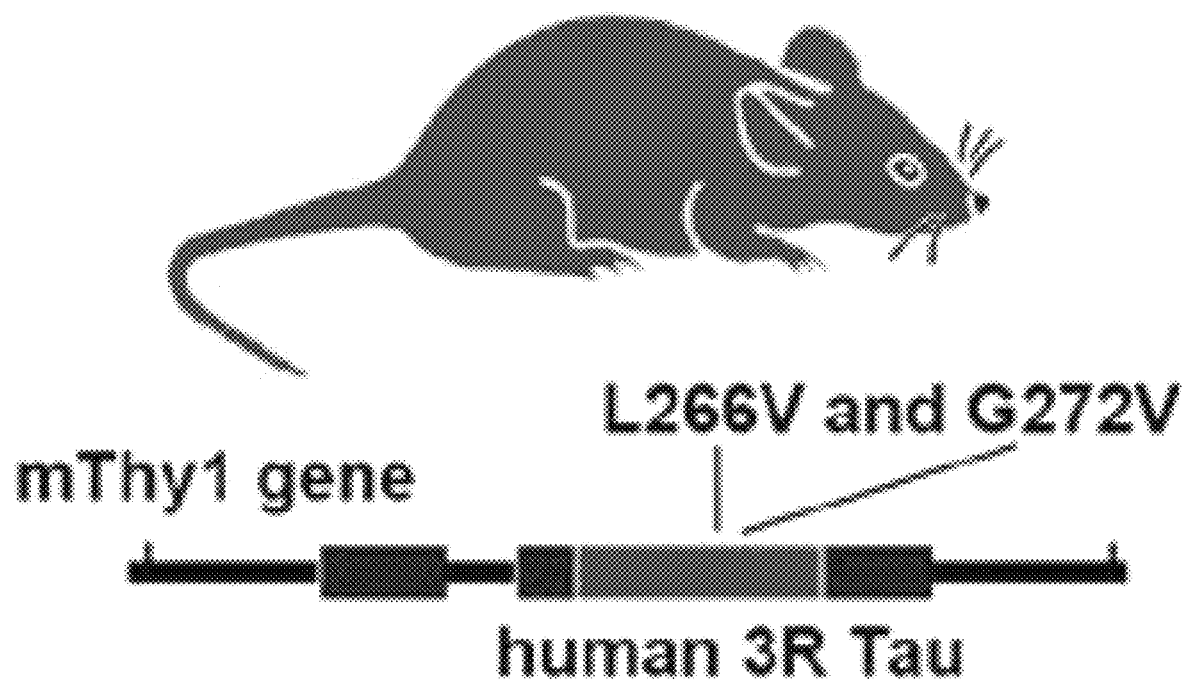

FIG. 9A schematically illustrates the heterologous nucleic acid coding sequence implanted in the genome of the transgenic mouse animal model.

Figure 9B:
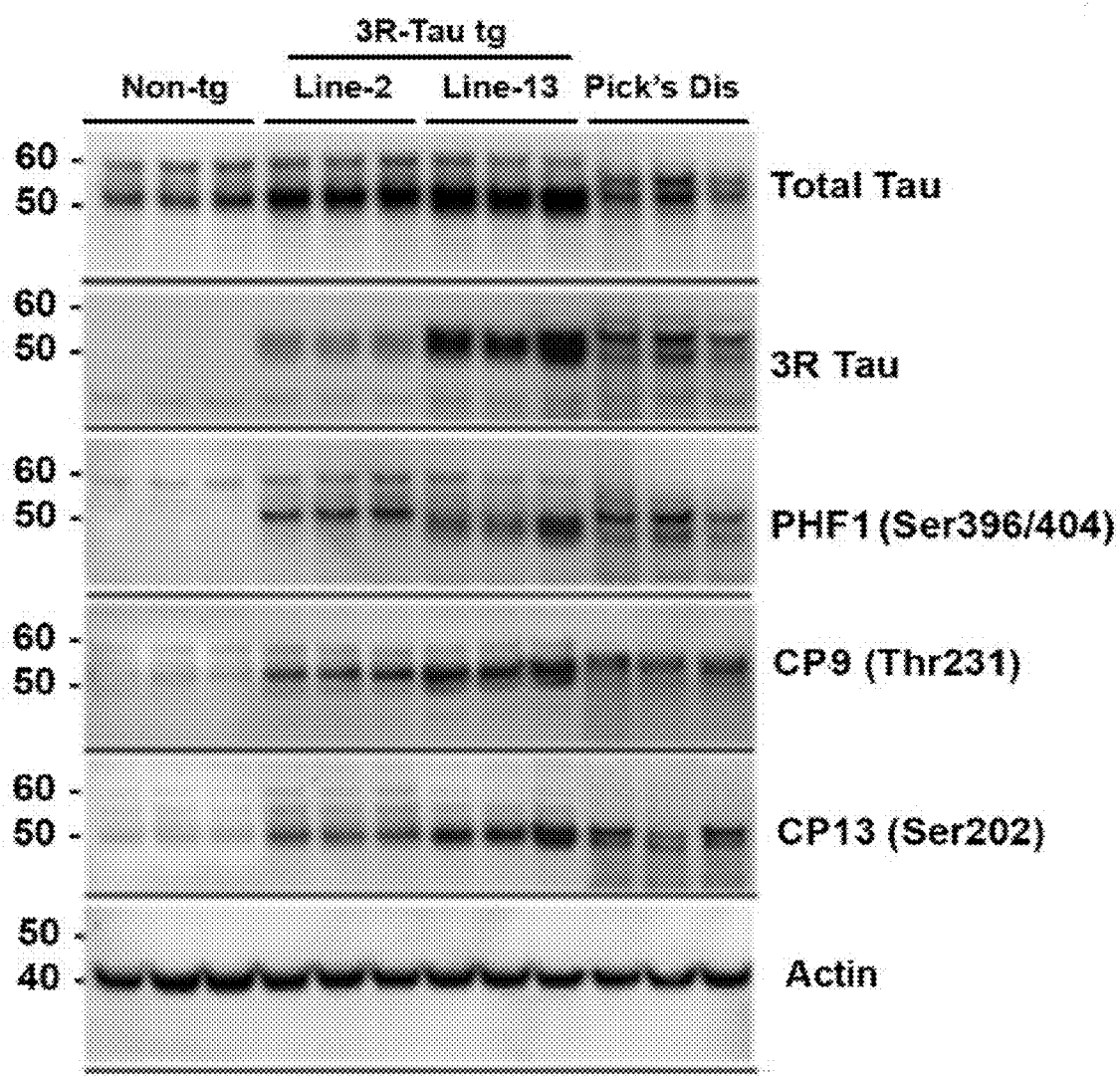

FIG. 9B schematically illustrates a representative Western blot (SDS) of the levels of Total Tau, 3R Tau and phospho-Tau (PHF-1—Ser294/404), (CP9—Thr231), (CP13—Ser202) with Actin as a loading control. Insoluble (membrane) fractions from Line 13 was compared to Line 2 and non-tg mice. Across all lines, Tau was detected as double bands between 50-60 kDa. n=6 non-tg, n=6 Line 13 3RTau-tg, and n=6 Line 2 3RTau-tg.

Figure 9C:
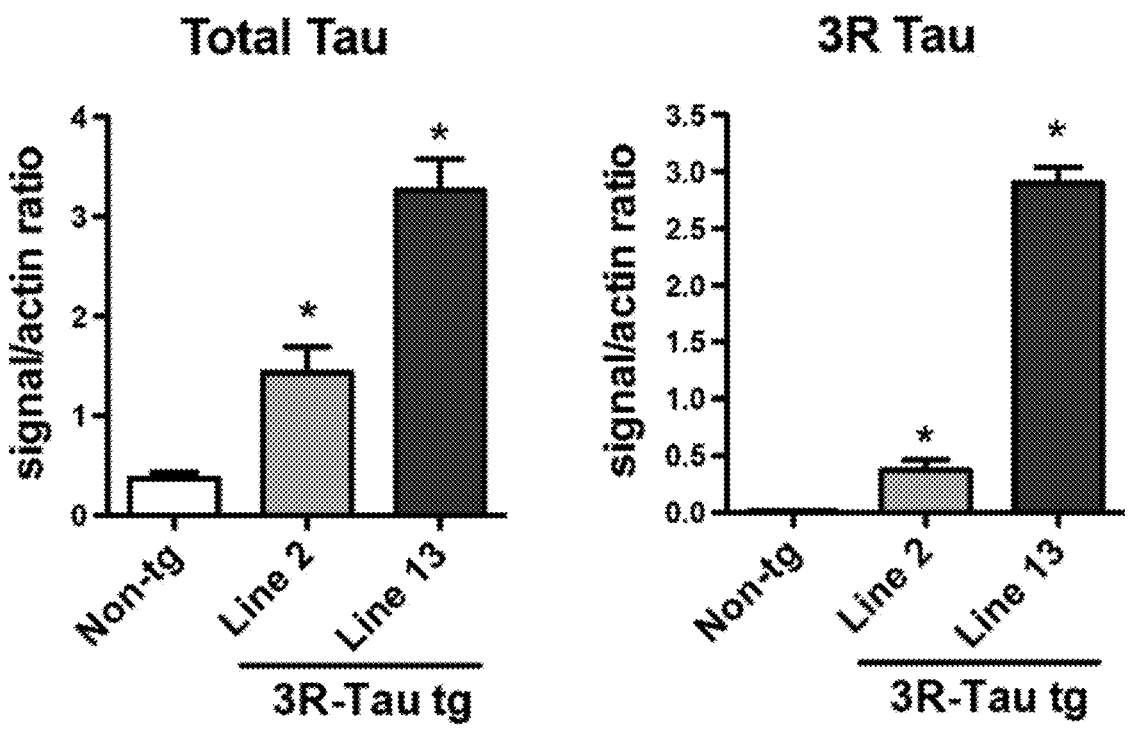

FIG. 9C graphically illustrates data for an analysis of levels of Total Tau (left graph) and 3RTau (right graph) from a Western blot comparing Line 13 to Line 2 and non-tg mice; n=6 non-tg, n=6 Line 13 3RTau-tg, and n=6 Line 2 3RTau-tg; *p<0.05 compared to non-tg control using one way ANOVA with Dunnett's posthoc test.

Figure 9D:
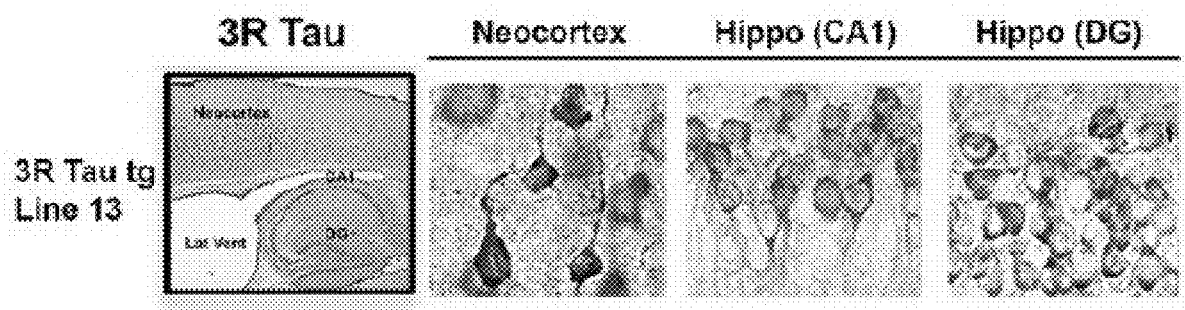

FIG. 9D schematically illustrates an image of 3RTau staining of vibratome sections of Line 13 3RTau-tg mouse brain; vibratome sections were immunostained with an antibody against 3R Tau and analyzed by bright field microscopy; panel on the left is low-magnification (20×) photomicrograph including: neocortex, hippocampus CA1 and dentate gyrus (DG) regions; panels to the right are higher magnification (600×) of the corresponding regions displaying 3RTau staining.

Figure 9E:
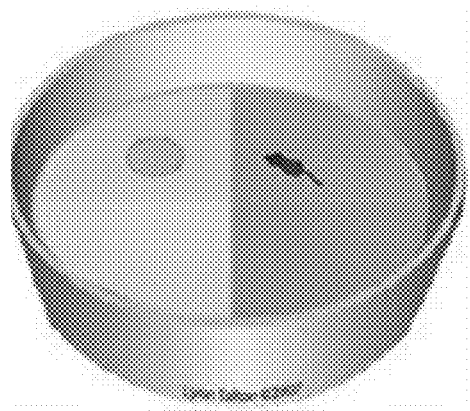

FIG. 9E schematically illustrates a Morris water maze, which is a behavioral test used to assay spatial learning and memory in rodents (mice) and to assess damage or degeneration to particular cortical regions such as the neocortex and hippocampus; mice are placed into the pool with a visible platform and several visual cues on the perimeter of the pool and allowed to find the platform for 3 consecutive days; after this, the platform is submerged (hidden) and the mouse is forced to find the platform using memory and visual pool cues alone; and distance and time of swimming to platform escape are recorded.

Figure 9F:
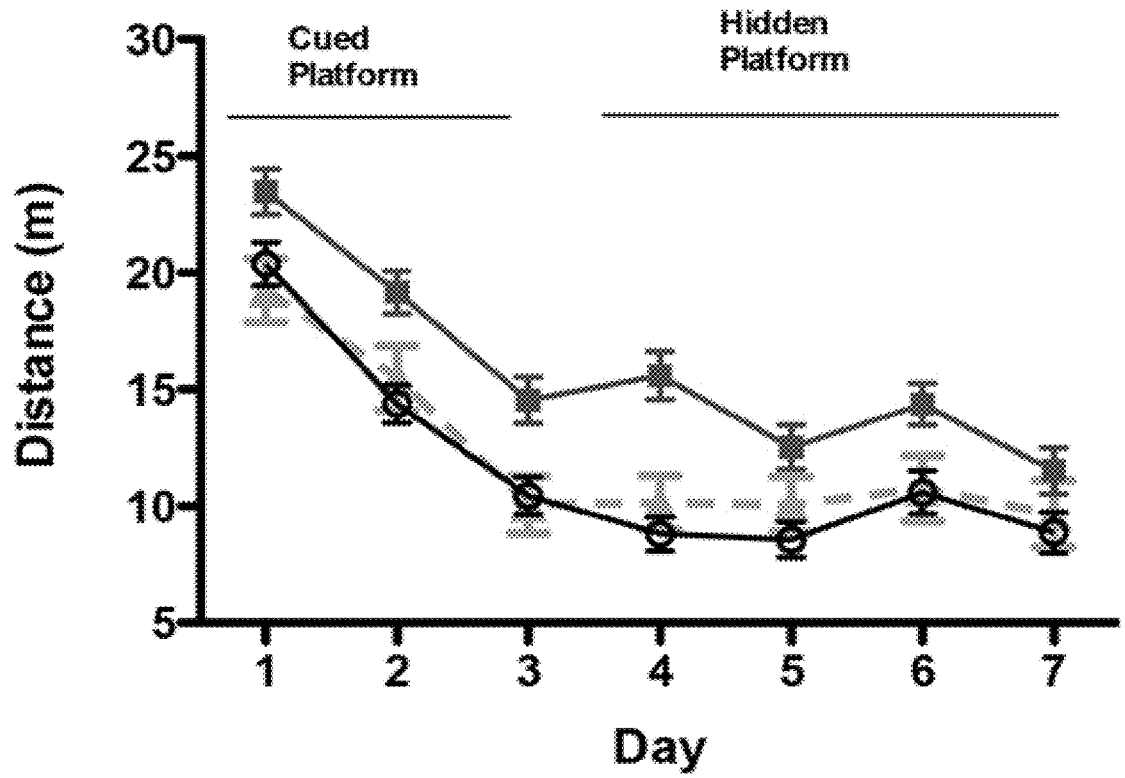

FIG. 9F graphically illustrates data where mice were evaluated for memory and context dependent learning in the Morris water maze; water maze testing is presented as distance traveled to find the platform; during the cued portion of the test, both the non-tg and 3RTau-tg mice performed similarly; however, during the hidden portion of the test, the 3RTau-tg mice traveled farther (taking longer) to the platform than the non-tg control; n=12 non-tg, n=12 Line 2 3RTau-tg, n=12 Line 13 3RTau-tg. ***p<0.05 compared to 3RTau-tg mice using one way ANOVA with Dunnett's posthoc test.

Figure 10A:
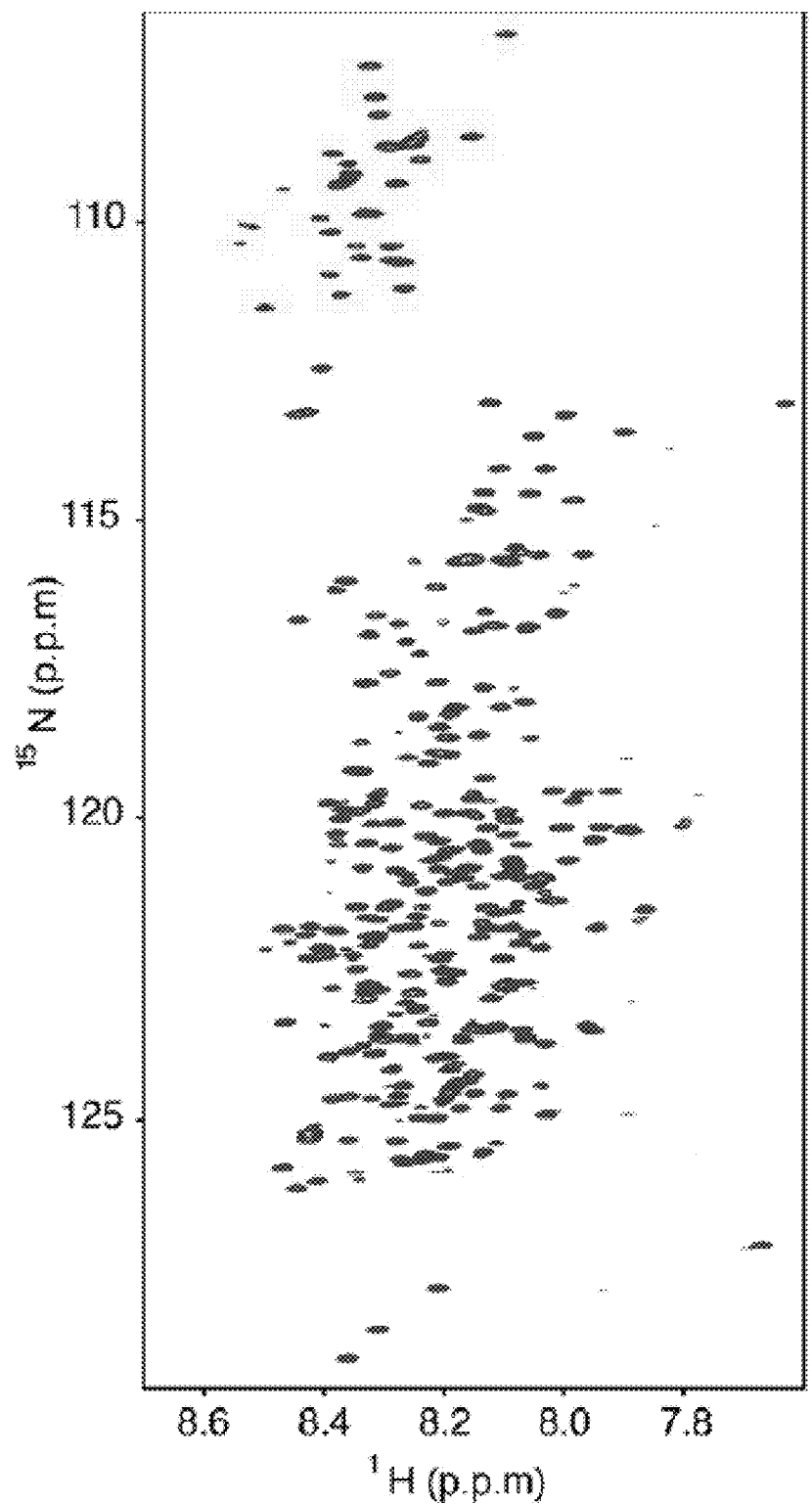
Figure 10B:
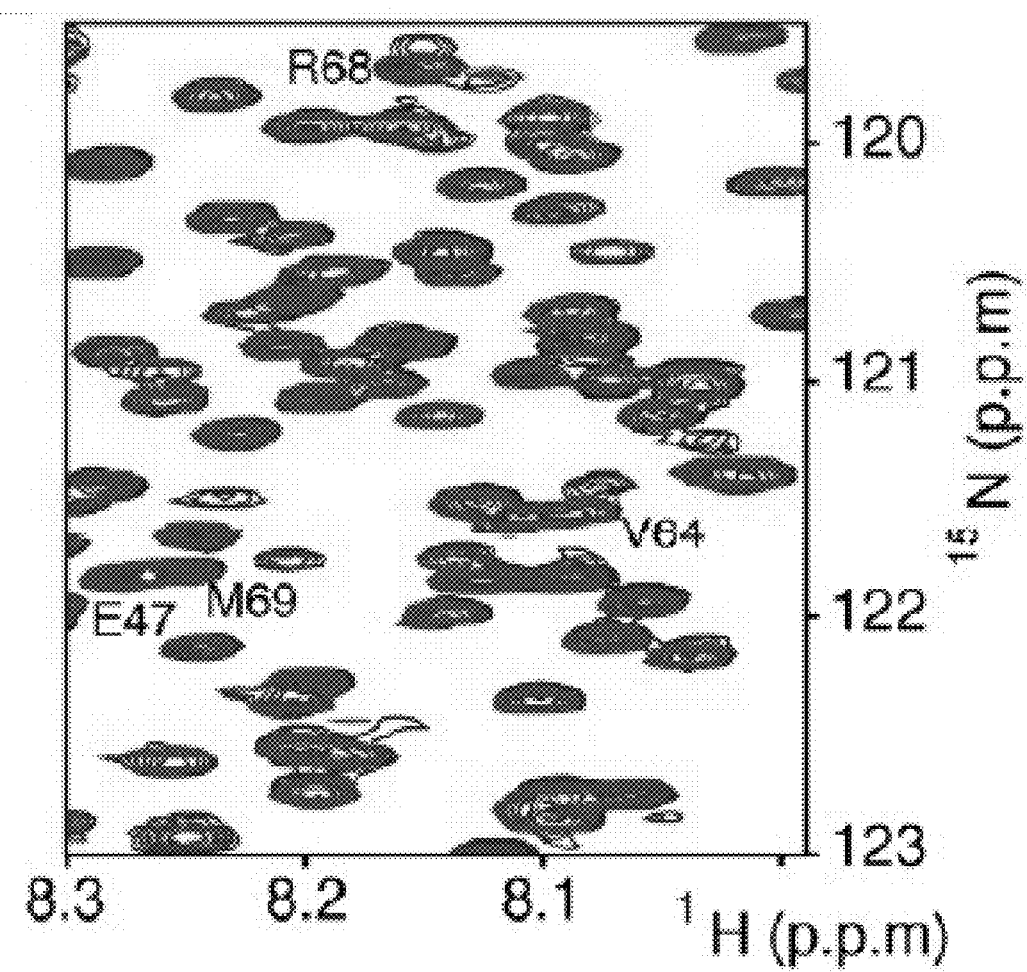
Figure 10C:
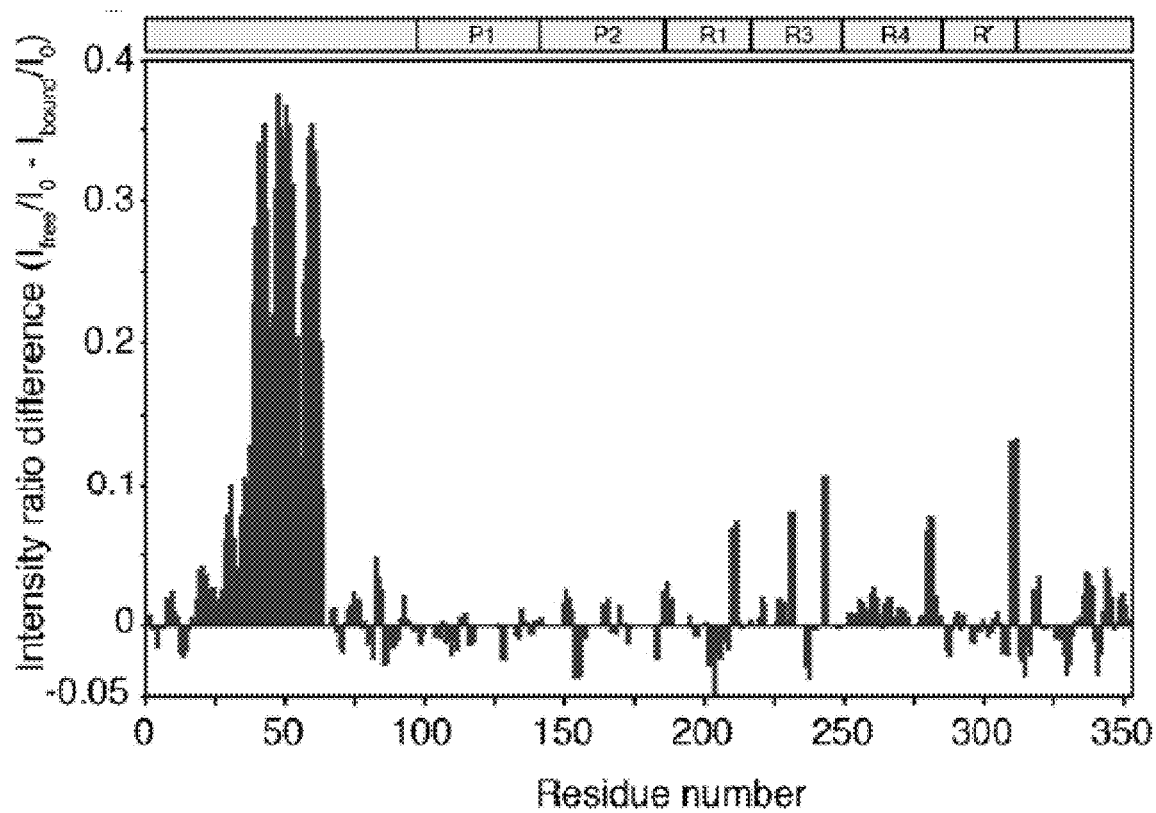

FIG. 10A-C illustrates images of the interaction between the exemplary scFv and 3RTau isoform 352 (tau352) by NMR spectroscopy; to identify the epitope, tau352 and the exemplary 3RT antibody were recombinantly expressed in $E.\ coli$ and HEK293 cells, respectively, and 2D $^1$H-$^{15}$N heteronuclear single quantum coherence (HSQC) spectra were recorded on tau352 in absence and presence of exemplary 3RT antibody, as described in detail below in Example 2. Addition of the exemplary 3RT single chain antibody at an approximately equimolar ratio lead to the appearance of several new peaks with no changes in chemical shifts of the remaining signals in the tau352 spectrum (FIG. 10A,B), suggesting strong antibody binding. Furthermore, the presence of 3RT scFv resulted in the attenuation of signal intensity for resonances of residues 40-62 (FIG. 10C), caused by the increase in molecular weight upon scFv binding.

FIG. 11A-D schematically and graphically illustrates data showing that a lentiviral vector expressing the exemplary 3R Tau scFV reduces the accumulation of 3R Tau in neurons in vitro. (FIG. 11A) The 3RT scFV was cloned into the 3$^{rd}$ generation lentivirus vector with the addition of the CD5 secretory signal (ss) and the V5 epitope tag (V5) to generate LV-s3RT. This vector was further modified by the addition of the apoB brain transport peptide to generate LV-s3RT-apoB. (FIG. 11B) N2A neuronal cells co-infected with the 3RT scFV expressing vectors and a 3R Tau expressing vector were stained for the 3RT scFV (V5) and for the 3RTau protein. Coverslips were analyzed for (FIG. 11C) V5 and (FIG. 11D) 3RTau staining pixel intensity and quantified by corrected optical density. #indicates statistical significance p<0.05 compared to cells expressed co-infected with LV-3RTau and LV-control. One-way ANOVA with post hoc Tukey-Kramer. Scale bar represents 10 µm.

FIG. 12A-H schematically and graphically illustrate and summarize data showing that systemic delivery of the exemplary 3RT scFV reduces the accumulation of 3R Tau in the brain of transgenic mice. 4-month-old 3R Tau-tg and non-tg mice received a single i.p. injection of LV-3RT, LV-3RT-apoB or LV-control and were sacrificed 4 months later for analysis. (FIG. 12A, FIG. 12B) Immunocytochemical analysis with antibodies against the V5 tag to detect the 3RT scFV in the frontal cortex and hippocampus of non-tg and 3R Tau-tg mice. (FIG. 12C, FIG. 12D) Immunocytochemical analysis with antibodies against 3R Tau in the frontal cortex and hippocampus of non-tg and 3R-Tau-tg mice. (FIG. 12E, FIG. 12F) Immunocytochemical analysis with antibodies against phosphor-Tau (PHF-1) in the frontal cortex and hippocampus of non-tg and 3R-Tau-tg mice. (FIG. 12G, FIG. 12H) Immunocytochemical analysis with antibodies against total Tau (T-Tau) in the frontal cortex and hippocampus of non-tg and 3R-Tau-tg mice. (FIG. 12B, FIG. 12D, FIG. 12F, FIG. 12H) Immunoreactivity quantified and expressed as corrected optical density of sections. * indicates statistical significance p<0.05 compared to non-tg mice. #indicates statistical significance p<0.05 compared to 3R Tau-tg mice treated with LV-control by one-way ANOVA with post hoc Tukey-Kramer. Scale bar represents 25 µm.

FIG. 13A-D schematically and graphically illustrate and summarize data showing that the exemplary 3RT-apoB scFV co-localizes with neurons in the brain. Double immunocytochemical analysis in the neocortex of non-tg and 3RTau tg mice treated with LV-3RT, LV-3RT-apoB and LV-control with antibodies to V5 (red, 3RT epitope tag) and the neuronal markers (FIG. 13A) NeuN or (FIG. 13C) Map2. Analysis of % cells showing co-localization between V5 (3RT) and (FIG. 13B) NeuN, (FIG. 13D) Map2. Scale bar represents 10 µm, and 5 µm in detail figure.

FIG. 14A-D schematically and graphically illustrate and summarize data showing that the exemplary 3RT-apoB scFV co-localizes with glial cells in the brain. Double immunocytochemical analysis in the neocortex of non-tg and 3RTau tg mice treated with LV-3RT, LV-3RT-apoB and LV-control with antibodies to V5 (red, 3RT epitope tag) and the astrocyte marker (FIG. 14A) GFAP and microglia marker (FIG. 14C) Iba1 imaged with the laser scanning confocal microscope. Analysis of % cells showing co-localization between V5 (3RT) and (FIG. 14B) GFAP and FIG. 14 (D) Iba. Scale bar represents 10 µm, and 5 µm in detail figure.

FIG. 15A-D schematically and graphically illustrate and summarize data showing that the exemplary 3RT-apoB scFV co-localizes with 3RTau and targets 3RTau to the early endosome. (FIG. 15A) Double immunofluorescent analysis in the neocortex of non-tg and 3RTau tg mice treated with LV-3RT, LV-3RT-apoB and LV-control with antibodies to V5 (red, 3RT epitope tag) and 3RTau (green) and imaged with the laser scanning confocal microscope. (FIG. 15C) Double immunofluorescent analysis with V5 (red, 3RT epitope tag) and LC3 (green). (FIG. 15B, FIG. 15D) Analysis of % cells showing co-localization. Scale bar represents 10 µm, and 5 µm in detail figure.

FIG. 16A-D schematically and graphically illustrate and summarize data showing that the exemplary 3RT-apoB scFV co-localizes with 3RTau and targets 3RTau to the early endosome. (FIG. 16A) Representative double immunofluorescent images in the neocortex of non-tg and 3RTau tg mice treated with LV-3RT, LV-3RT-apoB and LV-control with antibodies to V5 (red, 3RT epitope tag) and 3RTau (green) analyzed with the laser scanning confocal microscope. (FIG. 16C) Double immunofluorescent analysis with 3RTau (green) and Rab5 (red). (FIG. 16E) Representative double immunofluorescent images in the neocortex with LC3 (red) and 3RTau (green) and analyzed with the laser scanning confocal microscope. (FIG. 16G) Representative double immunofluorescent images of sections labeled with antibodies against V5 (red, 3RT epitope tag) and LC3 (green). (FIG. 16B, FIG. 16D, FIG. 16F, FIG. 16H) Analysis of % cells showing co-localization. Scale bar represents 10 µm, and 5 µm in detail figure. For analysis, 3RTau tg LV-control (n=12); LV-3RT (n=12); LV-3RT-apoB (n=12) and non-tg mice LV-control (n=6).

FIG. 17A-F schematically and graphically illustrate and summarize data showing the delivery of the 3RT-apoB scFV ameliorated astroglial and neural pathological markers in the CNS; 4-month-old 3R Tau-tg and non-tg mice received a single i.p. injection of LV-3RT, LV-3RT-apoB or LV-control and were sacrificed 4 months later for analysis; the neocortex and hippocampus were immunostained with antibodies against the (FIG. 17A) astroglial glial fibrillary acidic protein (GFAP), (FIG. 17C) neuronal marker NeuN, (FIG. 17E) and dendritic marker MAP2 (green). (FIG. 17B) GFAP immunoreactivity expressed as corrected optical density of sections. (FIG. 17D) Stereological estimates (dissector method) of total NeuN-positive neuronal counts in the frontal cortex. (FIG. 17F) Image analysis of % area of the neuropil covered by MAP2 post-synaptic processes. * indicates statistical significance p<0.05 compared to non-tg mice. #indicates statistical significance p<0.05 compared to 3R Tau-tg mice treated with LV-3RT by one-way ANOVA with post hoc Tukey-Kramer. Scale bar represents 20 µm.

Figure 18:
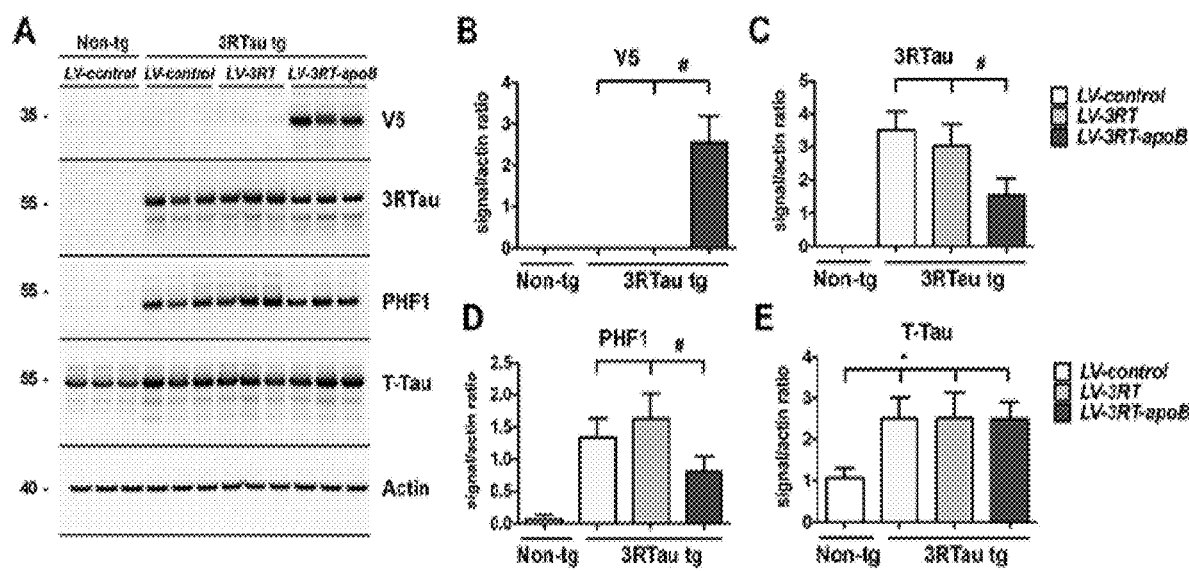

FIG. 18 schematically and graphically illustrate and summarize data showing that the exemplary 3RT-apoB antibody reduces Tau accumulation in the brain. (FIG. 18A) Representative, immunoblot analysis of brain homogenates from non-tg and 3RTau tg mice treated with LV-3RT, LV-3RT-apoB or LV-control showing levels of Tau proteins: 3RTau, p-Tau (PHF1), and total Tau (T-Tau) as well as the level of the 3RT scFV protein (V5) with ß-actin as a loading control. Image analysis of pixels of (FIG. 18B) V5, (FIG. 18C) 3RTau, (FIG. 18D) PHF1, and (FIG. 18E) T-Tau immunoreactivity analyzed as ratio to ß-actin signal. * indicates statistical significance p<0.05 compared to non-tg mice. #indicates statistical significance p<0.05 compared to 3R Tau tg mice with or without treatment by LV-3RT by one-way ANOVA with post hoc Tukey-Kramer. For analysis, 3RTau tg LV-control (n=12); LV-3RT (n=12); LV-3RT-apoB (n=12) and non-tg mice LV-control (n=6).

Figure 19:
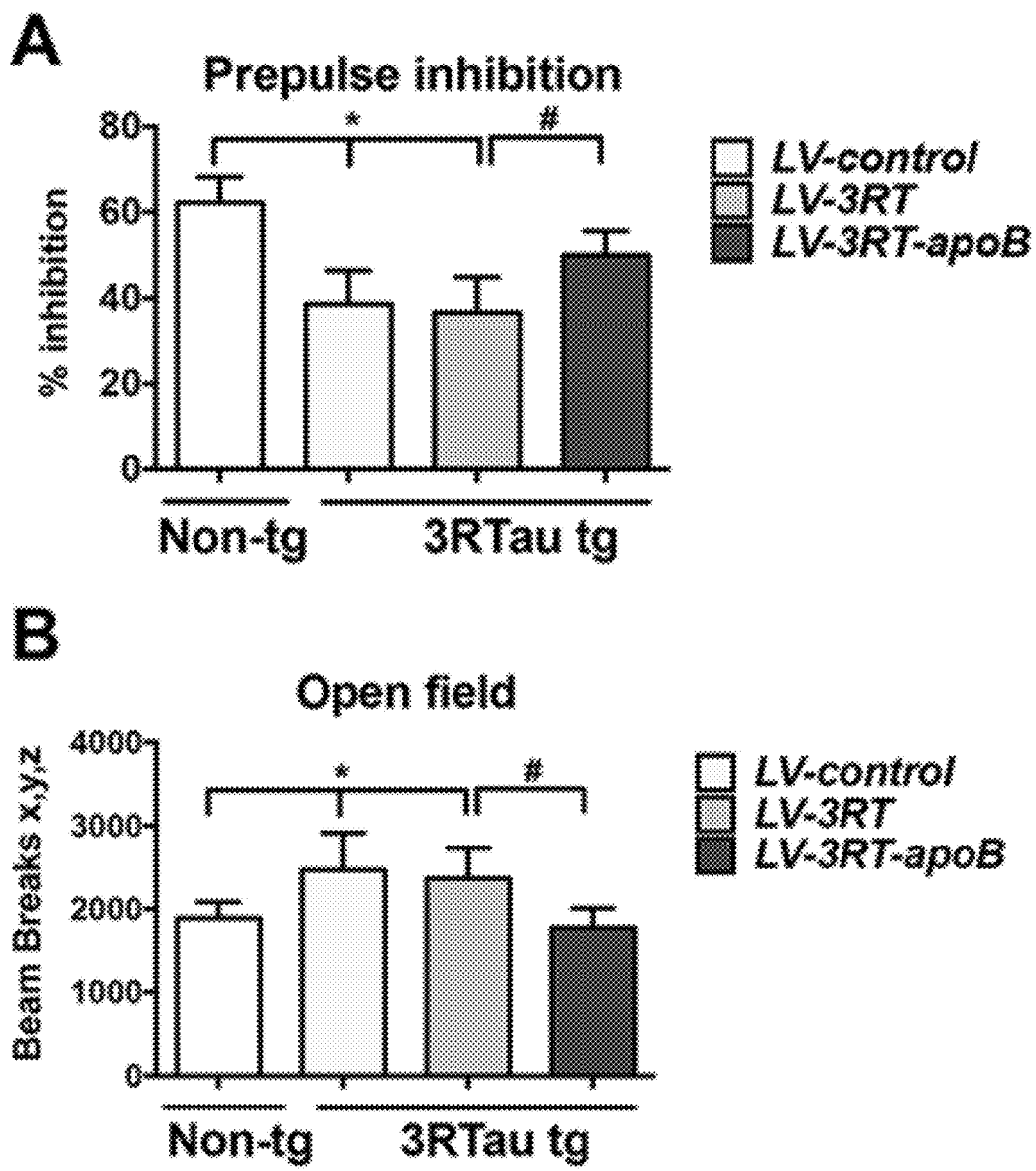

FIG. 19 graphically illustrates data showing that systemic delivery of the 3RT-apoB with a lentiviral vector ameliorated behavioral deficits in the 3RTau tg mouse. Mice were assessed in the (FIG. 19A) Prepulse inhibition (PPI) test, compared to non-tg mice treated with LV-control, the 3RTau tg mice treated with LV-control displayed reduced % of inhibition, in contrast mice treated with LV-3RT-apoB displayed normal levels of % of inhibition and (FIG. 19B) in the open field test, 3RTau tg mice treated with LV-control or 3LV-RTau alone, displayed hyperactivity while 3RTau tg mice treated with LV-3RT-apoB displayed levels of activity similar to non-tg controls. * indicates statistical significance p<0.05 compared to non-tg mice. #indicates statistical significance p<0.05 compared to 3R Tau-tg mice treated with LV-3RT by one-way ANOVA with post hoc Tukey-Kramer.

Like reference symbols in the various drawings indicate like elements.

DETAILED DESCRIPTION

In alternative embodiments, provided are compositions, including products of manufacture and kits, and methods, for the treatment, amelioration, prevention or reduction of symptoms, of neurodegenerative disorders and conditions, including taupathies such as Alzheimer's Disease (AD), Pick's Disease (PiD) and Fronto-temporal lobar degeneration (FTLD), or any disorder or condition associated with a 3R Tau accumulation. In alternative embodiments, provided are compositions such as antibodies, e.g., single chain antibodies, that target or specifically bind to 3-repeat (3R) Tau for the treatment of neurodegenerative disorders and conditions, including taupathies such as Alzheimer's Disease (AD), Pick's Disease (PiD) and Fronto-temporal lobar degeneration (FTLD), or any disorder or condition associated with a 3R Tau accumulation, and methods for making and using them. In alternative embodiments, provided are brain-penetrating, or blood brain barrier (BBB) penetrating, antibodies, e.g., single chain antibodies (scAbs), that specifically recognize 3R Tau, and methods of using them to treat, ameliorate, prevent or decrease the symptoms of a neurodegenerative disorder or condition, including taupathies such as Alzheimer's Disease (AD), Pick's Disease (PiD) and Fronto-temporal lobar degeneration (FTLD), or any disorder or condition associated with a 3R Tau accumulation.

In alternative embodiments, single chain antibodies (scAbs) provided herein specifically recognize 3R Tau in in vitro and ex vivo assays.

Antibodies, Single Chain, Therapeutic and Humanized Antibodies

In alternative embodiments, the invention provides antibodies, and methods for using them for the treatment, amelioration, prevention or reduction of symptoms, of a neurodegenerative disorder or a condition, wherein the antibodies specifically target, or specifically bind to, a 3-repeat (3R) Tau polypeptide and do not specifically recognize or bind to a 4R Tau polypeptide.

In alternative embodiments, the antibody used to practice the compositions and methods as provided herein is a single chain antibody (scAb). In alternative embodiments, the scAb is the so-called exemplary single chain antibody s3RTV5-apoB, which is encoded by a nucleic acid sequence comprising SEQ ID NO:1, or has an amino acid sequence comprising SEQ ID NO:2 (see FIGS. 4 and 5), which includes: an amino terminal CD5 secretory signaling sequence (or the amino terminal 25 residues, or MPMGSLQPLATLYLLGMLVASCLGG (SEQ ID NO:3); a $V_H$ domain MEQVNLRESGAEVKKPGASVKVSCKVSGYTFTGYYMHWVRQAPGQGLEW MGWINSNSGATKYAQKFQGRVTMTRDTSITTAYMELSSLRSDDTAVYYCAR GARDGYGFDYWGQGTLVTVLA (SEQ ID NO:4); a hinge domain (or GGGGSGG GGSGGGGSGA (SEQ ID NO:5), a $V_L$ domain (or PSYVLTQPPSASGTPGQRV TISCSGGSSNIGSNAVSWYQQLPGTAPKLLIFTNDQRPSGVPDRFSGSKSGT SAPLAISGLQSEDESDYYCATWDDSLNGWVFGGGTKVTVRS (SEQ ID NO:6); and, an Apo B LDL-receptor binding domain (or DSSVIDALQYKLEGTTRLTRKR GLKLATALSLSNKFVEGS (SEQ ID NO:8).

In alternative embodiments, the antibody used to practice the compositions and methods as provided herein is a truncated version of the so-called exemplary single chain antibody s3RTV5-apoB, e.g., lacking an amino terminal CD5 secretory signaling sequence or an Apo B LDL-receptor binding domain, or lacking both. In alternative embodiments, an antibody used to practice the compositions and methods as provided herein is simply, or alternatively comprises or consists of, the $V_H$ domain, hinge region and $V_L$ domain, e.g., SEQ ID NO:4, SEQ ID NO:5 and SEQ ID NO:6. For example, in one embodiment, an antibody used to practice the compositions and methods as provided herein comprises or consists of an amino acid sequence as set forth in (SEQ ID NO:9), including a $V_H$ domain, hinge region and $V_L$ domain, where the hinge region is underlined separating the $V_H$ domain amino terminal to the $V_L$ domain (SEQ ID NO:9):

```
MEQVNLRESGAEVKKPGASVKVSCKVSGYTFTGYYMHWVRQAPGQGLEW

MGWINSNSGATKYAQKFQGRVTMTRDTSITTAYMELSSLRSDDTAVYYC

ARGARDGYGFDYWGQGTLVTVLAGGGGSGGGGSGGGGSGAPSYVLTQPP

SASGTPGQRVTISCSGGSSNIGSNAVSWYQQLPGTAPKLLIFTNDQRPS

GVPDRFSGSKSGTSAPLAISGLQSEDESDYYCATWDDSLNGWVFGGGTK

VTVRS
```

In alternative embodiments, the nucleic acid sequence encoding the exemplary 3RTau scFV without the ApoB LDL-R binding domain (blood brain barrier- (BBB-) transport domain) is (SEQ ID NO:10):

```
ATGGAGCAGGTCAACTTAAGGGAGTCTGGGGCCGAGGTGAAGAAGCCTG

GGGCCTCAGTAAAGGTCTCCTGCAAGGTTTCTGGATACACCTTCACCGG

CTACTATATGCACTGGGTGCGACAGGCCCCTGGACAAGGACTTGAGTGG

ATGGGATGGATCAACTCTAACAGTGGTGCCACAAAGTATGCACAGAAGT

TTCAGGGCAGGGTCACCATGACCAGGGACACGTCCATCACCACAGCCTA

CATGGAGTTGAGCAGCCTGAGATCTGACGACACGGCCGTGTATTACTGT

GCGAGAGGTGCGAGAGATGGCTACGGATTTGACTACTGGGGCCAGGGAA

CCCTGGTCACCGTCTTGGCCGGTGGCGGTGGCAGCGGCGGTGGTGGGTC

CGGTGGCGGCGGATCTGGCGCGCCATCCTATGTGCTGACTCAGCCACCC

TCAGCGTCTGGGACCCCCGGGCAGAGGGTCACCATCTCTTGTTCTGGAG

GCAGCTCCAACATCGGAAGTAATGCTGTAAGCTGGTACCAGCAGCTCCC

AGGAACGGCCCCCAAACTCCTCATCTTTACTAATGATCAGCGGCCCTCA

GGGGTCCCTGACCGATTCTCTGGCTCCAAGTCTGGCACCTCAGCCCCCC

TGGCCATCAGTGGGCTCCAGTCAGAGGATGAGTCTGATTATTACTGTGC
```

-continued

AACATGGGATGACAGCCTGAATGGTTGGGTGTTCGGCGGAGGGACCAAG

GTCACCGTCCGATCA

In alternative embodiments, an antibody used to practice the compositions and methods as provided herein comprises or consists of an amino acid sequence encoded by a nucleic acid comprising a sequence as set forth in (SEQ ID NO:10).

In alternative embodiments, an antibody used to practice the compositions and methods as provided herein comprises or consists of an antigen binding site, or Complement Determining Regions (CDRs), capable of binding to an epitope comprising or consisting of the amino acid sequence DAGLKAEEAGIGDTPSLED EAAG (SEQ ID NO:11). The epitope was identified by studying the interaction between scFv and tau isoform 352 (tau352) by NMR spectroscopy. To identify the epitope, tau352 and the exemplary 3RT antibody were recombinantly expressed in E. coli and HEK293 cells, respectively. 2D $^1$H-$^{15}$N heteronuclear single quantum coherence (HSQC) spectra were recorded on tau352 in absence and presence of 3RT antibody, see FIG. 10A-C. The HSQC of tau352 has a narrow chemical shift dispersion indicative of an intrinsically disordered protein. The addition of 3RT antibody at an approximately equimolar ratio lead to the appearance of several new peaks with no changes in chemical shifts of the remaining signals in the tau352 spectrum, suggesting strong antibody binding. Furthermore, the presence of the 3RT scFv resulted in the attenuation of signal intensity for resonances of residues 40-62, caused by the increase in molecular weight upon 3RT scFv binding. Thus, suggesting that the stretch of 23 amino acids (SEQ ID NO:11) form a linear epitope, which is recognized by the 3RT antibody.

In alternative aspects, an antibody used to practice the compositions and methods as provided herein can comprise any peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. In alternative aspects, an antibody for practicing the invention includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

In alternative embodiments, an antibody used to practice the compositions and methods as provided herein is a "humanized" antibody or forms of non-human (e.g., murine) antibodies that are chimeric antibodies comprising minimal sequence (e.g., the antigen binding fragment) derived from non-human immunoglobulin. In alternative embodiments, humanized antibodies are human immunoglobulins in which residues from a hypervariable region (HVR) of a recipient (e.g., a human antibody sequence) are replaced by residues from a hypervariable region (HVR) of a non-human species (donor antibody) such as mouse, rat, rabbit or nonhuman primate having the desired specificity, affinity, and capacity. In alternative embodiments, framework region (FR) residues of the human immunoglobulin are replaced by corresponding non-human residues to improve antigen binding affinity.

In alternative embodiments, humanized antibodies may comprise residues that are not found in the recipient antibody or the donor antibody. These modifications may be made to improve antibody affinity or functional activity. In alternative embodiments, the humanized antibody can comprise substantially all of or at least one, and typically two, variable domains, in which all or substantially all of the hypervariable regions correspond to those of a non-human immunoglobulin and all or substantially all of Ab framework regions are those of a human immunoglobulin sequence.

In alternative embodiments, a humanized antibody used to practice embodiments provided herein can comprise at least a portion of an immunoglobulin constant region (Fc), typically that of or derived from a human immunoglobulin. However, in alternative embodiments, completely human antibodies also can be used to embodiments provided herein, including human antibodies comprising amino acid sequence which corresponds to that of an antibody produced by a human. This alternative, exemplary definition of a human antibody specifically excludes a humanized antibody comprising non-human antigen binding residues.

In alternative embodiments, an antibody used to practice the compositions and methods as provided herein comprises an "affinity matured" antibody, e.g., antibodies comprising with one or more alterations in one or more hypervariable regions which result in an improvement in the affinity of the antibody for antigen; e.g., 3-repeat (3R) Tau polypeptide, compared to a parent antibody which does not possess those alteration(s). In alternative embodiments, an antibody used to practice the compositions and methods as provided herein is a matured antibody having nanomolar or even picomolar affinities for the target antigen, e.g., 3-repeat (3R) Tau polypeptide. Affinity matured antibodies can be produced by procedures known in the art.

BBB-, CNS- or Brain Penetrating Moieties

In alternative embodiments, provided are single chain antibodies modified by the addition of a blood brain barrier- (BBB-), central nervous system- (CNS-) or brain-penetrating moiety, e.g., a fragment of the apoB protein, e.g., to facilitate trafficking into the CNS or brain. In alternative embodiments, any BBB-, CNS- or brain-penetrating moiety can be used in place of or in addition to an Apo B LDL-receptor binding domain or equivalent, e.g., SEQ ID NO:8.

In alternative embodiments, antibodies as provided herein, e.g., antibodies capable of targeting 3-repeat (3R) Tau polypeptide, are delivered to the brain by loading them into BBB-, CNS- or brain-penetrating particles, e.g., BBB-, CNS- or brain-penetrating nanoparticles, e.g., angiopep-conjugated poly(ethylene glycol)-copoly(ε-caprolactone) nanoparticles, as described e.g., in Saraiva et al, J. of Controlled Release vol 235:34-47 (2016); or as described in U.S. Pat. Nos. 9,657,094; 9,655,848 (describing a liposome with a specific BBB recognition peptide AHRERMS (SEQ ID NO:12) or ARERMS (SEQ ID NO:13); U.S. Pat. No. 9,642,803 (describing multi-headed amphiphilic compounds); U.S. Pat. No. 9,629,801 (describing a BBB-selective, BBB-targeting antibody); U.S. Pat. No. 9,611,323 (describing antibodies that bind blood brain barrier receptors (BBB-R)); U.S. Pat. No. 9,597,408 (describing peptide-mediated non-covalent delivery of active agents across the BBB); U.S. Pat. No. 9,475,840 (describing protease-resistant compounds useful as shuttles through the blood-brain barrier); U.S. Pat. Nos. 8,142,781, 8,124,095 and 8,053,569 (describing compositions for the transport of agents across the blood brain barrier).

In alternative embodiments, the particles or nanoparticles can be comprised of polymeric materials such as poly(ethylenimine) (PEI), poly(alkylcyanoacrylates), poly(amidoamine) dendrimers (PAMAM), poly(ε-caprolactone) (PCL), poly(lactic-co-glycolic acid) (PLGA), polyesters (poly(lactic acid) (PLA), or from inorganic materials such as gold, silicon dioxide (silica), or using natural polymers, such as polysaccharides (chitosan and alginate), amino acids (poly(lysine), poly(aspartic acid) (PASA)), or proteins (gelatin and albumin) and equivalents. In alternative embodiments, the particles or nanoparticles are functionalized with a blood brain barrier- (BBB-), central nervous system- (CNS-) or brain-penetrating moiety, e.g., a BBB-, CNS- or brain-penetrating fragment of an apoB protein, a targeting ligand for an insulin receptor or a glucose transporter, or transferrin polypeptide or targeting ligands such ligands for transferrin receptor, e.g., transferrin peptide, transferrin protein or antibody against transferrin, or a specific BBB recognition peptide such as AHRERMS (SEQ ID NO:12) or ARERMS (SEQ ID NO:13).

In alternative embodiments, the particles or nanoparticles are functionalized with a surfactant such as poly(sorbate 80) (also known as Tween 80™) or equivalents that can adsorb apolipoprotein E and/or A-I; the surfactant allows the anchoring of apolipoproteins whose interaction with lipoprotein receptors expressed in the brain endothelium enables the crossing of the BBB.

Specific transporters for glucose or for large amino acids such as tryptophan also can be used to cross the BBB. Cationized albumin or the OX26 monoclonal antibody to the transferrin receptor also can be used to cross the BBB by absorptive-mediated and receptor-mediated transcytosis, respectively. Cationized monoclonal antibodies also can be used to cross the BBB. Antibodies that bind brain (BBB) endothelial cell receptors resulting in endocytosis/transcytosis of the receptor and a bound ligand, such as a composition (including pharmaceuticals and formulations) used to practice embodiment provided herein, are also described e.g. in U.S. Pat. App. Pub. No. 20080019984.

For example, in one aspect, crossing the blood-brain barrier (BBB) can be accomplished by incorporating BBB protein transport peptides: such as the pentapeptide AAEAP, as described e.g. in U.S. Pat. App. Pub. No. 20080213185; or polypeptides comprising at least 10% basic amino acid residues such as arginine or lysine that have brain-localizing activity as described e.g. in U.S. Pat. App. Pub. No. 20080199436.

Ubiquinone analogs and reduced ubiquinone (ubiquinol) analogs also can be used to cross the BBB as described e.g. in U.S. Pat. App. Pub. No. 20070203080.

Another alternative embodiment encompasses an artificial low-density lipoprotein (LDL) carrier system for the targeted delivery therapeutic agents across the BBB, e.g., using artificial LDL particles comprising various lipid elements such as phosphatidyl choline, fatty-acyl-cholesterol esters, and apolipoproteins as described e.g., in U.S. Pat. App. Pub. Nos. 20080160094; 20070292413; 20070264351. Artificial low-density lipoprotein particles can facilitate transport of therapeutic agents across the BBB by transcytosis. The BBB contains type II scavenger receptors which bind LDL with high affinity. For example, one embodiment comprises use of an artificial LDL particle comprising an outer phospholipid monolayer and a solid lipid core, where the outer phospholipid monolayer comprises at least one apolipoprotein and the solid lipid core contains at least one therapeutic agent.

Synthetic polymers such as a poly(butyl cyanoacrylate) or a polyacrylamide covered with a polysorbate (e.g., POLYSORBATE 80) can be used because these particles are sufficiently hydrophilic to be water-soluble, yet are able to maintain their structural form for long periods, which protects the therapeutic agent from uptake into the liver and kidney where it is subject to natural detoxification process.

Another alternative embodiment encompasses use of synthetic poly(butyl cyanoacrylate) particles to which ApoE molecules are covalently bound. The surface of the particles are further modified by surfactants or covalent attachment of hydrophilic polymers, see e.g., U.S. Pat. No. 6,288,040.

We demonstrated that once in the CNS these antibodies, e.g., scAbs, which can specifically bind a 3-repeat (3R) Tau polypeptide and not specifically recognizing or binding to a 4R Tau polypeptide, reduced the accumulation of 3R Tau and related deficits in a transgenic mouse models of taupathy and Picks's Disease; and these data demonstrate that scAbs provided herein are effective for the treatment, amelioration, prevention or reduction of symptoms, of neurodegenerative disorders and conditions, including taupathies such as Alzheimer's Disease (AD), Pick's Disease (PiD) and Fronto-temporal lobar degeneration (FTLD), or any disorder or condition associated with a 3R Tau accumulation.

Nanoparticles and Liposomes

In alternative embodiments, provided are nanoparticles and liposomal membranes comprising compounds as provided herein, wherein the nanoparticles and liposomal membranes can target specific molecules, including biologic molecules, such as polypeptides, including cell surface polypeptides, e.g., for targeting the CNS. Thus, in alternative embodiments, provided are nanoparticles and liposomal membranes targeting brain or neuronal cells.

In alternative embodiments, provided are nanoparticles and liposomal membranes comprising (in addition to comprising antibodies as provided herein) molecules, e.g., peptides or antibodies, that selectively target neurons in the brain. In one aspect, the compositions used to practice this invention are specifically designed to cross the blood-brain barrier (BBB).

In alternative embodiments, provided are nanocells to allow the sequential delivery of two different therapeutic agents with different modes of action or different pharmacokinetics, at least one of which comprises a composition of this invention. A nanocell is formed by encapsulating a nanocore with a first agent inside a lipid vesicle containing a second agent; see, e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to patients. For example, one agent can be contained in the outer lipid vesicle of the nanocell, and another agent can be loaded into the nanocore. This arrangement allows the one agent to be released first.

In alternative embodiments, provided are multilayered liposomes comprising compounds as provided herein, e.g., for transdermal absorption, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition of this invention.

A multilayered liposome as provided herein may further include an antiseptic, an antioxidant, a stabilizer, a thickener, and the like to improve stability. Synthetic and natural antiseptics can be used, e.g., in an amount of 0.01% to 20%. Antioxidants can be used, e.g., BHT, erysorbate, tocopherol, astaxanthin, vegetable flavonoid, and derivatives thereof, or a plant-derived antioxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharide or an oligosaccharide, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as acacia gum, xanthan gum, gellan gum, locust bean gum and starch, cellulose derivatives, such as hydroxy ethylcellulose, hydroxypropyl cellulose and carboxymethyl cellulose, synthetic polymers, such as polyacrylic acid, poly-acrylamide or polyvinylpyrollidone and polyvinylalcohol, and copolymers thereof or cross-linked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

In one embodiment, liposome compositions comprising substituted ammonium and/or polyanions are used, particularly for targeting delivery of a compound used to practice this invention to the brain, as described, e.g., in U.S. Pat. Pub. No. 20070110798.

Also provided herein are nanoparticles in the form of drug-containing nanoparticles (e.g., a secondary nanoparticle), as described, e.g., in U.S. Pat. Pub. No. 20070077286. In one embodiment, the invention provides nanoparticles comprising a fat-soluble drug of this invention or a fat-solubilized water-soluble drug to act with a bivalent or trivalent metal salt.

Products of Manufacture and Kits

Provided are products of manufacture and kits comprising a pharmaceutical composition, a nanoparticle, a particle, a liposome or a micelle, or an implant as provided herein, or a recombinant or synthetic single chain antibody (scAb) as provided herein.

Pharmaceutical Compositions

The invention provides pharmaceutical compositions and methods for the treatment, amelioration, prevention or reduction of symptoms, of a neurodegenerative disorder or a condition, comprising administering to an individual in need thereof an antibody that specifically targets, or specifically binds to, a 3-repeat (3R) Tau polypeptide and does not specifically recognize or bind to a 4-repeat (4R) Tau polypeptide.

In alternative embodiments, antibodies used to practice compositions and methods as provided herein, including single chain or humanized antibodies, or including antibodies that specifically target, or specifically binds to, a 3-repeat (3R) Tau polypeptide, are formulated with a pharmaceutically acceptable carrier. In alternative embodiments, the pharmaceutical compositions used to practice the invention can be administered parenterally, topically, orally or by local administration, such as by aerosol or transdermally. The pharmaceutical compositions used to practice the invention can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents used to practice compositions and methods as provided herein, including antibodies, can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions used to practice compositions and methods as provided herein, including antibodies, include those suitable for oral/nasal, topical, parenteral, rectal, and/or intravaginal administration. The formulations may conveniently be presented in unit dosage form and may be prepared by any methods well known in the art of pharmacy. The amount of active ingredient (including antibodies as provided herein) which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations used to practice the invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

In alternative embodiments, aqueous suspensions comprising antibodies used to practice this invention are in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Alternative embodiments, the pharmaceutical compounds can be parenterally administered, such as by intrathecal or intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1, 3-butanediol. The administration can be by bolus or continuous infusion (e.g., substantially uninterrupted introduction into a blood vessel for a specified period of time).

The pharmaceutical compounds and formulations used to embodiments provided herein can be lyophilized. A stable lyophilized formulation comprising an antibody-comprising composition as provided herein can be made by lyophilizing a solution comprising as antibody as provided herein and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations as provided herein can be delivered by the use of liposomes. By using liposomes, particularly where the liposome surface carries ligands specific for target cells, or are otherwise preferentially directed to a specific organ, e.g., the brain, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The methods and uses as provided herein can further comprise co-administration with other drugs or pharmaceuticals, e.g., compositions for treating conditions, infections, pathology and/or inflammation in the CNS (e.g., brain), or a taupathy or any disorder or condition associated with a 3R Tau accumulation, for example where the taupathy is Alzheimer's Disease (AD), Pick's Disease (PiD) or Fronto-temporal lobar degeneration (FTLD).

Therapeutically Effective Amounts

The pharmaceuticals and formulations as provided herein can be administered for prophylactic and/or therapeutic treatments. In therapeutic applications, compositions are administered to a subject already suffering from a condition, infection or disease in an amount sufficient to cure, alleviate, reverse or partially arrest the clinical manifestations of the condition, infection, pathology or disease and its complications (a "therapeutically effective amount"). For example, in alternative embodiments, pharmaceutical compositions and formulations used to practice the invention are administered in an amount sufficient to treat, prevent, reverse and/or ameliorate a taupathy or any disorder or condition associated with a 3R Tau accumulation, for example where the taupathy is Alzheimer's Disease (AD), Pick's Disease (PiD) or Fronto-temporal lobar degeneration (FTLD).

The amount of pharmaceutical composition adequate to accomplish a therapeutic effect is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra).

The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

For determining and/or optimizing the therapeutically effective amount of a composition used to practice this invention, the clinician can use any diagnostic or evaluation method or technique to determine improvement in the patient, e.g., that administering a composition used to practice this invention to an individual is effective to prevent, treat and/or ameliorate a taupathy or any disorder or condition associated with a 3R Tau accumulation, for example where the taupathy is Alzheimer's Disease (AD), Pick's Disease (PiD) or Fronto-temporal lobar degeneration (FTLD). In alternative embodiments, a method of the invention is effective if it ameliorates, e.g., improves in any detectable or quantifiable way, or slows the progression or beginning of, or decreases in any measurable or assessable way any symptom or effect, or reverses in any measurable or assessable way any symptom or effect caused by the taupathy. For example, cognitive, learning or memory impairments resulting from the taupathy can be diagnosed and/or assessed (e.g., determining the progress, regression and/or severity of) by the clinician using DSM-IV or DSM-IV-TR editions (e.g., using the latest American Psychiatric Association) criteria.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1: Exemplary Methods and Compositions Using Single Chain Antibodies (scAbs) that Target 3-Repeat (3R) Tau are Effective for the Treatment of Neurodegenerative Disorders This example demonstrates that methods and compositions as provided herein using single chain antibodies (scAbs) that target or specifically bind to 3-repeat (3R) Tau are effective for the treatment of neurodegenerative disorders and conditions involving taupathies such as Alzheimer's Disease (AD), Pick's Disease (PiD) and Fronto-temporal lobar degeneration (FTLD), or any disorder or condition associated with a 3R Tau accumulation.

Rationale for the Development of Brain Penetrating Single Chain Antibodies Against 3R Tau for the Treatment of AD and PiD.

Figure 1:
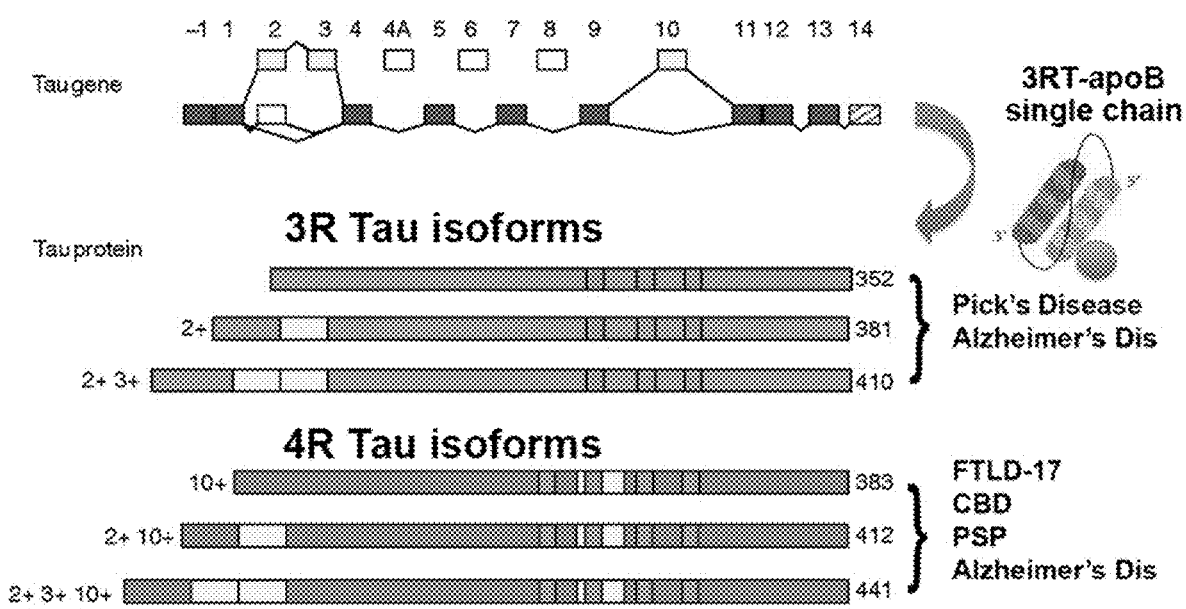
FIG. 1 is a schematic representation of various tau isoforms (alternative spliced forms) with 3R and 4R microtubule binding; the single chain antibodies provided herein target the 3RTau with relevance to the treatment of a neurodegenerative disorder or condition, including taupathies such as Alzheimer's Disease (AD), Pick's Disease (PiD) and Fronto-temporal lobar degeneration (FTLD), or any disorder or condition associated with a 3R Tau accumulation, as further discussed in Example 1, below.

Our approach is different in that instead of targeting total Tau, 4R Tau or phosphorylated species we are targeting specifically 3R Tau which is relevant to the pathogenesis of AD, PiD and other unusual taupathies (FIG. 1). While others have used active vaccination with peptides that elicit antibodies against various Tau species or with monoclonal antibodies against 4R Tau or phosphorylated Tau species that display low or variable degrees of CNS trafficking we chose to develop single chain antibodies selectively targeting 3R Tau fused with a fragment of LDL-R binding protein (apoB) that enhances brain penetration (FIG. 1). The advantage of using single chain antibodies against 3R Tau is that they have greater selectivity and higher affinity and since they lack Fc they are less prone to elicit inflammatory or undesired immunological reactions. We used as proof-of principle the lentiviral vector to express the 3R Tau-apoB in neuronal cells in culture or from the liver for constant expression into the blood in animal models. Also provided are methods comprising the production of a recombinant 3R Tau-apoB protein for direct infusion into the bloodstream to generate a more clinically feasible treatment for patients with AD, PiD and other taupathies.

Figure 2A:
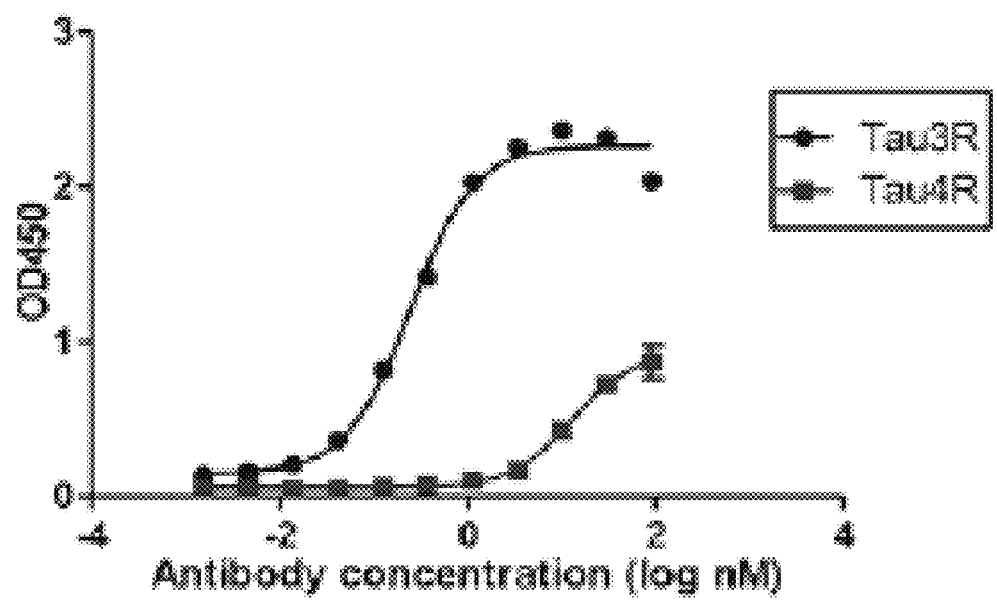
FIG. 2A-F graphically (FIG. 2A) and schematically (FIG. 2B-F) illustrate data showing that the 3RT single chain antibody (Clone 5F10) selectively recognizes 3R Tau and not 4R Tau in an ELISA assay (FIG. 2A) and by immunoblot (FIG. 2B, exposure time 3 minutes (min.)
Figure 2B:
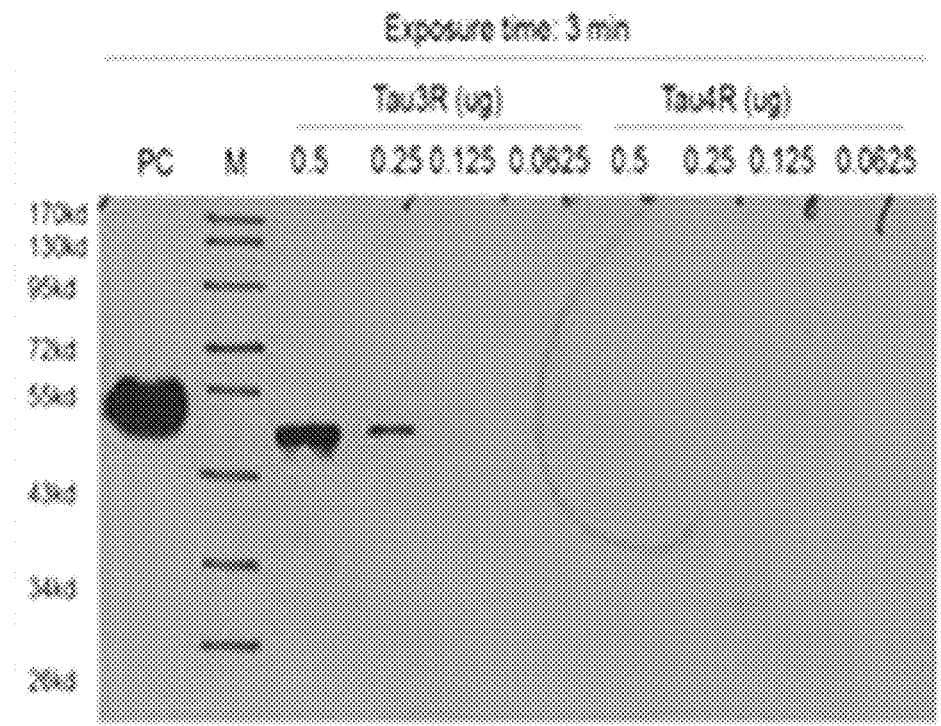
Figure 2C:
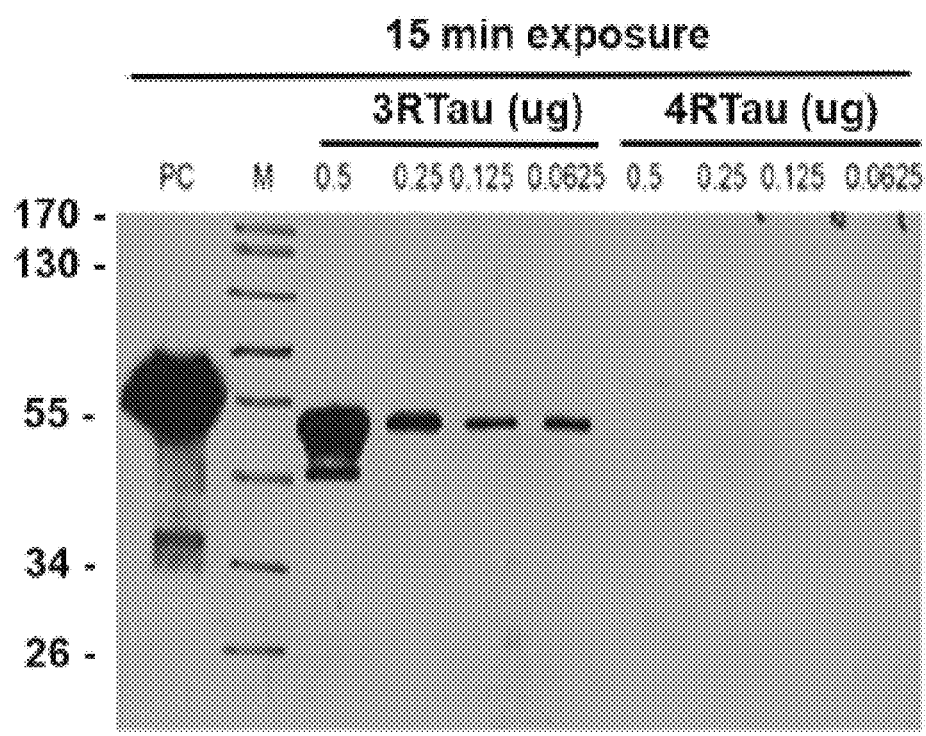
Figure 2D:
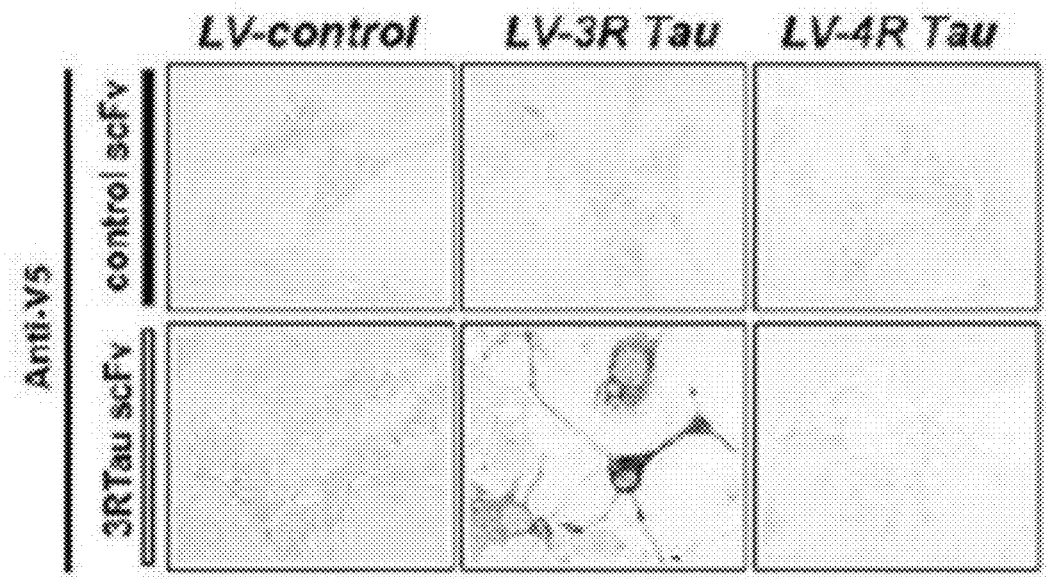

Development of Single Chain Antibodies that Selectively Recognize 3R Tau In Vitro and in Tissues from Patients with AD and PiD We have recently developed FaB antibody fragments that targeted specifically (or specifically bound to) the 3R Tau that does not recognize the 4R Tau. Full length 3R Tau and 4R Tau protein were expressed and purified for screening of a large phage display single chain antibody library. The phage display single chain library was positively screened over immobilized 3RT protein while negatively screened over immobilized 4R Tau protein multiple times until 5 clones were isolated were isolated that appeared to bind selectively to the 3R Tau protein. These 5 clones were further characterized and by ELISA binding efficiency and narrowed down to a single clone (clone 5F10) that showed selective binding to the 3R Tau protein with little to no cross-reactivity to the 4R Tau protein (FIG. 2A).

To confirm that the single chain antibodies selectively binds to 3R Tau immunoblot and ELISA was performed (FIG. 2). ELISA with bound 3R Tau or 4R Tau protein and increasing concentrations of the 3RT scFV antibody show significant selectivity for the 3R Tau protein at lower concentration of antibodies (FIG. 2A). In fact, in the micromolar and nanomolar concentrations of antibody, the 3RT scFV only binds to the 3R Tau protein with little to no detectable binding to the 4R Tau protein (FIG. 2A). Immunoblot analysis (FIG. 2B, 2C) confirmed the specific and sensitivity of the 3RT scFV antibody. 2-fold dilutions of 3R Tau and 4R Tau recombinant protein were loaded onto a gel and probed with the 3RT scFV antibody. The 3RT scFV antibody detected nanogram quantity of 3R Tau protein with no detectable cross-reactivity of the 4R Tau protein. Thus, the 3RT scFV antibody is specific and sensitive for the 3R Tau protein with little to no detectable cross-reactivity for the very similar 4R Tau protein (FIG. 2). Next the single chain antibodies were used to stain sections from PiD patients and 3RTau tg mice. Compared to the control single chain the 3RT scFV immunoreacted with neuronal cells only in the PiD and 3RTau tg mice. No immunoreactivity was detected in control human brain or non-tg mice (see FIG. 2D-F).
Construction of Viral Vector Expressing the Recombinant 3RT Single Chain Antibody with Brain Penetrating Sequence for Proof-Of Concept Studies.

Figure 3:
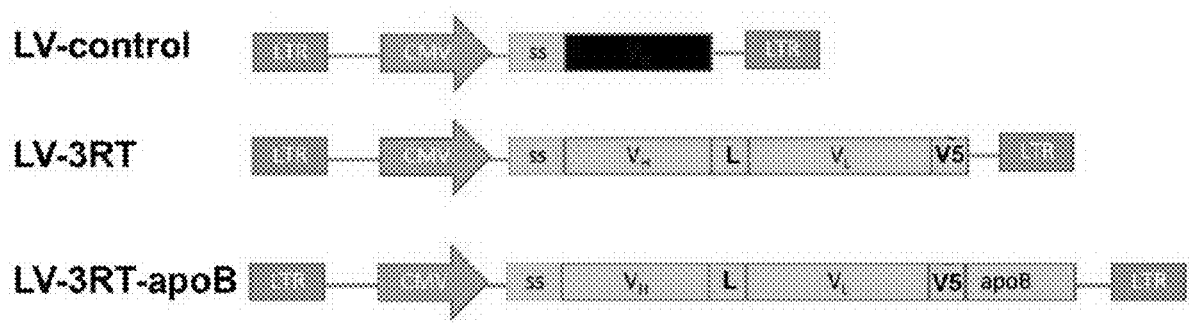
FIG. 3 is a schematic—diagrammatic representation of viral vectors used for recombinant protein production for proof of concept experiments: Lentivector diagram with (LTR) long terminal repeat, (CMV) human cytomegalovirus promoter and antibody construct. ss—secretory signal sequence, VH—Variable domain heavy, L—linker region, VL—Variable domain light, 5—V5 epitope tag, apoB—LDLR binding domain of Apolipoprotein B. LV-s3RTV5-apoB is similar without the apoB sequence at the 3' end, as further discussed in Example 1, below.

This antibody, designated 3RT, is expressed as a single chain antibody allowing to be expressed from a viral vector or easily genetically manipulated for further alterations. For in vitro and in vivo proof of concept experiments 3 lentiviral vectors (LV) were prepared, namely—LV-control (empty vector), LV-3RT (expressing the single chain antibody alone) and LV-3RT-apoB (expressing the single chain antibody with ApoB) (FIG. 3). The use of the single chain antibody allows for increased brain penetration over full size monoclonal antibodies; however, to further increase the penetration of the 3R Tau antibody to the CNS, we have added a blood-brain transport peptide designated apoB.

We previously showed the 38 amino acid LDL-receptor binding domain from Apolipoprotein B when fused to a cargo protein is sufficient to transport proteins across the blood-brain barrier to the neuronal side {Spencer, 2014 #926; Spencer, 2011 #511; Spencer, 2015 #1032; Spencer, 2014 #916; Spencer, 2007 #61}. To increase the penetration of the 3RT anti-3R Tau scFV antibody, we fused the apoB 38 amino acid peptide to the C-terminus. A V5 tag was added for easer detection. Finally, a secretory signal sequence was added to the 5' end of the full protein to allow for secretion of the protein from expressing cells (FIG. 4, 5). This gene and the similar gene coding for the antibody lacking the apoB transport tag (FIG. 4, 5) were cloned into the lentivirus vector for expression (FIG. 3) {Tiscornia, 2006 #294}. These vectors allows the production of the single chain antibodies directly in the infected parent cells or by infecting intermediate cells and utilizing the single chain antibody from the conditioned media. To confirm the expression of the single chain 3RT and 3RT-apoB from the LV vectors, neuronal cell lines were platted in coverslips and immunostained with an antibody against V5 (FIG. 6). Cell infected with LV-bobi were negative while cells infected with LV-3RT and 3RT-apoB displayed strong V5 immunoreactivity in over 90% of the cells (FIG. 6).
The 3RT-apoB Retains Activity and Reduces the Accumulation of 3R Tau in an In Vitro Model of Cell to Cell Transmission To examine the ability of the 3RT antibody to reduce the accumulation of 3RTau in an in vitro neuronal model, we co-infected B103 neuronal cells with a lentivirus vector over-expressing 3RTau along with a lentivirus vector expressing either the 3RT alone (LV-s3RTV5) or with the apoB BBB transport tag (LV-s3RTV5-apoB). A control virus was included (LV-Bobi). Both scFv coding vectors expressed equivalent amounts of the 3RT scFV and were able to reduce the accumulation of 3RTau in the neuronal cells. The control vector (LV-Bobi) did not appear to have an effect on the neuronal accumulation of 3RTau (FIG. 7).

Figure 8A:
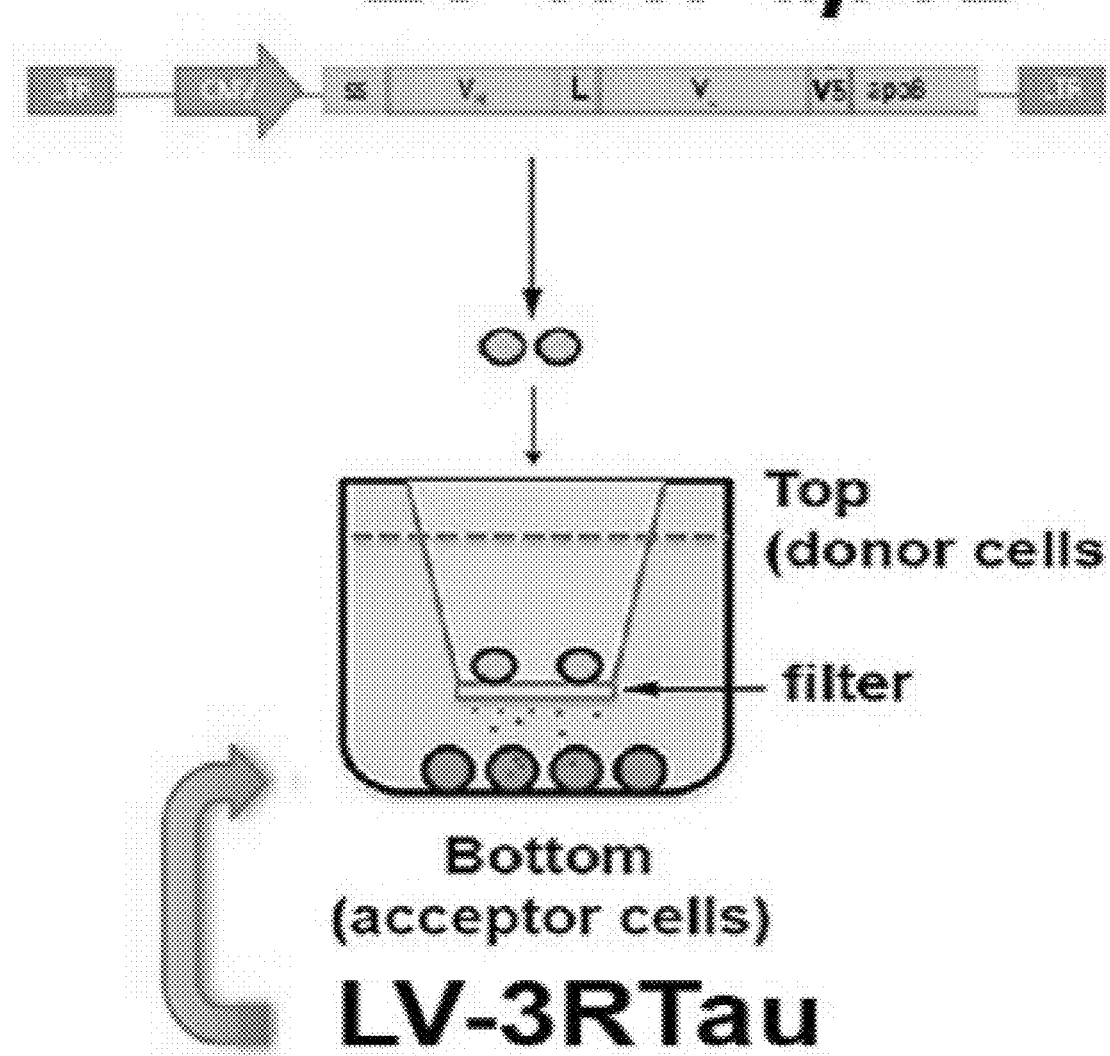
Figure 8B:
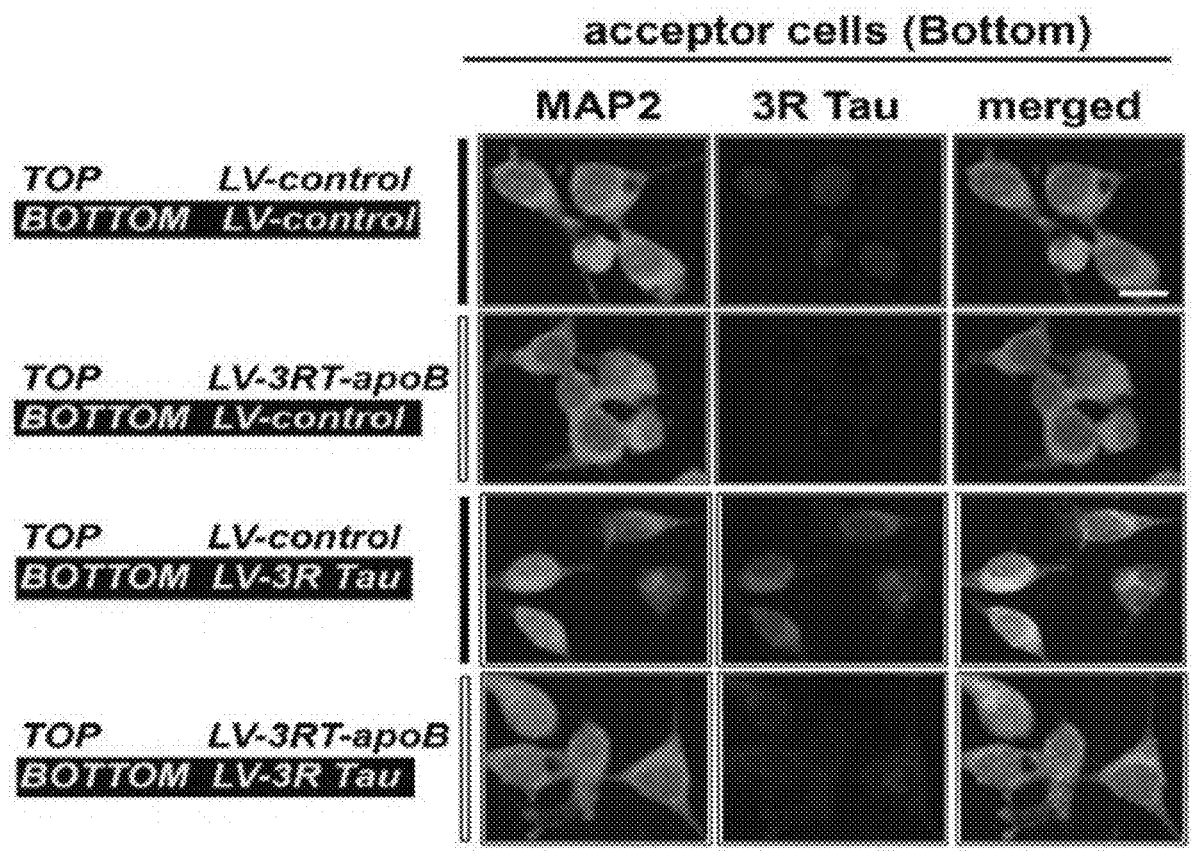
Figure 8C:
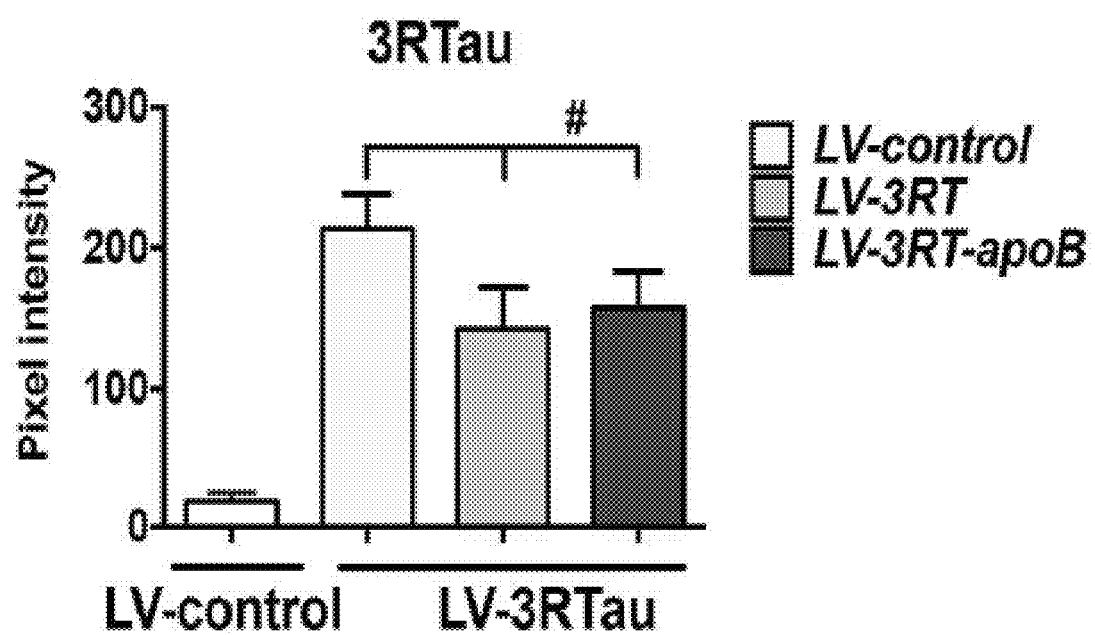

To examine the ability of the secreted 3RT scFv to reduce the accumulation of 3RTau in an in vitro neuronal model, we separated the 3RTau expressing cells from the 3RT expressing cells by a 0.4 μm membrane that allows only the passage of proteins but prevents the contact of the cells. The LV-s3RTV5, LV-s3RTV5-apoB and LV-Bobi lentivector expressing cells were cultured in the top chamber and the LV-3RTau expressing cells were cultured in the bottom chamber. Analysis of the cells in the lower chamber showed similar levels of uptake of the scFvs for LV-s3RTV5 and LV-s3RTV5-apoB infected cells. Both s3RTV5 and s3RTV5-apoB significantly reduced the accumulation of 3RTau similar to the co-infection experiment (FIG. 8A-B). Taken together, these studies these studies show that addition of the apoB BBB transport tag does not affect the activity or binding of the 3RT scFV for 3RTau and the virus vector expressed scFV 3RT is able to reduce the accumulation of 3RTau in neuronal cells.
The 3RT-apoB Penetrates into the CNS and Reduces the Accumulation of 3R Tau in a Transgenic Mouse Model of Tauopathy and Pick's Disease For these experiments we utilized a 3R Tau mutant transgenic mouse model developed in our laboratory. This mouse model of PiD and tauopathies over-expresses 3R Tau under the pan neuronal promoter-mThy1 (FIG. 9A) (Rockenstein et al, PLoS One. 2015) (FIG. 9A-G). The 3R Tau tg mice show abnormal accumulation of 3R Tau in the neocortex and limbic system with neurodegeneration, formation of PiD-like inclusions and behavioral deficits. Non-tg and 3R Tau tg mice receive IP injections of the LV-3RT-apoB or LV-control and after 4 weeks were evaluated behaviorally, biochemically and neuropathologically. Compared to non-tg mice treated with LV-control or LV-3RT, the LV-control and LV-3RT 3R Tau tg mice displayed memory deficits and hyperactivity.

In contrast, 3R tau tg mice treated with the brain penetrating LV-3RT-apoB displayed improvements and behavior comparable to the non-tg mice (FIG. 10A). At the end of the behavior, the brains were extracted and analyzed by immunoblot and immunocytochemistry. By western blot with an antibody against the V5 tag mice treated with LV-control or LV-3RT showed low or no V5 immunoreactivity, in contrast mice treated with LV-3RT-apoB displayed higher levels of V5 immunoreactivity in brain homogenates (FIG. 10B).

Next, brain sections were immunolabeled with antibodies against V5. Likewise, mice treated with LV-control or LV-3R Tau showed low or no V5 immunoreactivity, in contrast mice treated with LV-3R Tau-apoB displayed V5 immunoreactivity in neuronal cells in the neocortex and hippocampus (FIG. 10C). To evaluate the beneficial effects of the 3RT-apoB, brain sections were immunostained with antibodies against 3R Tau and the neuronal marker NeuN. This study showed that the highest levels of 3R Tau were detected in tg mice treated with the LV-control or LV-3RT (FIG. 10D). In contrast, tg mice treated with LV-3RT-apoB showed decreased levels of 3R Tau accumulation in neuronal cells in the neocortex and hippocampus. Likewise, while tg mice treated with LV-control or LV-3RT (FIG. 10D).

Example 2: Selective Targeting of 3 Repeat Tau with Brain Penetrating Single Chain Antibodies for the Treatment of Neurodegenerative Disorders This example demonstrates that methods and compositions as provided herein using single chain antibodies (scAbs) that target or specifically bind to 3-repeat (3R) Tau are effective for the treatment of neurodegenerative disorders and conditions involving taupathies such as Alzheimer's Disease (AD), Pick's Disease (PiD) and Fronto-temporal lobar degeneration (FTLD), or any disorder or condition associated with a 3R Tau accumulation.

Here, we developed a brain penetrating, single chain antibody that specifically recognize 3RTau. These single chain antibodies were modified by the addition of a fragment of the apoB protein to facilitate trafficking into the brain, once in the CNS these antibody fragments reduced the accumulation of 3RTau and related deficits in a transgenic mouse model of taupathy. NMR studies showed that the single chain antibody recognized an epitope in aa 40-62 of 3RTau. The 3RT antibody reduced 3RTau transmission and facilitated the clearance of tau via the endosomal-lysosomal pathway. Together, these results demonstrate that targeting 3RTau with highly specific brain penetrating, single chain antibodies can be used for the treatment of taupathies such as AD and PiD.

To date, there has been little or no effort to develop treatments specifically targeting the 3RTau. To address this gap in the field, for this study, we developed single chain (scFV) antibodies directed against 3RTau with little to no cross-reactivity for 4RTau. This scFV antibody was further modified by the addition of the LDL receptor-binding domain of apolipoprotein B (apoB), which enhances brain penetration (33-37). By NMR this scFV recognized an epitope between aa 40-62 of 3RTau. We found that this 3RTau specific scFV reduced 3RTau accumulation in a 3RTau transgenic (tg) mouse model of tauopathy and PiD (38) mice while also ameliorating the neuropathology and improving memory behavioral deficits. The development of scFV directed specifically against the 3RTau species of Tau may be a useful immunotherapeutic option for PiD, AD or other Tauopathies of the aging population.

Results

Development of Single Chain Antibody that Selectively Recognize 3RTau In Vitro and in Tissues from Patients with AD and PiD We have recently developed FaB antibody fragments that specifically targeted the 3RTau and does not recognize the 4RTau protein. Full length 3RTau and 4RTau protein were expressed and purified for screening of a large phage display scFv antibody library. The phage display scFv library was positively screened over immobilized 3RTau protein while negatively screened over immobilized 4RTau protein multiple times until 5 clones were isolated that bind selectively to the 3RTau protein. These 5 clones were further characterized by ELISA binding efficiency and narrowed down to a single clone that showed selective binding to the 3RTau protein with little to no cross-reactivity to the 4RTau protein.

To confirm that the scFv antibody selectively binds to 3RTau, immunoblot and ELISA were performed (FIG. 2A, B, C). ELISA with bound 3RTau or 4RTau protein and increasing concentrations of the 3RTau scFV (here after referred as 3RT) antibody showed significant selectivity for the 3RTau protein at femtomolar concentrations of antibody (FIG. 2A). Immunoblot analysis (FIG. 2B, 2C) confirmed the specificity and sensitivity of the 3RT (hereafter this abbreviation refers to the 3RTau single chain antibody) for 3RTau protein over the 4RTau protein. A 2-fold dilutions of 3RTau and 4RTau recombinant protein were loaded onto a gel and probed with the 3RT. The 3RT antibody detected nanogram quantity of 3RTau protein with no detectable cross-reactivity of the 4RTau protein. Thus, the 3RT antibody is specific and sensitive for the 3RTau protein with little to no detectable cross-reactivity for the very similar 4RTau protein.

Figure 2E:
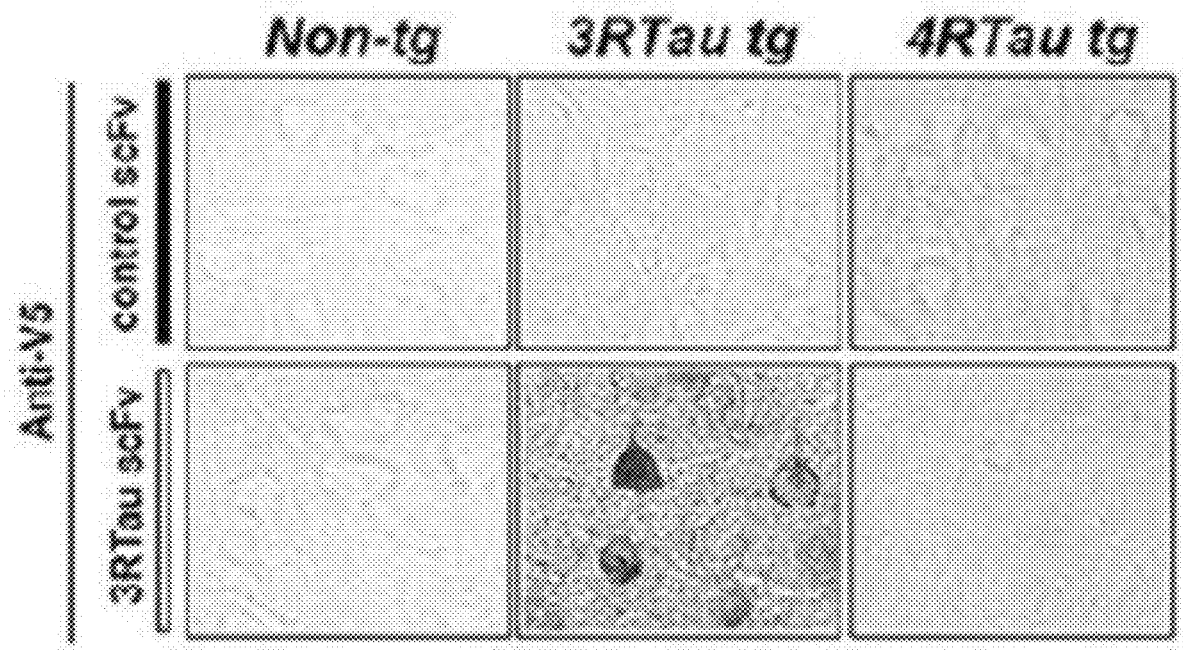
Figure 2F:
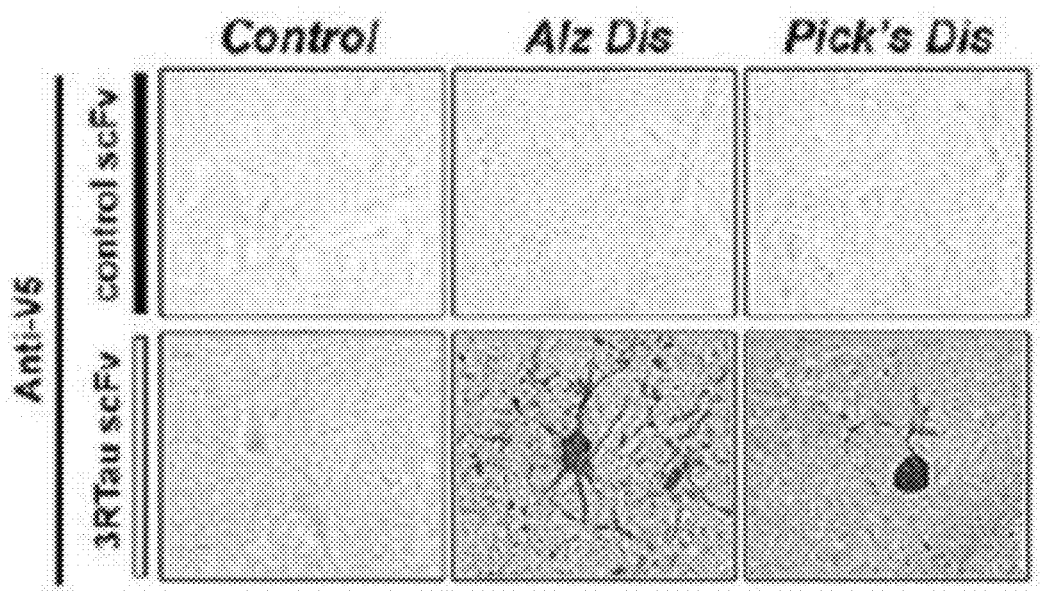

Next, the 3RT antibody was used for immunohistochemistry on in vitro mouse N2A neuronal cells infected with lentivirus overexpressing either 3RTau or 4RTau. Immunostaining with the 3RT antibody was restricted to the neurons overexpressing the 3RTau protein (FIG. 2D), while control mouse adult neurons that only express 4RTau were not labeled. The immunostaining specificity was further confirmed with sections from non-tg, 3RTau tg and 4RTau tg mice where immunoreactivity with the 3RT was observed only in 3RTau tg mice whereas the control scFV antibody showed no immunoreactivity in any of the sections (FIG. 2E). Finally, the 3RT antibody was tested with sections from the frontal cortex of AD, PiD and control patients. Compared to the control scFv, the 3RT antibody immunoreacted with neurofibrillary tangles in the AD and the Pick bodies in PiD cases, but no immunoreactivity was detected in control human brain (FIG. 2F).

NMR Investigation of scFv Binding to Tau352

The interaction between scFv and tau352 was further studied by NMR spectroscopy. For this purpose, tau352 and 3RT antibody were recombinantly expressed in $E.$ $coli$ and HEK293 cells, respectively. 2D $^1$H-$^{15}$N heteronuclear single quantum coherence (HSQC) spectra were recorded on tau352 in absence and presence of 3RT antibody (FIG. 10A). The HSQC of tau352 has a narrow chemical shift dispersion indicative of an intrinsically disordered protein (FIG. 10A). The addition of the exemplary 3RT single chain antibody at an approximately equimolar ratio lead to the appearance of several new peaks with no changes in chemical shifts of the remaining signals in the tau352 spectrum (FIG. 10A,B), suggesting strong antibody binding. Furthermore, the presence of 3RT scFv resulted in the attenuation of signal intensity for resonances of residues 40-62 (FIG. 10C), caused by the increase in molecular weight upon scFv binding. Thus, suggesting that the stretch of 23 amino acids form a linear epitope, which is recognized by the 3RT antibody.

Figure 11:
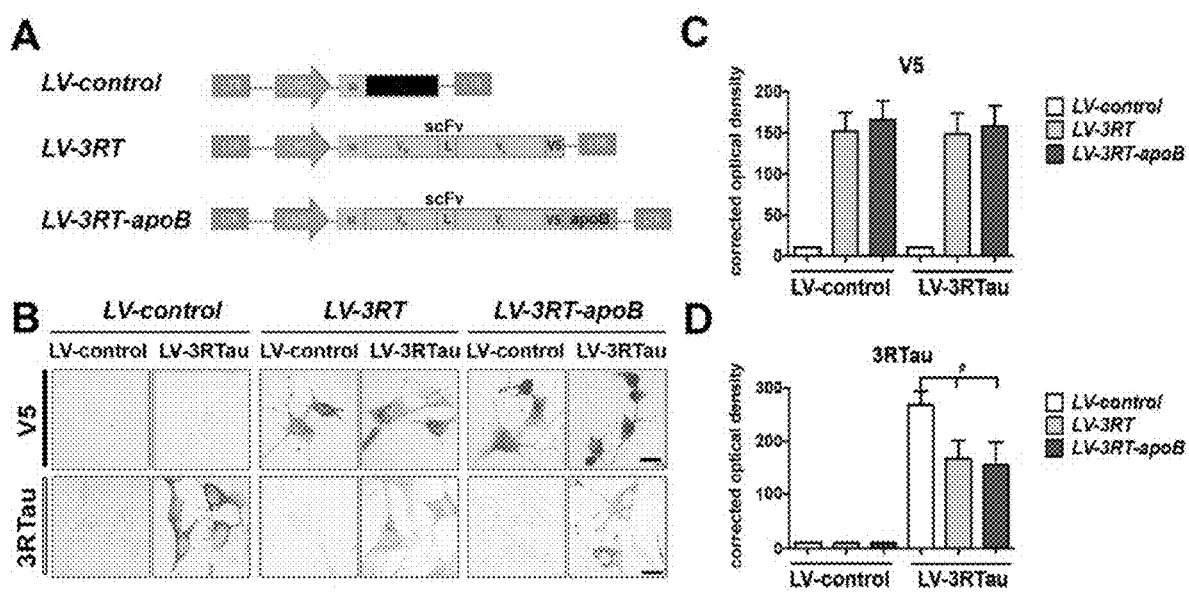

The 3RT-apoB Retains Activity and Reduces the Accumulation of 3RTau in an In Vitro Model of Cell to Cell Transmission For cell based proof-of concept studies, we first constructed a viral vector expressing the recombinant 3RT antibody with the brain penetrating sequence (apoB). For this purpose, the scFV cDNA, designated 3RT, was cloned and expressed in a lentiviral vector (LV) system as previously described (33, 39). Three LVs were prepared, namely—LV-control (empty vector), LV-3RT (expressing the single chain antibody alone) and LV-3RT-apoB (expressing the single chain antibody with ApoB) (FIG. 11A). The use of the scFv antibody allows for increased brain penetration over full size monoclonal antibodies; however, to further increase the BBB trafficking, permanence and cell penetration of the 3RT antibody in the CNS, we have added a peptide designated apoB. We previously showed the 38 amino acid LDL-receptor binding domain from apoB when fused to a cargo protein is sufficient to transport proteins across the blood-brain barrier to penetrate into neuronal side (33, 34, 36, 37, 40). We fused the apoB$^{38}$ peptide to the C-terminus along with a V5 epitope tag for easier detection. Finally, a secretory signal sequence was added to the 5' end of the full protein to allow for secretion of the protein from expressing cells (FIG. 11A).

To examine the ability of the 3RT antibody to reduce the accumulation of 3RTau in an in vitro neuronal model, we co-infected N2A neuronal cells with a LV over-expressing 3RTau along with either LV-control, LV-3RT or LV-3RT-apoB. As demonstrated by the detection of the V5 tag, both scFv coding vectors expressed equivalent amounts of the 3RT antibody (FIG. 11B,C) and were able to reduce the accumulation of 3RTau in the neuronal cells (FIG. 11B,D) to a comparable extent, indicating that the addition of the apoB fragment did not interfere with the antibody activity. In contrast, control vector (LV-control) did not appear to have an effect on the neuronal accumulation of 3RTau (FIG. 11B,D).

Figure 8D:
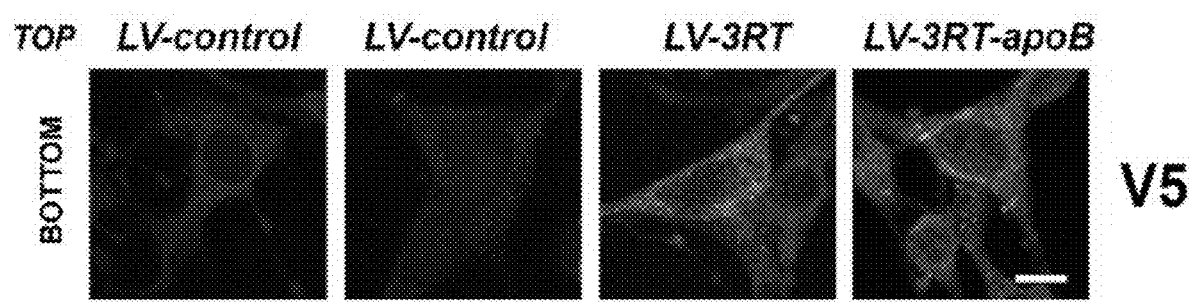
Figure 8E:
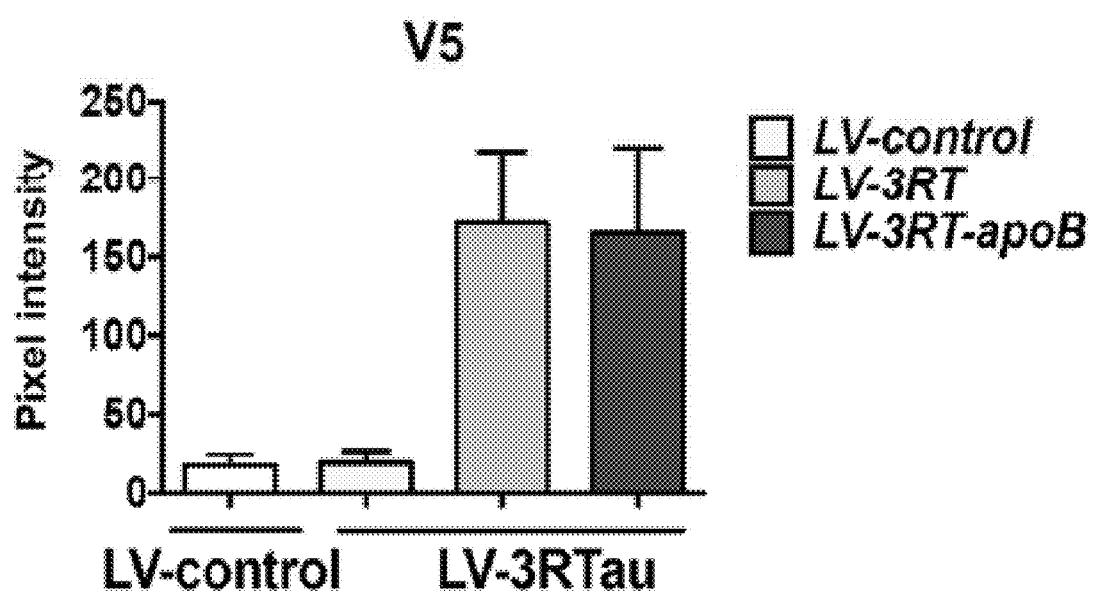

Next, to examine the ability of the secreted 3RT antibody (V5 tagged) to reduce the accumulation of 3RTau in an in vitro neuronal model, we separated the 3RTau expressing cells from the 3RT antibody expressing cells by a 0.4 µm membrane that allows only the passage of proteins but prevents the contact of the cells (FIG. 8A). The LV-3RT, LV-3RT-apoB and LV-control expressing cells were cultured in the top chamber (donor cells) and the LV-3RTau expressing cells were cultured in the bottom chamber (acceptor cells) (FIG. 8A). Compared to the LV-control, both the 3RT and 3RT-apoB antibodies produced by cells in the top of the chamber, reduced the accumulation of 3RTau in neuronal cells in the bottom of the chamber (FIG. 8B,C). Analysis of the cells in the lower chamber showed similar levels of uptake of the exemplary 3RT 3RT-apoB antibodies (FIG. 8D,E). Taken together, these two studies these studies show that addition of the apoB BBB transport tag does not affect the activity or binding of the 3RT antibody for 3RTau and the virus vector expressed 3RT is able to reduce the accumulation of 3RTau in neuronal cells both in an autocrine and exocrine manner.

The 3RT-apoB Single Chain Antibody Penetrates into the CNS and Reduces the Accumulation of 3RTau in a Transgenic Mouse Model of Tauopathy Given that we have shown that addition of the apoB increases BBB trafficking and cellular penetration of the scFv (33, 34, 36, 37, 40) without affecting activity, next we wanted to ascertain the efficacy of the 3RT antibody in vivo. For this purpose, we utilized a 3RTau mutant tg mouse model developed in our laboratory. This mouse model of PiD and tauopathies over-expresses 3RTau mutant under the pan-neuronal promoter mThy1 (38). The 3RTau tg mice show abnormal accumulation of 3RTau in the neocortex and limbic system with neurodegeneration, formation of PiD and tangle-like inclusions, and behavioral deficits (38). Non-tg and 3RTau tg mice received a single IP injection of the LV-3RT-apoB, LV-3RT or LV-control and after 4 months were evaluated behaviorally, biochemically and neuropathologically. Intraperitoneal delivery of the lentivector primarily transduces cells of the liver and the spleen where the transgene can be expressed and secreted into the bloodstream (37) thus the liver and spleen become the depot organs expressing the recombinant protein. Four months after the IP injections, mice were sacrificed and the levels of scFv and Tau in the brain were determined by immunoblot and immunohistochemistry.

Next, we determined if delivery of LV-3RT and LV-3RT-apoB reduces the taupathy in the transgenic (tg) mice. By Western blot, 3RTau, PHF1 and T-Tau were detected as bands at approximately 55 kDa. 3RTau was only detected only in the brain homogenates of the 3RTau tg mice, no band was observed in the non-tg (FIG. 5A). Moreover, compared to non-tg, the 3RTau tg mice displayed increased levels of PHF1 and t-Tau immunoreactive bands (FIG. 18A). When comparing to 3RTau tg mice that received LV-control or LV-3RT injections, only treatment with LV-3RT-apoB resulted in a reduction in the levels of 3RTau (FIG. 18A, C) and PHF1 (FIG. 18A, D) but constant levels of t-Tau (FIG. 18A, E).

Immunoblot analysis with an antibody against the V5 (to detect the protein products tag added to the scFv lentiviral constructs), showed the presence of the 3RT antibody as a band at approximately 20 kDa only in the brain homogenates from the 3RTau tg mice treated with LV-3RT-apoB but not in those treated with LV-control or LV-3RT (FIG. 5A,B). 3RTau, PHF1 and T-Tau were detected as bands at approximately 55 kDa. 3RTau was only detected only in the brain homogenates of the 3RTau tg mice, no band was observed in the non-tg (FIG. 18A). Moreover, compared to non-tg, the 3RTau tg mice displayed increased levels of PHF1 and t-Tau immunoreactive bands (FIG. 18A). When comparing to 3RTau tg mice that received LV-control or LV-3RT injections, only treatment with LV-3RT-apoB resulted in a reduction in the levels of 3RTau (FIG. 18A,C) and PHF1 (FIG. 18A,D) but constant levels of t-Tau (FIG. 18A,E).

Figure 12:
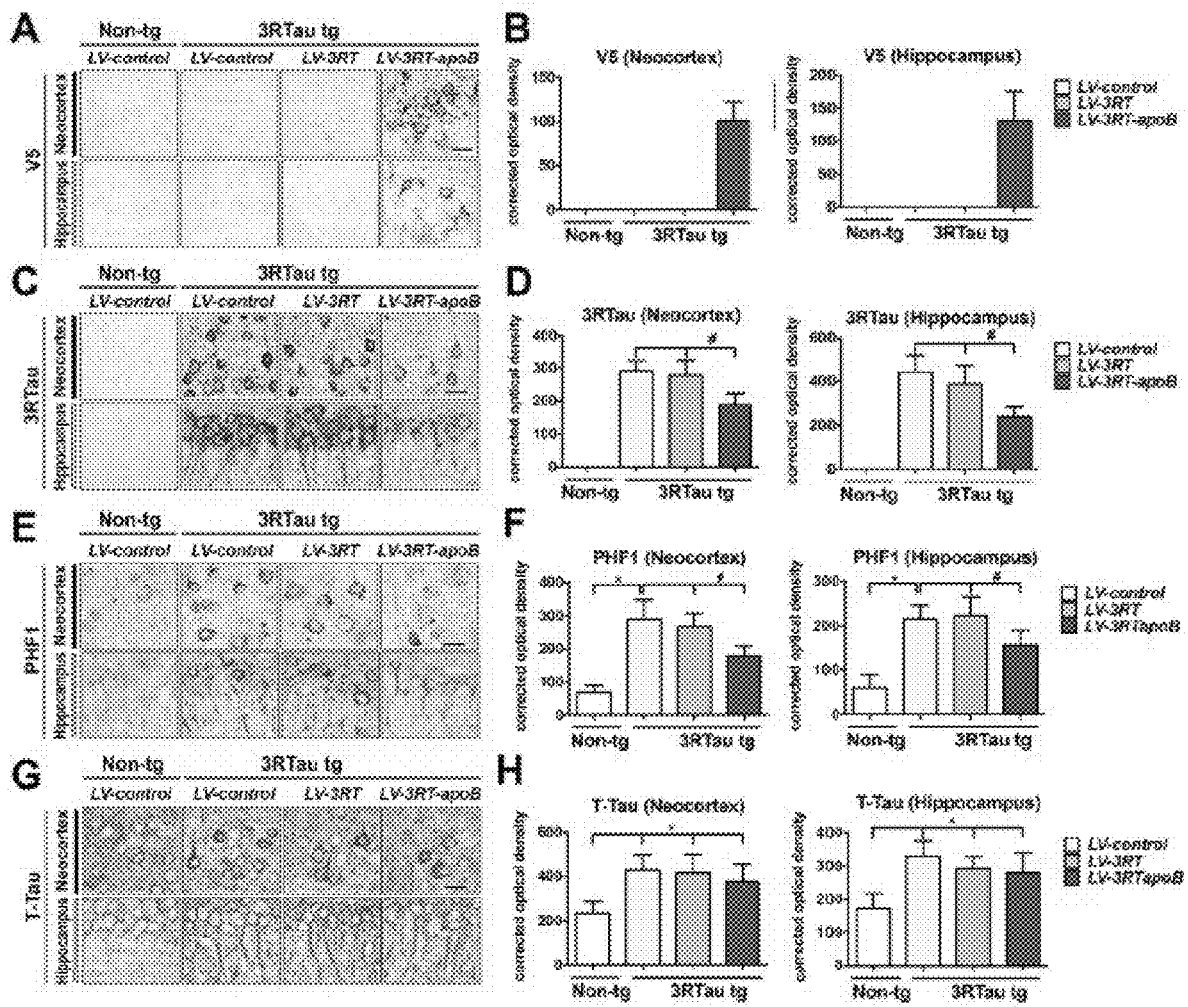
Figure 13:
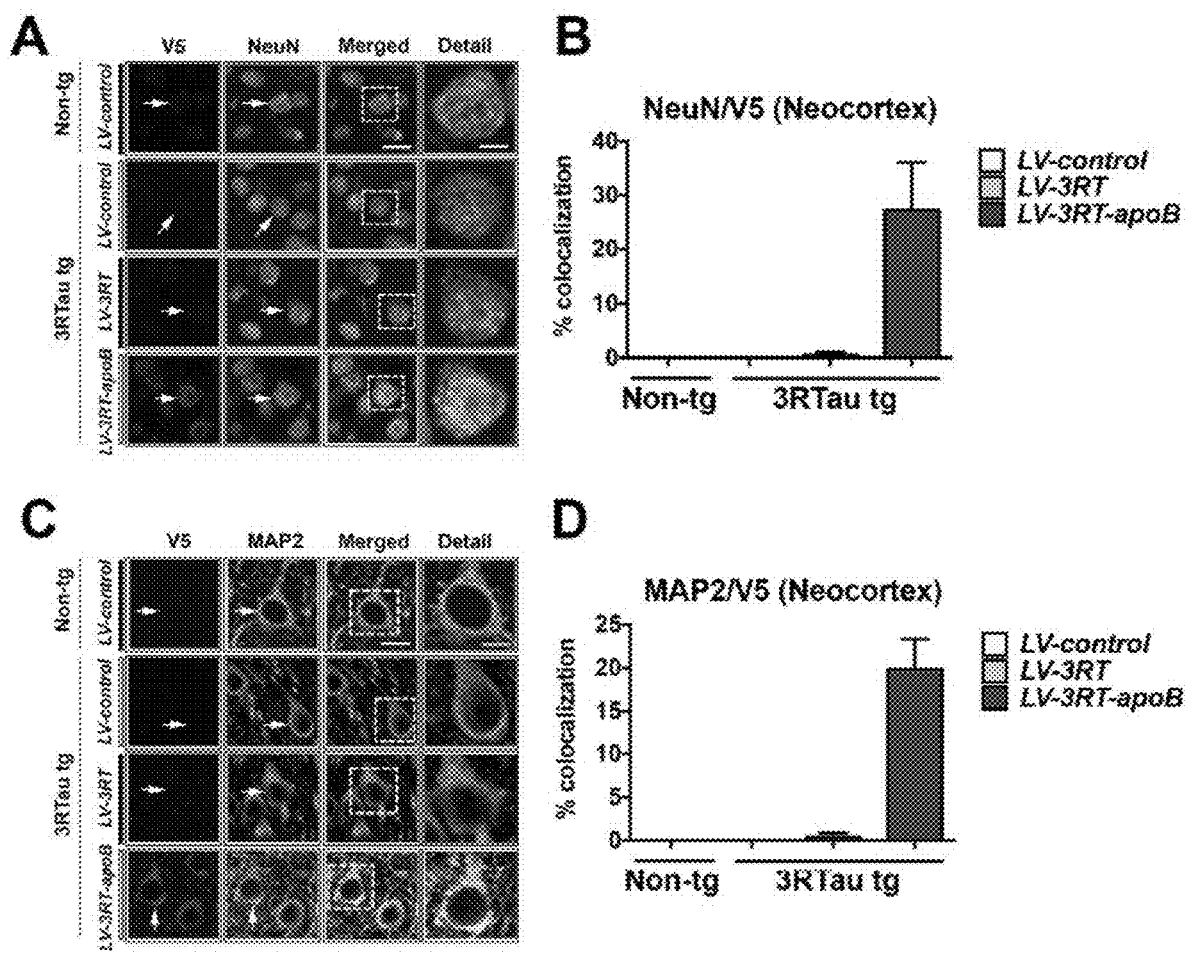
Figure 14:
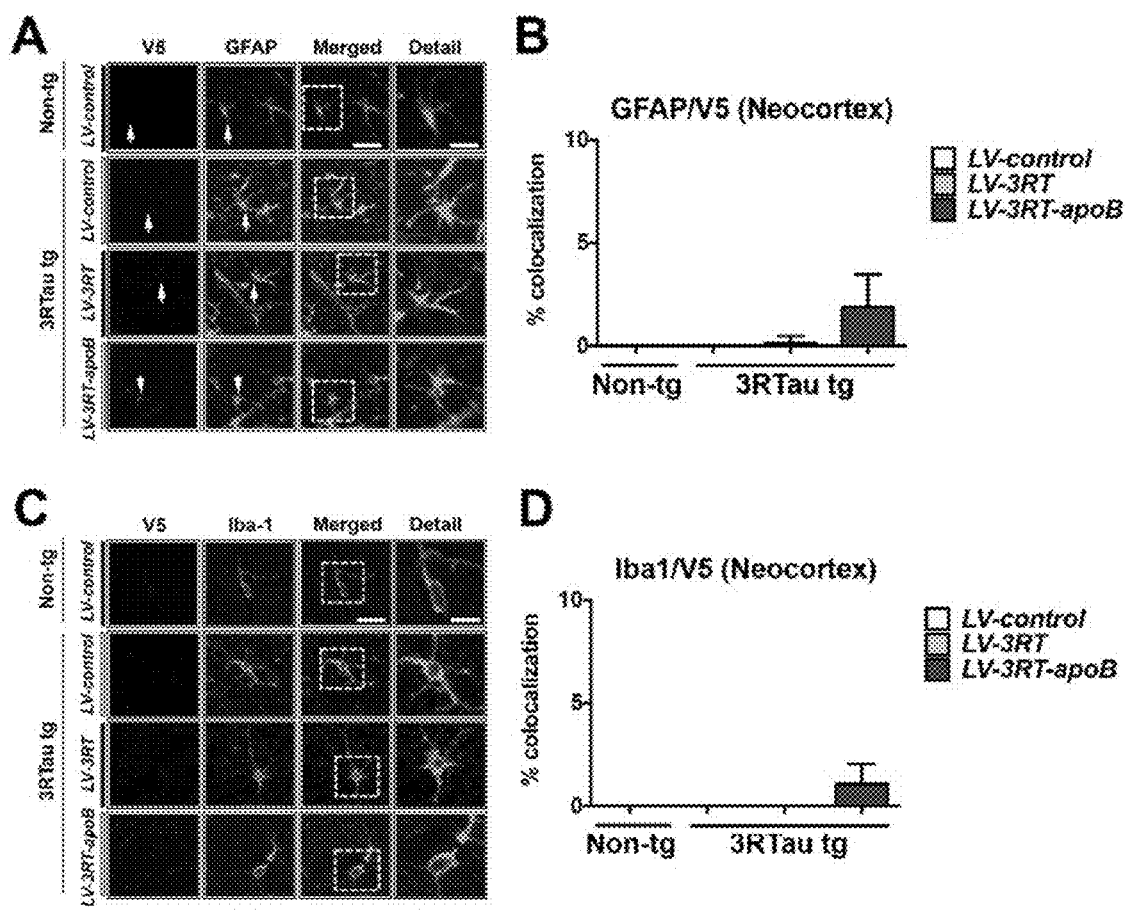
Figure 15:
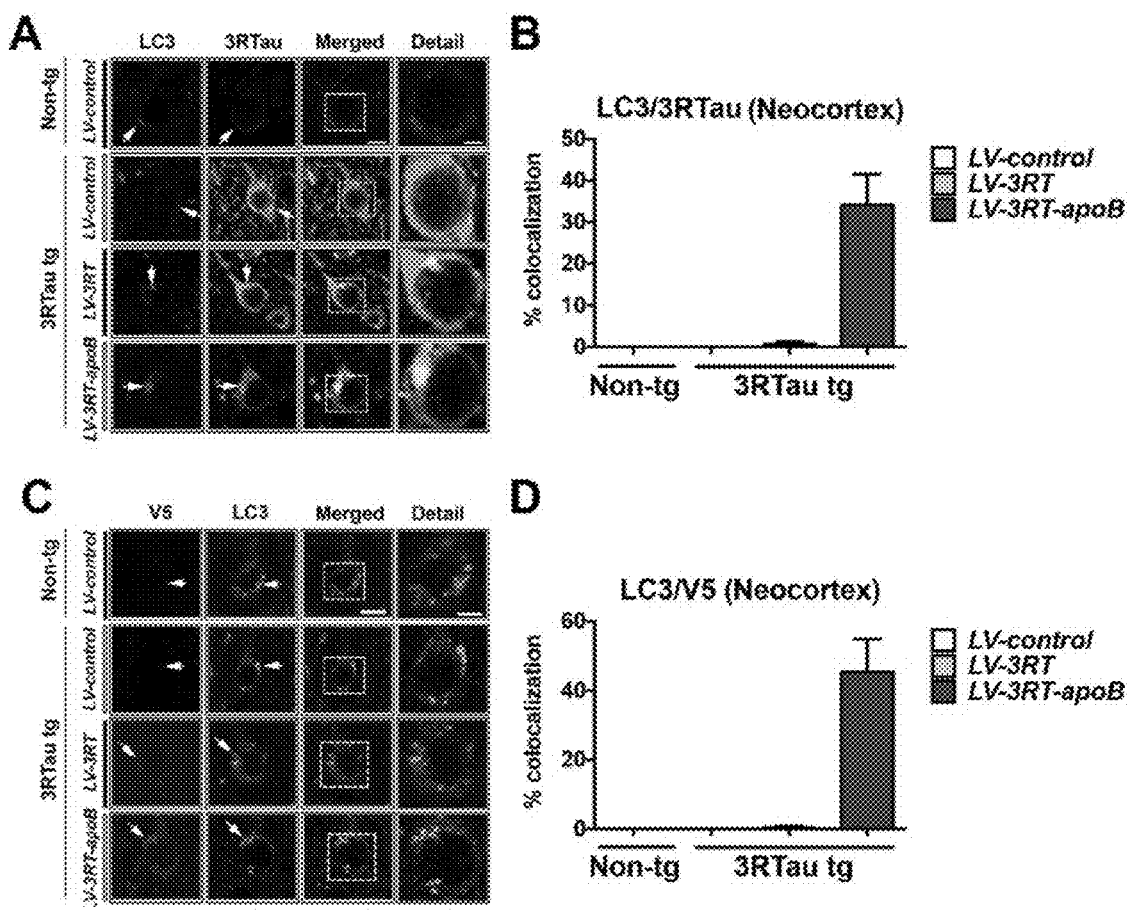

Consistent with the Western blot, immunocytochemical analysis with the anti-V5 antibody demonstrated the presence of clusters of positive cells in the neocortex and hippocampus in the 3RTau tg mice treated with LV-3RT-apoB but not in those treated with LV-control or LV-3RT alone (FIG. 12A,B). Levels of 3RTau were reduced by approximately 37% in the neocortex (deeper layers) and 47% in the hippocampus (CA1) of 3RTau tg mice treated with LV-3RT-apoB when comparing to tg mice treated with LV-control or LV-3RT (FIG. 12C,D). The 3RTau-tg mice also accumulate p-Tau that is detectable with the PHF1 antibody in neurons in the neocortex and hippocampus (FIG. 12E,F). We observed a 41% reduction in the levels of p-Tau immunoreactivity in the neocortex and 36% in the hippocampus of 3RTau tg mice treated with the LV-3RT-apoB when compared to tg mice treated with either LV-3RT or LV-control (FIG. 12E, F). In contrast, we did not observe a reduction in T-Tau protein in the 3R Tau-tg mice with treatment of either LV-3RT or LV-3RT-apoB vectors (FIG. 12G,H), suggesting that the 3RT-apoB was selectively reducing the abnormal accumulation of 3RTau and p-Tau without significantly affecting the overall levels of Tau (that is mostly composed of the endogenous mouse Tau protein).

In order to characterize the type of cells capturing the 3RT antibody, double labeling studies were performed with neuronal (NeuN and MAP2) and glial cell markers (GFAP and Iba1). These studies showed that the V5 tagged 3RT antibody co-localized to about 27% of NeuN (FIG. 13A,B) and 20% of MAP2 (FIG. 13C,D) positive pyramidal neurons in the in the deeper layers of the neocortex in the 3RTau tg mice treated with LV-3RT-apoB, with no co-localization detected in those mice treated with LV-control or LV-3RT (FIGS. 7A,B for NeuN and 13C,D for MAP2). Similar double labeling studies with glial markers revealed that the V5 tagged antibody co-localized to approximately 2% of GFAP positive astroglial cells (FIG. 14A, B) and 1% of the Iba1 positive microglial cells (FIG. 14C, D) in the deeper layers of the neocortex in the 3RTau tg mice treated with LV-3RT-apoB, with no co-localization detected in those mice treated with LV-control or LV-3RT (FIG. 14B, B for GFAP and FIG. 14C, D for Iba1).

Figure 16:
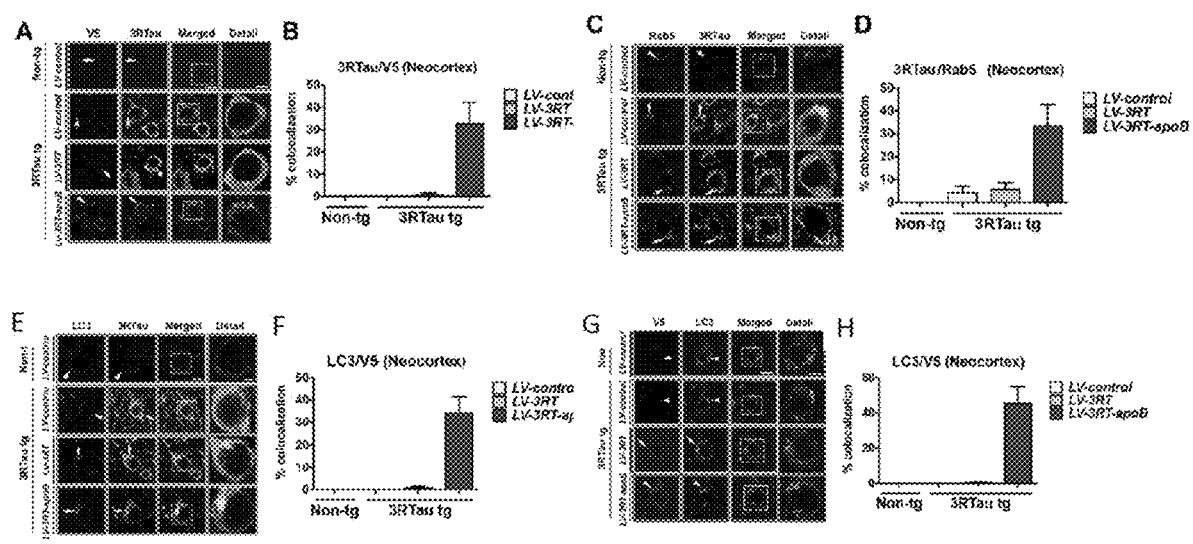

Addition of the apoB Sequence to the 3RT scFV Facilitates Cellular Uptake and Degradation of 3RTau Via an Endosomal-Lysosomal Pathway So far, our results indicate that the 3RT-apoB penetrated the CNS and neuronal cells reducing the accumulation of 3RTau and p-Tau in the neocortex and hippocampus of the 3RTau tg mice. However, it is unclear if the 3RT-apoB antibody engaged its target, namely 3RTau. For this purpose, additional double labeling experiments with performed with antibodies against 3RTau and V5. Confocal microscopy showed that compared to LV-control or LV-3RT, in 3RTau tg mice treated with LV-3RT-apoB, the antibody (V5, red channel) co-localized with 33% of the neurons displaying 3RTau immunoreactivity (FITC channel) (FIG. 16A,B). No or only background levels of signal was detected in mice treated with LV-control or LV-3RT (FIG. 16A,B). Interestingly, in mice treated with LV-3RT-apoB, the antibody (V5) co-localized intra-neuronally with 3RTau in granular structures in cell bodies, and the overall levels of 3RTau in these neurons appeared reduced compared to cells that did not display the co-localization with the 3RT antibody (FIG. 16A) (see detail to the right of dotted box).

We have previously shown that the apoB fragment enables the intra-cellular trafficking of the scFv antibodies via the LDL-R in the surface of neurons which in turn facilitates trafficking via the ESCRT pathway. Given that we found the antibody co-localizing with punctate structures in the neuronal cytoplasm, this suggests that the 3RTau and antibody might be taken up in endosomes for clearance and degradation. To further investigate this possibility, sections were double labeled with antibodies against 3RTau and the early endosomal marker Rab5. Confocal microscopy studies showed that in 3RTau tg mice treated with LV-3RT-apoB, Rab5 (red channel) co-localized with approximately 36% of the neurons displaying 3RTau immunoreactivity (FITC channel) (FIG. 16C,D). Only minimal co-localization (less than 5% of the cells) between Rab5 and 3RTau was detected in the 3RTau tg mice treated with LV-control or LV-3RT (FIG. 16C D).

These findings suggest that the 3RT antibody/3RTau complex in endosomes might be transferred to autophagosomes for degradation. To this end, sections were double labeled with antibodies against the autophagosomal marker-LC3 and 3RTau. Confocal microscopy analysis showed that in 3RTau tg mice treated with LV-3RT-apoB, LC3 (red channel) co-localized with approximately 32% of the neurons showing 3RTau immunostaining (FITC channel) (FIG. 16E, F). Only minimal (less than 1% of the cells) co-localization between LC3 and 3RTau was observed in tg mice treated with LV-control or LV-3RT (FIG. 16E,F). Similarly, LC3 (FITC channel) and V5 (red channel) co-localized in granular intra-cellular elements in about 45% of the neuronal cells in 3RTau tg mice treated with LV-3RT-apoB, but not in mice treated with LV-3RT or LV-control (FIG. 16G,H). Together, these results suggest that facilitated by the apoB fragment, the 3RT antibody and 3RTau were transported in the endosomal compartment for lysosomal degradation via autophagy.

Figure 17:
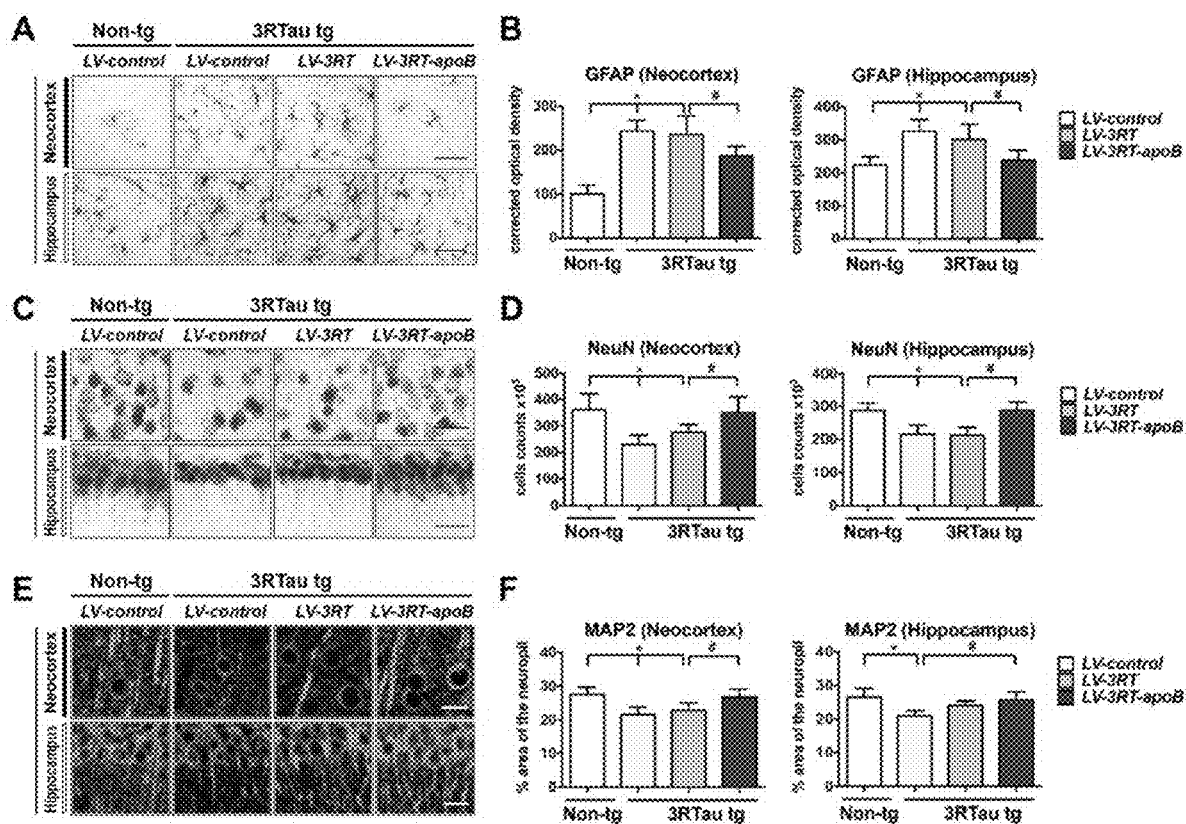

The 3RT-apoB Antibody Reduces Neurodegeneration and Behavioral Deficits in the 3RTau Transgenic Mouse Model of Tauopathy To determine if the reduction in 3RTau was accompanied by amelioration of the neurodegenerative phenotype, sections from non-tg and 3RTau tg mice were immunolabeled with antibodies against the astroglial marker-GFAP and the neuronal markers-NeuN and MAP2. As previously reported (38), immunostaining with the antibody against GFAP showed that compared to the LV-control non-tg mice, LV-control treated 3RTau tg mice displayed increased astrogliosis in the neocortex and hippocampus (FIG. 17A,B). In contrast, treatment with LV-3RT-apoB but not LV-3RT reduced astrogliosis in the 3RTau tg mice (FIG. 17A,B). Likewise, compared to the LV-control non-tg mice, LV-control treated 3RTau tg mice displayed decreased NeuN-positive neuronal cells in the neocortex and CA1 of the hippocampus (FIG. 17C,D). In contrast, treatment with LV-3RT-apoB but not LV-3RT ameliorated the loss of NeuN positive neurons in the neocortex and hippocampus of the 3RTau tg mice (FIG. 17C,D). We have previously shown that MAP2-a dendritic protein is a sensitive marker of neuronal damage (41). Compared to LV-control/non-tg mice the LV-control or LV-3RT treated 3RTau tg mice displayed a 29% reduction in the area of neuropil covered by MAP2 immunreactive dendrites (FIG. 17E,F). However, treatment with the LV-3RT-apoB prevented the loss of the MAP2 immunoreactive dendrites in the neocortex and hippocampus (FIG. 17E,F). This data supports the possibility that reduction of 3RTau protein by delivery of the 3RT antibody ameliorate the neurodegenerative damage and neuro-inflammation in the 3R Tau tg mice.

Finally, we wanted to determine if the reduced neurodegenerative pathology was associated with improvements in behavioral deficits. Mice were tested in a prepulse inhibition paradigm which evaluates the pre-attentive processes that operates outside of awareness and is used in animal models of neurodegeneration marked by an inability to block irrelevant information in cognitive domains. In this assay, compared to the LV-control, 3RTau tg mice showed an up to 45% reduction in % inhibition compared to LV-control treated non-tg mice. In contrast, 3RTau tg mice treated with the LV-3RT-apoB mice behaved similarly to the non-tg mice; whereas tg mice treated with the LV-3RT did not show any improvement (FIG. 19A). We previously showed the 3RTau-tg mice showed decreased habituation to a novel environment, as evidenced by increased high activity indicating a failure to learn (38). To determine if treatment of the 3RTau tg mice with the LV-3RT or LV-s3RT-apoB could ameliorate the learning deficits of the 3RTau tg mice, we examined the mice in the open field for number of beam breaks. As expected the LV-control treated 3RTau tg mice failed to habituate to the novel environment compared to LV-control/non-tg mice. In contrast, 3RTau tg mice treated with the LV-3RT-apoB mice behaved similarly to the non-tg mice; whereas tg mice treated with the LV-3RT did not show any improvement (FIG. 19B). Thus, treatment of 3RTau tg mice with the 3RT-apoB antibody is able to ameliorate the behavioral deficits present in this model of tauopathy.

Discussion

In this study, we generated a single chain antibody targeted specifically to the 3-repeat tau isoform for intent of reducing the accumulation of 3RTau specifically without affecting total or 4RTau levels. NMR studies confirmed the specificity of the single chain and showed that it binds to an epitope between aa 40-62 of 3RTau. Delivery of this specific antibody to a mouse model overexpressing 3RTau showed significant reduction in 3RTau accumulation accompanied by improvements in behavioral deficits and markers of neurodegeneration including neuronal loss and astrogliosis. Further evidence suggests that the antibody may have been able to promote clearance of 3RTau via the endosomal system and target 3RTau for degradation in lysosomes thus reducing the cell-to-cell propagation of tau aggregates in the brain. Taken together, brain targeted delivery of the single chain antibody specific for 3RTau may prove beneficial in restoring the physiological balance of neuronal tau isoforms during pathological conditions when 3RTau is in excess.

Our approach is different to others in that instead of targeting total Tau, 4RTau or phosphorylated Tau species we are targeting specifically 3RTau which is relevant to the pathogenesis of AD, PiD and other unusual tauopathies. While others have used active vaccination with peptides that elicit antibodies against various Tau species (42, 43) or with monoclonal antibodies against 4RTau or phosphorylated Tau species (25, 44, 45) that display low or variable degrees of CNS trafficking we chose to develop single chain antibodies selectively targeting 3RTau fused with a fragment of LDL-R binding protein (apoB) that enhances brain penetration. We have previously shown that this approach improves the penetration of proteins into the brain including neuropeptidases (33-37, 40) and single chain antibodies against a-synuclein (33-37, 40). The advantage of using single chain antibodies against 3RTau is that they have greater selectivity and higher affinity and since they lack Fc they are less prone to elicit inflammatory or undesired immunological reactions. We used as proof-of principle the lentiviral vector to express the 3RT-apoB in neuronal cells in culture or from the liver for constant expression into the blood in animal models.

The ratio between 3R and 4RTau in the neuron is regulated by alternative splicing of the MAPT gene such that exon 10 with 4RTau containing exon 10. The normal adult human brain contains approximately equal molar amounts of 3R:4RTau (46-48). Disruption of this ratio can be pathogenic (49-51) resulting in alterations in normal filament assembly and favoring aggregation (52). Therefore, a normal 50:50 balance of 3R:4RTau in the healthy brain is necessary, and targeting the 3R tau in a disease that results in overexpression of 3R tau will ideally restore the balance of the normal ration of 3R:4RTau without reducing only total Tau.

Tau protein is subjected to numerous post-translational modifications in the CNS, including phosphorylation, O-glycosylation and acetylation (23). Abnormal post-translational modifications have been linked to increased aggregations and Tau tangles. Pharmacologic approaches to block the phosphorylation of Tau through the Glycogen Synthase Kinase-3 have been attempted in the clinic; however, side effects from the small molecular inhibitor have slowed progress (24). Tau pathology occurs intra-neuronally; however, recent evidence suggests that the protein can also propagate from cell-to-cell (23). Tau oligomers or aggregates injected into wild-type or Tau transgenic mice show propagation and Tau aggregates from the site of injection and in vitro cultures show spread of Tau from cell-to-cell (23). Thus, Tau protein can exist outside of the cell and is a viable target for therapeutics. In fact, Tau has been observed in exosomes in patients with Alzheimer's disease and other tauopathies suggesting this might be a mechanism for cell-to-cell propagation (53-56). Therefore, several strategies for targeting Tau in AD and other tauopathies have been proposed, including small molecules preventing aggregation; anti-sense nucleotides to reduce tau expression; and more recently immunotherapy.

Among the many functions attributed to Tau protein in axons, directing axonal transport has been the subject of recent interest with respect to tau pathology. Anterograde and retrograde transport of cargos in the axon are mediated by the kinesin and dynein motors interacting with microtubules (57, 58). Tau regulates axon transport polarity by interacting with microtubules and competing for binding of these cargo transport motors (59, 60). Recently it was reported that the ratio of 3RTau and 4RTau in the axon can alter the direction of transport of APP-containing cargos, with higher levels of 3RTau favoring anterograde transport of APP toward the cell body and inhibiting the retrograde transport of those same cargos (61). Thus, reducing 3RTau protein could potentially decrease the accumulation of APP and/or Aβ in synaptic termini and increase degradation in the cell body.

In summary, the approach of utilizing the phage display approach to develop antibodies specific for very slight differences in proteins may be an approach worth investigating for tauopathies as well as other neurodegenerative diseases. Many pathological conditions occur from single point mutations or post-translational modification (1) that could be recognized and differentiated from wild-type or normal proteins through the use of positive and negative panning of phage display libraries. This approach allows for specific tailoring of targeting the antibody to the pathological species without affecting the normal physiological protein. We show here proof-of-principle that this approach can work for tauopathies and may be applied to other diseases as well.

Methods

Generation of 3RTau Single Chain Antibody

Identification and isolation of the 3RTau scFV (hereafter referred as 3RT antibody) was performed by Viva Biotech (Shanghai, China). Briefly, His and avidin-tagged 3RTau (352) and 4RTau (383) were twice purified over a Ni-column and concentrated with an ultracentrifugation column to a concentration to 6.3 mg/ml and 11.2 mg/ml respectively. A phage display library was positively panned over 3RTau coated beads and negatively panned over 4RTau coated beads to generate several clones. These clones were sequenced and cloned into mammalian scFV expression cassettes for further analysis. Further analysis was performed with immunoblot and ELISA using the recombinant 3RTau and 4RTau proteins to identify the clone (5F10) that uniquely bound to 3RTau without cross-reacting to 4RTau.

Large Scale Expression and Purification of Anti-3RT scFV

Human 3RTau scFV antibody was produced in HEK293 suspension cells using FreeStyle media following standard protocols. Briefly, 400 ml HEK293 cells in FreeStyle 293 media (Gibco) were transfected with 400 μg of pCAGG_3RTau_scFV expression construct, supplemented with 0.4 mg of pSV40-T helper plasmid to facilitate replication of the expression construct in the cells, and with 0.4 mg of a plasmid expressing a red fluorescent protein to monitor expression. 24 hours after transfection, cells were fed with 100 ml EX-CELL media (SIAL). Remaining media was harvested 120 hours post-transfection at 500 rpm for 10 min at 4° C. and the conditioned media was processed for purification.

A protease inhibitor cocktail (Thermofisher Halt™) and DTT to a final concentration of 1 mM were added to 1 L of media, followed by the filtration of the media using a 0.45 mm filter. The filtered media was then concentrated to 200 mL using a Amicon® Ultra centrifugal filter from EMD Millipore. The concentrated media was dialyzed against 30 mM HEPES, 100 mM NaCl, pH 6.8 before passing it through a 6 ml Resource Q column (GE Healthcare). In the next step, to remove the remaining impurities from the scFv, the flow through of the ResQ column was dialyzed against 30 mM MES, 100 mM NaCl, pH 5.5 and loaded onto a 6 ml Resource S column (GE Healthcare). The column was washed with 30 mM MES, 100 mM NaCl, pH 5.5 and the scFv was eluted with a 100-1000 mM NaCl linear gradient. Fractions containing pure scFv were pooled and dialyzed against 20 mM sodium phosphate buffer, 100 mM NaCl, pH 6.5 for subsequent NMR measurements.

Tau352 Expression and Purification

A pETM-11 plasmid containing the human tau352 sequence was transformed into E. coli (DE3) bacterial strain. The cells were grown at 37° C. in $^{15}$N isotopically labeled M9 minimal media to an optical density at 600 nm of approximately 0.7. After induction with 0.8 mM isopropyl-β-D-thiogalactopyranoside, tau352 was expressed for 5 h at 37° C. Cells were harvested by centrifugation, and resuspended in 20 mM TrisHCl, 150 mM NaCl, pH 7.6. The cells were lysed by sonication, after centrifugation at 18,000 rpm for 30 min, the tau352 containing supernatant was heated to 95° C. for 30 min. The solution was centrifuged at 18,000 rpm for 30 min to remove precipitated protein. Subsequently, the supernatant was loaded onto a 5 ml HisTrap column (GE Healthcare) equilibrated with 20 mM TrisHCl, pH 7.6, 300 mM NaCl and 10 mM imidazole. Tau352 was eluted with a 10-500 mM imidazole linear gradient. The fractions containing tau352 were pooled and dialyzed against 30 mM TrisHCl, pH 7.6, 100 mM NaCl, 0.5 mM EDTA and 1 mM DTT overnight. The His Tag was removed by TEV cleavage, and the cleavage reaction mixture was then dialyzed against a buffer containing 30 mM MES, pH 6.5, 100 mM NaCl and 1 mM DTT and afterwards loaded onto a 6 ml Resource S column (GE Healthcare). The column was washed with 30 mM MES, 100 mM NaCl, pH 6.5 and the protein was eluted with a 100-1000 mM NaCl linear gradient. Fractions containing pure tau352 were concentrated to 2 ml in a Amicon® Ultra centrifugal filter and finally passed through a Superdex 75 size-exclusion column (GE Healthcare) equilibrated with a buffer containing 20 mM sodium phosphate buffer, 100 mM NaCl, pH 6.5. The homogenous tau352 fractions were pooled and used for NMR measurements.

NMR Studies of Tau352 and scFv Binding

NMR experiments were recorded on a Bruker Avance 800 MHz spectrometer with 5% $D_2O$ as lock solvent at 25° C. The 2D $^1H$-$^{15}N$ HSQC experiments were recorded on a 15 mM $^{15}N$ labeled tau352 sample, for the interaction measurement an approximate 1:1 molar ratio between tau352 and scFv was used. For the 2D $^{15}N$ HSQC, 512 data points were recorded in the indirect dimension with 128 scans per point for free tau352 and scFv-bound tau352.

NMR spectra were processed with NMRPipe (62) and analyzed with ccpNMR (63). The relative peak intensities were obtained by dividing the peak volumes through the peak volume of residue 352 of tau352.

Construction of Lentivirus Vectors

The anti-3RTau scFV cDNA was PCR amplified and cloned into the third-generation self-inactivating lentivirus vector plasmid (64) with the CMV promoter driving expression and the secretory signal from the human CD5 gene (65) producing the vectors LV-s3RT. Addition of the ApoB 38 amino acid LDL-R binding domain was performed as previously described to generate LV-s3RT-ApoB. The lentivirus vector expressing the human wild-type α-syn and the control, LV-Control have been previously described (41). Lentiviruses were prepared by transient transfection in 293T cells (64).

Animal Care

All experiments described were carried out in strict accordance with good animal practice according to NIH recommendations, and all procedures for animal use were approved by the Institutional Animal Care and Use Committee at the University of California at San Diego (UCSD) under protocol #S07221.

Transgenic Mouse Lines and Injections of Lentiviral Vectors

For this study, mice over-expressing 3RTau from the mThy1 promoter (Line 13) were utilized (38). This model was selected because mice from this line develop intraneuronal 3RTau aggregates distributed through the neocortex and hippocampus similar to what has been described in Alzheimer's disease and Pick's disease.

To determine the effects of systemic injections of the lentivirus expressing 3RT briefly as previously described (34) total of 36 3RTau tg mice (n=12 LV-control, n=12 LV-3RT and n=12 LV-3RT-apoB) from (4 months old) and n=6 non-tg mice (LV-control) were injected intra-peritoneal (IP) with 100 μl of the lentiviral preparations (7.5×10$^8$ TU). Mice survived for 4 months after the lentiviral injection (8 months of age). Following NIH guidelines for the humane treatment of animals, blood was drawn and mice were anesthetized with chloral hydrate and flush-perfused transcardially with 0.9% saline.

Brains and peripheral tissues were removed and divided sagitally. The right hemibrain was post-fixed in phosphate-buffered 4% PFA (pH 7.4) at 4° C. for 48 hours for neuropathological analysis, while the left hemibrain was snap-frozen and stored at −70° C. for subsequent protein analysis.

Establishment of a Neuronal Cell Line Expressing 3RTau and scFV

For these experiments, we used the mouse cholinergic neuronal cell line Neuro2A (N2A) (39). For all experiments, cells were infected with LV expressing 3R Tau at a multiplicity of infection (MOI) of 20. Cells were co-infected with LV-s3RT, LV-s3RT-ApoB or empty vector (LV-control). After infection, cells were incubated in a humidified, 5% $CO_2$ atmosphere at 37° C. All experiments were conducted in triplicate to ensure reproducibility.

To verify expression levels of 3RTau and the scFV in cells infected with the different LV vectors, N2A neurons were seeded onto poly L-lysine-coated glass coverslips, grown to 60% confluence and fixed in 4% paraformaldehyde (PFA) for 20 minutes. Coverslips were pre-treated with 0.1% Triton X-100 in Tris-buffered saline (TBS) for 20 min and then incubated overnight at 4° C. with antibodies against 3R Tau (Chemicon, Temecula, Calif.) or V5 epitope (scFV) (Sigma, St Louis, Mo.). with biotinylated secondary antibody and reacted with diaminobenzidine. All sections were processed under the same standardized conditions. Control samples included: empty vector (referred hereafter as LV-control), and immunolabeling in the absence of primary antibodies. Cells were analyzed with a digital microscope Zeiss Imager.A2 (Zeiss, Cambridge, Mass.).

For co-culture analysis, 5×10$^4$ N2A cells were plated onto poly L-lysine coated glass coverslips or onto 12 well cell culture inserts containing a 0.4 μm PET membrane (Fisher Scientific). Cultures were incubated separately for 6 hours to allow cells to attach and then co-cultured until analysis.

To verify the co-expression in neuronal cells co-infected with the different LV vectors, coverslips were double labeled with antibodies against 3RTau (Chemicon) and MAP2 (Millipore) as previously described (41). Coverslips were air-dried, mounted on slides with anti-fading media (Vectashield, Vector Laboratories, Burlingame, Calif.), and imaged with confocal microscope. An average of 50 cells were imaged per condition and the individual channel images were merged and analyzed with the Image J program to estimate the extent of co-localization between Tau and MAP2.

Immunocytochemical and Neuropathological Analyses

Analysis of Tau accumulation was performed in serially sectioned, free-floating, blind-coded vibratome sections from tg and non-tg mice treated with LV-3RT, LV-3RT-apoB and LV-Control vectors (41). Sections were incubated overnight at 4° C. with anti-V5 (Sigma) (scFV epitope), 3RTau (Chemicon), PHF1 (ThermoFisher) and T-Tau (Abcam, Cambridge, Mass.) antibodies (66), followed by biotinylated goat appropriate antibodies (Vector Laboratories, Inc., Burlingame, Calif.), Avidin D-HRP (ABC Elite, Vector, Burlingame, Calif.) and detection with the Tyramide Signal Amplification™-Direct (Red) system (NEN Life Sciences, Boston, Mass.). For each mouse, three sections were a digital Zeiss light microscope and the results were averaged and expressed as corrected optical density.

To determine the co-localization between 3RT scFV and cells in the CNS, 40 μm-thick vibratome sections were immunolabeled with the rabbit polyclonal antibody against the 3RT scFV (V5 epitope) and Map2 (neuronal dendritic marker, Chemicon), NeuN (neuronal nuclear marker, Millipore), GFAP (astrocyte marker, Chemicon) or Iba1 (microglia marker, Wako). The scFV immunoreactive structures were detected with the Tyramide Signal Amplification™-Direct (Red) system (NEN Life Sciences, Boston, Mass.) while the cellular specific markers were detected with the horse anti-mouse IgG fluorescein isothiocyanate (FITC) antibody (Vector, Burlingame, Calif.).

To determine the co-localization between the anti-3R Tau scFV (V5), LC3, 3RTau, and Rab5 markers double-labeling experiments were performed as previously described (67). For this purpose, vibratome sections were immunolabeled with the rabbit polyclonal antibodies against 3R Tau, LC3 (Abcam, autophagy marker, San Francisco, Calif.), anti-V5, Rab5 (BD Transduction Laboratories, endosomal marker, San Jose, Calif.). All sections were processed simultaneously under the same conditions and experiments were performed twice in order to assess the reproducibility of results. Sections were imaged with a Zeiss 63X (N.A. 1.4) objective on an LSM800 digital confocal microscope (Zeiss, Cambridge, Mass.).

To determine if the scfV gene transfer ameliorated the neurodegenerative alterations associated with the expression of 3RTau, briefly as previously described (41), blind-coded, 40-μm thick vibratome sections from mouse brains fixed in 4% paraformaldehyde were immunolabeled with the mouse monoclonal antibody against microtubule-associated protein-2, (MAP2, dendritic marker, Chemicon, Temecula, Calif.) (41). After overnight incubation with the primary antibody, sections were incubated with fluorescein isothiocyanate (FITC)-conjugated horse anti-mouse IgG secondary antibody (Vector Laboratories, Burlingame, Calif.), transferred to SuperFrost slides (Fisher Scientific, Hampton, N.H.) and mounted under glass coverslips with anti-fading media (Vector Laboratories, Burlingame, Calif.). Other sets of sections immunostained with antibodies for NeuN and GFAP were incubated with biotinylated secondary antibody and reacted with diaminobenzidine. All sections were processed under the same standardized conditions. The immunolabeled blind-coded sections were serially imaged with the LSCM and analyzed with the Image 1.43 program (NIH, Bethesda, Md.), as previously described (41). For each mouse, a total of three sections from the hippocampus and three from the cortex were analyzed and for each section, four fields in the frontal cortex and hippocampus were examined. For MAP2, results were expressed as percent area of the neuropil occupied by immunoreactive dendrites. For NeuN, sections were analyzed by the dissector method using Stereo-Investigator System (MBF Bioscience) and the results were expressed as numbers per $mm^3$. For GFAP, sections were analyzed by light microscopy with a digital Zeiss microscope and expressed as corrected optical density. All sections were processed simultaneously under the same conditions and experiments were performed twice in order to assess the reproducibility of results (66).

Behavioral Testing

The open field locomotor test was used to determine basal activity levels of study subjects (total move time) during a 15 min session as previously described (39). Briefly. spontaneous activity in an open field (25.5×25.5 cm) was monitored for 15 min using an automated system (Truscan system for mice; Coulbourn Instruments). Animals were tested within the first 2-4 h of the dark cycle after being habituated to the testing room for 15 min. The open field was illuminated with a lamp equipped with a 25 W red bulb. Time spent in motion was automatically collected in 3 times for 5 min each using TruScan software. Data were analyzed for both the entire 15 min session and for each of the 5 min time blocks.

For PPI the protocol was adapted from Papaleo et al. (68). Briefly, mice treated with LV-control, LV-3RT and LV-3RT apoB were placed in the startle chambers for a 5-min acclimation period with a 65 dB(A) background noise. Animals were then exposed to a series of trial types. The inter trial interval (ITI) was 5-60 s. One trial type measured the response to no stimulus (baseline movement), and another one measured the startle stimulus alone (acoustic amplitude), which was a 40 ms 120 dB sound burst. Other five trial types were acoustic prepulse plus acoustic startle stimulus trials. Prepulse tones were 20 ms at 70, 75, 80, 85, and 90 presented 100 ms before the startle stimulus. PPI was calculated and expressed as % inhibition.

Statistical Analysis

All experiments were performed blind coded and in triplicate. Values in the figures are expressed as means±SEM. To determine the statistical significance, values were compared by using the one-way ANOVA with posthoc Dunnet when comparing the scFV treated samples to LV-control treated samples. Additional comparisons were done using Tukey-Krammer or Fisher posthoc tests. The differences were considered to be significant if p values were less than 0.05.

REFERENCES

1. Y. Wang et al., Tau in physiology and pathology. *Nat Rev Neurosci* 17, 5-21 (2016).
2. C. Ballatore, V. M. Lee, J. Q. Trojanowski, Tau-mediated neurodegeneration in Alzheimer's disease and related disorders. *Nat Rev Neurosci* 8, 663-672 (2007).
3. V. M. Lee, M. Goedert, J. Q. Trojanowski, Neurodegenerative tauopathies. *Annu Rev Neurosci* 24, 1121-1159 (2001).
4. Y. Gao, L. Tan, J. T. Yu, L. Tan, Tau in Alzheimer's disease: Mechanisms and therapeutic strategies. *Curr Alzheimer Res*, (2017).
5. C. Haass, D. J. Selkoe, Soluble protein oligomers in neurodegeneration: lessons from the Alzheimer's amyloid beta-peptide. *Nature reviews. Molecular cell biology* 8, 101-112 (2007).
6. B. De Strooper, E. Karran, The Cellular Phase of Alzheimer's Disease. *Cell* 164, 603-615 (2016).
7. L. Sibener, I. Zaganjor, H. M. Snyder, L. J. Bain, R. Egge, M. C. Carrillo, Alzheimer's Disease prevalence, costs, and prevention for military personnel and veterans. *Alzheimer's & dementia: the journal of the Alzheimer's Association* 10, S105-110 (2014).
8. Alzheimer's Association, Latest Facts and Figures Report. (2015).
9. R. Terry, L. Hansen, E. Masliah, in *Alzheimer disease*, R. Terry, R. Katzman, Eds. (Raven Press, New York, 1994), pp. 179-196.
10. C. R. Overk, E. Masliah, Pathogenesis of synaptic degeneration in Alzheimer's disease and Lewy body disease. *Biochemical pharmacology* 88, 508-516 (2014).
11. D. J. Selkoe, J. Hardy, The amyloid hypothesis of Alzheimer's disease at 25 years. *EMBO molecular medicine* 8, 595-608 (2016).
12. L. Mucke, D. J. Selkoe, Neurotoxicity of amyloid beta-protein: synaptic and network dysfunction. *Cold Spring Harbor perspectives in medicine* 2, a006338 (2012).

13. C. A. A. del, K. Iqbal, Tau-induced neurodegeneration: a clue to its mechanism. *J Alzheimers Dis* 8, 223-226 (2005).
14. A. Andreadis, W. M. Brown, K. S. Kosik, Structure and novel exons of the human tau gene. *Biochemistry* 31, 10626-10633 (1992).
15. M. L. Caillet-Boudin, L. Buee, N. Sergeant, B. Lefebvre, Regulation of human MAPT gene expression. *Molecular neurodegeneration* 10, 28 (2015).
16. T. Guo, W. Noble, D. P. Hanger, Roles of tau protein in health and disease. *Acta Neuropathol* 133, 665-704 (2017).
17. N. T. Olney, et al., Frontotemporal Dementia. *Neurol Clin* 35, 339-374 (2017).
18. T. Arendt, et al., Tau and tauopathies. *Brain Res Bull* 126, 238-292 (2016).
19. P. Tacik, M. Sanchez-Contreras, R. Rademakers, D. W. Dickson, Z. K. Wszolek, Genetic Disorders with Tau Pathology: A Review of the Literature and Report of Two Patients with Tauopathy and Positive Family Histories. *Neurodegener Dis* 16, 12-21 (2016).
20. D. W. Dickson, N. Kouri, M. E. Murray, K. A. Josephs, Neuropathology of frontotemporal lobar degeneration-tau (FTLD-tau). *J Mol Neurosci* 45, 384-389 (2011).
21. G. G. Kovacs, Invited review: Neuropathology of tauopathies: principles and practice. *Neuropathol Appl Neurobiol* 41, 3-23 (2015).
22. N. Takeda, Y. Kishimoto, O. Yokota, Pick's disease. *Adv Exp Med Biol* 724, 300-316 (2012).
23. G. Simic, M. Babic Leko, S. Wray, C. Harrington, I. Delalle, N. Jovanov-Milosevic, D. Bazadona, L. Buee, R. de Silva, G. Di Giovanni, C. Wischik, P. R. Hof, Tau Protein Hyperphosphorylation and Aggregation in Alzheimer's Disease and Other Tauopathies, and Possible Neuroprotective Strategies. *Biomolecules* 6, (2016).
24. J. T. Pedersen, E. M. Sigurdsson, Tau immunotherapy for Alzheimer's disease. *Trends Mol Med* 21, 394-402 (2015).
25. E. Valera, B. Spencer, E. Masliah, Immunotherapeutic Approaches Targeting Amyloid-beta, alpha-Synuclein, and Tau for the Treatment of Neurodegenerative Disorders. *Neurotherapeutics* 13, 179-189 (2016).
26. K. A. Vossel, et al., Tau reduction prevents Abeta-induced axonal transport deficits by blocking activation of GSK3beta. *The Journal of cell biology* 209, 419-433 (2015).
27. S. Ikegami, A. Harada, N. Hirokawa, Muscle weakness, hyperactivity, and impairment in fear conditioning in tau-deficient mice. *Neurosci Lett* 279, 129-132 (2000).
28. A. Harada, K. Oguchi, S. Okabe, J. Kuno, S. Terada, T. Ohshima, R. Sato-Yoshitake, Y. Takei, T. Noda, N. Hirokawa, Altered microtubule organization in small-calibre axons of mice lacking tau protein. *Nature* 369, 488-491 (1994).
29. H. N. Dawson, A. Ferreira, M. V. Eyster, N. Ghoshal, L. I. Binder, M. P. Vitek, Inhibition of neuronal maturation in primary hippocampal neurons from tau deficient mice. *Journal of cell science* 114, 1179-1187 (2001).
30. H. N. Dawson, V. Cantillana, M. Jansen, H. Wang, M. P. Vitek, D. M. Wilcock, J. R. Lynch, D. T. Laskowitz, Loss of tau elicits axonal degeneration in a mouse model of Alzheimer's disease. *Neuroscience* 169, 516-531 (2010).
31. V. Seiberlich, et al., Downregulation of the microtubule associated protein tau impairs process outgrowth and myelin basic protein mRNA transport in oligodendrocytes. *Glia* 63, 1621-1635 (2015).
32. S. K. Schroeder, A. Joly-Amado, M. N. Gordon, D. Morgan, Tau-Directed Immunotherapy: A Promising Strategy for Treating Alzheimer's Disease and Other Tauopathies. *Journal of neuroimmune pharmacology: the official journal of the Society on NeuroImmune Pharmacology* 11, 9-25 (2016).
33. B. Spencer, S. Emadi, P. Desplats, S. Eleuteri, S. Michael, K. Kosberg, J. Shen, E. Rockenstein, C. Patrick, A. Adame, T. Gonzalez, M. Sierks, E. Masliah, ESCRT-mediated uptake and degradation of brain-targeted alpha-synuclein single chain antibody attenuates neuronal degeneration in vivo. *Mol Ther* 22, 1753-1767 (2014).
34. B. Spencer, R. A. Man, R. Gindi, R. Potkar, S. Michael, A. Adame, E. Rockenstein, I. M. Verma, E. Masliah, Peripheral delivery of a CNS targeted, metalo-protease reduces abeta toxicity in a mouse model of Alzheimer's disease. *PLoS One* 6, e 16575 (2011).
35. B. Spencer, R. Potkar, J. Metcalf, I. Thrin, A. Adame, E. Rockenstein, E. Masliah, Systemic Central Nervous System (CNS) targeted Delivery of Neuropeptide Y (NPY) Reduces Neurodegeneration and Increases Neural Precursor Cell Proliferation in a Mouse Model of Alzheimer Disease. *J Biol Chem* 291, 1905-1920 (2016).
36. B. Spencer, I. Verma, P. Desplats, D. Morvinski, E. Rockenstein, A. Adame, E. Masliah, A neuroprotective brain-penetrating endopeptidase fusion protein ameliorates Alzheimer disease pathology and restores neurogenesis. *J Biol Chem* 289, 17917-17931 (2014).
37. B. J. Spencer, I. M. Verma, Targeted delivery of proteins across the blood-brain barrier. *Proc Natl Acad Sci USA* 104, 7594-7599 (2007).
38. E. Rockenstein, et al., A novel triple repeat mutant tau transgenic model that mimics aspects of pick's disease and fronto-temporal tauopathies. *PLoS One* 10, e0121570 (2015).
39. B. Spencer, P. A. Desplats, C. R. Overk, E. Valera-Martin, R. A. Rissman, C. Wu, M. Mante, A. Adame, J. Florio, E. Rockenstein, E. Masliah, Reducing Endogenous alpha-Synuclein Mitigates the Degeneration of Selective Neuronal Populations in an Alzheimer's Disease Transgenic Mouse Model. *J Neurosci* 36, 7971-7984 (2016).
40. B. Spencer, E. Valera, E. Rockenstein, M. Trejo-Morales, A. Adame, E. Masliah, A brain-targeted, modified neurosin (kallikrein-6) reduces alpha-synuclein accumulation in a mouse model of multiple system atrophy. *Molecular neurodegeneration* 10, 48 (2015).
41. B. Spencer, R. Potkar, M. Trejo, E. Rockenstein, C. Patrick, R. Gindi, A. Adame, T. Wyss-Coray, E. Masliah, Beclin 1 gene transfer activates autophagy and ameliorates the neurodegenerative pathology in alpha-synuclein models of Parkinson's and Lewy body diseases. *J Neurosci* 29, 13578-13588 (2009).
42. E. Kontsekova, N. Zilka, B. Kovacech, P. Novak, M. Novak, First-in-man tau vaccine targeting structural determinants essential for pathological tau-tau interaction reduces tau oligomerisation and neurofibrillary degeneration in an Alzheimer's disease model. *Alzheimers Res Ther* 6, 44 (2014).
43. C. Theunis, N. Crespo-Biel, V. Gafner, M. Pihlgren, M. P. Lopez-Deber, P. Reis, D. T. Hickman, O. Adolfsson, N. Chuard, D. M. Ndao, P. Borghgraef, H. Devijver, F. Van Leuven, A. Pfeifer, A. Muhs, Efficacy and safety of a liposome-based vaccine against protein Tau, assessed in tau.P301L mice that model tauopathy. *PLoS One* 8, e72301 (2013).

44. J. Bright, S. Hussain, V. Dang, S. Wright, B. Cooper, T. Byun, C. Ramos, A. Singh, G. Parry, N. Stagliano, I. Griswold-Prenner, Human secreted tau increases amyloid-beta production. *Neurobiol Aging* 36, 693-709 (2015).
45. L. Collin, et al., Neuronal uptake of tau/pS422 antibody and reduced progression of tau pathology in a mouse model of Alzheimer's disease. *Brain* 137, 2834-2846 (2014).
46. M. Goedert, R. Jakes, Expression of separate isoforms of human tau protein: correlation with the tau pattern in brain and effects on tubulin polymerization. *EMBO J* 9, 4225-4230 (1990).
47. M. Goedert, M. G. Spillantini, R. Jakes, D. Rutherford, R. A. Crowther, Multiple isoforms of human microtubule-associated protein tau: sequences and localization in neurofibrillary tangles of Alzheimer's disease. *Neuron* 3, 519-526 (1989).
48. K. S. Kosik, L. D. Orecchio, S. Bakalis, R. L. Neve, Developmentally regulated expression of specific tau sequences. *Neuron* 2, 1389-1397 (1989).
49. M. Hutton, et al., Association of missense and 5'-splice-site mutations in tau with the inherited dementia FTDP-17. *Nature* 393, 702-705 (1998).
50. M. G. Spillantini, J. R. Murrell, M. Goedert, M. R. Farlow, A. Klug, B. Ghetti, Mutation in the tau gene in familial multiple system tauopathy with presenile dementia. *Proc Natl Acad Sci USA* 95, 7737-7741 (1998).
51. M. Hong, et al., Mutation-specific functional impairments in distinct tau isoforms of hereditary FTDP-17. *Science* 282, 1914-1917 (1998).
52. S. J. Adams, M. A. DeTure, M. McBride, D. W. Dickson, L. Petrucelli, Three repeat isoforms of tau inhibit assembly of four repeat tau filaments. *PLoS One* 5, e10810 (2010).
53. A. L. Woerman, A. Aoyagi, S. Patel, S. A. Kazmi, I. Lobach, L. T. Grinberg, A. C. McKee, W. W. Seeley, S. H. Olson, S. B. Prusiner, Tau prions from Alzheimer's disease and chronic traumatic encephalopathy patients propagate in cultured cells. *Proc Natl Acad Sci USA* 113, E8187-E8196 (2016).
54. M. Shi, et al., CNS tau efflux via exosomes is likely increased in Parkinson's disease but not in Alzheimer's disease. *Alzheimer's & dementia: the journal of the Alzheimer's Association* 12, 1125-1131 (2016).
55. C. N. Winston, E. J. Goetzl, J. C. Akers, B. S. Carter, E. M. Rockenstein, D. Galasko, E. Masliah, R. A. Rissman, Prediction of conversion from mild cognitive impairment to dementia with neuronally derived blood exosome protein profile. *Alzheimers Dement (Amst)* 3, 63-72 (2016).
56. S. Saman, W. Kim, M. Raya, Y. Visnick, S. Miro, S. Saman, B. Jackson, A. C. McKee, V. E. Alvarez, N. C. Lee, G. F. Hall, Exosome-associated tau is secreted in tauopathy models and is selectively phosphorylated in cerebrospinal fluid in early Alzheimer disease. *J Biol Chem* 287, 3842-3849 (2012).
57. S. Terada, M. Kinjo, M. Aihara, Y. Takei, N. Hirokawa, Kinesin-1/Hsc70-dependent mechanism of slow axonal transport and its relation to fast axonal transport. *EMBO J* 29, 843-854 (2010).
58. S. E. Encalada, L. S. Goldstein, Biophysical challenges to axonal transport: motor-cargo deficiencies and neurodegeneration. *Annu Rev Biophys* 43, 141-169 (2014).
59. R. Dixit, J. L. Ross, Y. E. Goldman, E. L. Holzbaur, Differential regulation of dynein and kinesin motor proteins by tau. *Science* 319, 1086-1089 (2008).
60. N. M. Kanaan, G. Morfini, G. Pigino, N. E. LaPointe, A. Andreadis, Y. Song, E. Leitman, L. I. Binder, S. T. Brady, Phosphorylation in the amino terminus of tau prevents inhibition of anterograde axonal transport. *Neurobiol Aging* 33, 826 e815-830 (2012).
61. V. Lacovich, S. L. Espindola, M. Alloatti, V. Pozo Devoto, L. E. Cromberg, M. E. Carna, G. Forte, J. M. Gallo, L. Bruno, G. B. Stokin, M. E. Avale, T. L. Falzone, Tau Isoforms Imbalance Impairs the Axonal Transport of the Amyloid Precursor Protein in Human Neurons. *J Neurosci* 37, 58-69 (2017).
62. F. Delaglio, S. Grzesiek, G. W. Vuister, G. Zhu, J. Pfeifer, A. Bax, NMRPipe: a multidimensional spectral processing system based on UNIX pipes. *Journal of biomolecular NMR* 6, 277-293 (1995).
63. W. F. Vranken, W. Boucher, T. J. Stevens, R. H. Fogh, A. Pajon, M. Llinas, E. L. Ulrich, J. L. Markley, J. Ionides, E. D. Laue, The CCPN data model for NMR spectroscopy: development of a software pipeline. *Proteins* 59, 687-696 (2005).
64. B. Spencer, et al., Lentivirus mediated delivery of neurosin promotes clearance of wild-type alpha-synuclein and reduces the pathology in an alpha-synuclein model of LBD. *Mol Ther* 21, 31-41 (2013).
65. N. H. Jones, et al., Isolation of complementary DNA clones encoding the human lymphocyte glycoprotein T1/Leu-1. *Nature* 323, 346-349 (1986).
66. E. Masliah, et al., Dopaminergic loss and inclusion body formation in alpha-synuclein mice: implications for neurodegenerative disorders. *Science* 287, 1265-1269 (2000).
67. E. Masliah, et al., Passive immunization reduces behavioral and neuropathological deficits in an alpha-synuclein transgenic model of Lewy body disease. *PLoS One* 6, e19338 (2011).
68. F. Papaleo, B. K. Lipska, D. R. Weinberger, Mouse models of genetic effects on cognition: relevance to schizophrenia. *Neuropharmacology* 62, 1204-1220 (2012).

A number of embodiments of the invention have been described. Nevertheless, it can be understood that various modifications may be made without departing from the spirit and scope of the invention. Accordingly, other embodiments are within the scope of the following claims.

What is claimed is:

1. A pharmaceutical composition, a nanoparticle, a particle, a liposome, a micelle, or an implant, comprising an antibody or single chain antibody fragment (scFV) that specifically targets, or specifically binds to, a 3-repeat (3R) Tau polypeptide and does not specifically recognize or bind to a 4-repeat (4R) Tau polypeptide, wherein the antibody or scFv comprises a VH domain MEQVNLRESGAEVKKP-GASVKVSCKVSGYTFTGYY MHWVRQAPGQ-GLEWMGWINS NSGATKYAQKFQGRVTMTRDTSITT AYMELSSLRSDDTAVYYCARGARDGYGFDYW GQGTLVTVL (SEQ ID NO: 4) and a VL domain SYVLTQPPSASGTPGQRVTISCSGGSSNIGSNAVS WYQQLPGTAPK LLIFTNDQRPSGVPDRFSGSKSGT-SAPLAISGLQS EDESDYYCATW DDSLNGWVFGGGTKVTV (SEQ ID NO: 6).

2. A recombinant or synthetic single chain antibody fragment (scFv) comprising SEQ ID NO: 2.

3. A kit comprising the antibody of claim 1 and the antibody is linked to or conjugated to a detectable moiety, or the kit comprises a detectable antibody that specifically binds to the antibody of claim 1 that targets, or specifically binds to, a 3-repeat (3R) Tau polypeptide, and components for carrying out an ELISA assay.

4. A kit comprising a synthetic scFv of claim 2.

5. The pharmaceutical composition, nanoparticle, particle, liposome, micelle or implant of claim 1, wherein the antibody is a single chain antibody fragment (scFv).

6. The pharmaceutical composition, nanoparticle, particle, liposome, micelle or implant of claim 1, wherein the scFv is encoded by a nucleotide sequence comprising SEQ ID NO: 1 or comprises an amino acid sequence as set forth in SEQ ID NO: 2.

7. The pharmaceutical composition, nanoparticle, particle, liposome, micelle or implant of claim 1, wherein the antibody, nanoparticle, particle, liposome or micelle is linked or conjugated to or otherwise displays on its surface a blood brain barrier (BBB)-, central nervous system (CNS)- or brain-penetrating moiety.

8. The pharmaceutical composition, nanoparticle, particle, liposome, micelle or implant of claim 7, wherein the blood brain barrier (BBB)-, central nervous system (CNS)- or brain-penetrating moiety comprises a fragment of an apoB protein.

9. The pharmaceutical composition, nanoparticle, particle, liposome, micelle or implant of claim 1, wherein the antibody is a humanized antibody or a synthetic scFv.

10. The pharmaceutical composition, nanoparticle, particle, liposome, micelle or implant of claim 1, wherein the antibody or scFv comprises an amino acid sequence comprising an amino terminal secretory signaling sequence.

11. The pharmaceutical composition, nanoparticle, particle, liposome, micelle or implant of claim 10, wherein the amino terminal secretory signaling sequence comprises an amino terminal CD5 secretory signaling sequence.

12. The pharmaceutical composition, nanoparticle, particle, liposome, micelle or implant of claim 1, wherein the antibody or scFv comprises the 25 amino acid terminal residues of SEQ ID NO:2.

13. The pharmaceutical composition, nanoparticle, particle, liposome, micelle or implant of claim 1, wherein the antibody or scFv comprises MPMGSLQPLATLYLLGMLVASCLGG (SEQ ID NO: 3).

14. The pharmaceutical composition, nanoparticle, particle, liposome, micelle or implant of claim 1, wherein the antibody or scFv comprises a hinge domain.

15. The pharmaceutical composition, nanoparticle, particle, liposome, micelle or implant of claim 14, wherein the hinge domain comprises AGGGGSGGGGSGGGGSGAP (SEQ ID NO: 5).

16. The pharmaceutical composition, nanoparticle, particle, liposome, micelle or implant of claim 1, wherein the antibody or scFv further comprises a blood brain barrier- (BBB-) transport domain, or an Apo B LDL-receptor binding domain comprising DSSVIDALQYKLEGTTRLTRKRGL KLATALSLSNKFVEGS (SEQ ID NO: 8).

17. The pharmaceutical composition, nanoparticle, particle, liposome, micelle or implant of claim 1, wherein the antibody or scFv comprises an s3RTV5-apoB scFv antibody lacking an amino terminal CD5 secretory signaling sequence or an Apo B LDL-receptor binding domain, or lacking both an amino terminal CD5 secretory signaling sequence and an Apo B LDL-receptor binding domain, and the antibody or the scFv comprises SEQ ID NO: 4, SEQ ID NO: 5 and SEQ ID NO: 6.

18. The pharmaceutical composition, nanoparticle, particle, liposome, micelle or implant of claim 1, wherein the antibody or the scFv comprises an antigen binding site or Complement Determining Regions (CDRs), that bind to an epitope comprising SEQ ID NO: 11.

* * * * *

SEQUENCE LISTING

<160> NUMBER OF SEQ ID NOS: 13

<210> SEQ ID NO 1
<211> LENGTH: 1005
<212> TYPE: DNA
<213> ORGANISM: artificial sequence
<220> FEATURE:
<223> OTHER INFORMATION: synthetic oligonucleotide

<400> SEQUENCE: 1

```
atgcccatgg ggtctctgca accgctggcc accttgtacc tgctggggat gctggtcgct      60
tcctgcctcg gaggcatgga gcaggtcaac ttaagggagt ctggggccga ggtgaagaag     120
cctggggcct cagtaaaggt ctcctgcaag gtttctggat acaccttcac cggctactat     180
atgcactggg tgcgacaggc ccctggacaa ggacttgagt ggatgggatg gatcaactct     240
aacagtggtg ccacaaagta tgcacagaag tttcagggca gggtcaccat gaccagggac     300
acgtccatca ccacagccta catggagttg agcagcctga gatctgacga cacggccgtg     360
tattactgtg cgagaggtgc gagagatggc tacggatttg actactgggg ccagggaacc     420
ctggtcaccg tcttggccgg tggcggtggc agcggcggtg gtgggtccgg tggcggcgga     480
tctggcgcgc catcctatgt gctgactcag ccaccctcag cgtctgggac ccccgggcag     540
agggtcacca tctcttgttc tggaggcagc tccaacatcg gaagtaatgc tgtaagctgg     600
taccagcagc tcccaggaac ggcccccaaa ctcctcatct ttactaatga tcagcggccc     660
tcaggggtcc ctgaccgatt ctctggctcc aagtctggca cctcagcccc cctggccatc     720
agtgggctcc agtcagagga tgagtctgat tattactgtg caacatggga tgacagcctg     780
aatggttggg tgttcggcgg agggaccaag gtcaccgtcg gcccttcga aggtaagcct      840
atccctaacc ctctcctcgg tctcgattct acgcgtaccg tgttgactc atctgtcatt      900
gatgcactgc agtacaaatt agagggcacc acaagattga caagaaaaag gggattgaag     960
ttagccacag ctctgtctct gagcaacaaa tttgtggagg gtagt                    1005
```

<210> SEQ ID NO 2
<211> LENGTH: 335
<212> TYPE: PRT
<213> ORGANISM: artificial sequence
<220> FEATURE:
<223> OTHER INFORMATION: synthetic polypeptide

<400> SEQUENCE: 2

```
Met Pro Met Gly Ser Leu Gln Pro Leu Ala Thr Leu Tyr Leu Leu Gly
  1               5                  10                  15
Met Leu Val Ala Ser Cys Leu Gly Gly Met Glu Gln Val Asn Leu Arg
             20                  25                  30
Glu Ser Gly Ala Glu Val Lys Lys Pro Gly Ala Ser Val Lys Val Ser
         35                  40                  45
Cys Lys Val Ser Gly Tyr Thr Phe Thr Gly Tyr Tyr Met His Trp Val
     50                  55                  60
Arg Gln Ala Pro Gly Gln Gly Leu Glu Trp Met Gly Trp Ile Asn Ser
 65                  70                  75                  80
Asn Ser Gly Ala Thr Lys Tyr Ala Gln Lys Phe Gln Gly Arg Val Thr
                 85                  90                  95
Met Thr Arg Asp Thr Ser Ile Thr Thr Ala Tyr Met Glu Leu Ser Ser
            100                 105                 110
Leu Arg Ser Asp Asp Thr Ala Val Tyr Tyr Cys Ala Arg Gly Ala Arg
        115                 120                 125
Asp Gly Tyr Gly Phe Asp Tyr Trp Gly Gln Gly Thr Leu Val Thr Val
    130                 135                 140
Leu Ala Gly Gly Gly Gly Ser Gly Gly Gly Ser Gly Gly Gly Gly
145                 150                 155                 160
Ser Gly Ala Pro Ser Tyr Val Leu Thr Gln Pro Pro Ser Ala Ser Gly
                165                 170                 175
```

```
Thr Pro Gly Gln Arg Val Thr Ile Ser Cys Ser Gly Ser Ser Asn
            180                 185                 190

Ile Gly Ser Asn Ala Val Ser Trp Tyr Gln Gln Leu Pro Gly Thr Ala
        195                 200                 205

Pro Lys Leu Leu Ile Phe Thr Asn Asp Gln Arg Pro Ser Gly Val Pro
    210                 215                 220

Asp Arg Phe Ser Gly Ser Lys Ser Gly Thr Ser Ala Pro Leu Ala Ile
225                 230                 235                 240

Ser Gly Leu Gln Ser Glu Asp Glu Ser Asp Tyr Tyr Cys Ala Thr Trp
            245                 250                 255

Asp Asp Ser Leu Asn Gly Trp Val Phe Gly Gly Gly Thr Lys Val Thr
        260                 265                 270

Val Gly Pro Phe Glu Gly Lys Pro Ile Pro Asn Pro Leu Leu Gly Leu
    275                 280                 285

Asp Ser Thr Arg Thr Gly Val Asp Ser Ser Val Ile Asp Ala Leu Gln
290                 295                 300

Tyr Lys Leu Glu Gly Thr Thr Arg Leu Thr Arg Lys Arg Gly Leu Lys
305                 310                 315                 320

Leu Ala Thr Ala Leu Ser Leu Ser Asn Lys Phe Val Glu Gly Ser
            325                 330                 335

<210> SEQ ID NO 3
<211> LENGTH: 25
<212> TYPE: PRT
<213> ORGANISM: artificial sequence
<220> FEATURE:
<223> OTHER INFORMATION: MPMGSLQPLATLYLLGMLVASCLGG

<400> SEQUENCE: 3

Met Pro Met Gly Ser Leu Gln Pro Leu Ala Thr Leu Tyr Leu Leu Gly
1               5                   10                  15

Met Leu Val Ala Ser Cys Leu Gly Gly
            20                  25

<210> SEQ ID NO 4
<211> LENGTH: 121
<212> TYPE: PRT
<213> ORGANISM: artificial sequence
<220> FEATURE:
<223> OTHER INFORMATION: synthetic polypeptide

<400> SEQUENCE: 4

Met Glu Gln Val Asn Leu Arg Glu Ser Gly Ala Glu Val Lys Lys Pro
1               5                   10                  15

Gly Ala Ser Val Lys Val Ser Cys Lys Val Ser Gly Tyr Thr Phe Thr
            20                  25                  30

Gly Tyr Tyr Met His Trp Val Arg Gln Ala Pro Gly Gln Gly Leu Glu
        35                  40                  45

Trp Met Gly Trp Ile Asn Ser Asn Ser Gly Ala Thr Lys Tyr Ala Gln
    50                  55                  60

Lys Phe Gln Gly Arg Val Thr Met Thr Arg Asp Thr Ser Ile Thr Thr
65                  70                  75                  80

Ala Tyr Met Glu Leu Ser Ser Leu Arg Ser Asp Asp Thr Ala Val Tyr
            85                  90                  95

Tyr Cys Ala Arg Gly Ala Arg Asp Gly Tyr Gly Phe Asp Tyr Trp Gly
        100                 105                 110

Gln Gly Thr Leu Val Thr Val Leu Ala
    115                 120
```

<210> SEQ ID NO 5
<211> LENGTH: 18
<212> TYPE: PRT
<213> ORGANISM: artificial sequence
<220> FEATURE:
<223> OTHER INFORMATION: synthetic peptide

<400> SEQUENCE: 5

Gly Gly Gly Gly Ser Gly Gly Gly Gly Ser Gly Gly Gly Gly Ser Gly
1               5                   10                  15

Ala Pro

<210> SEQ ID NO 6
<211> LENGTH: 109
<212> TYPE: PRT
<213> ORGANISM: artificial sequence
<220> FEATURE:
<223> OTHER INFORMATION: synthetic polypeptide

<400> SEQUENCE: 6

Ser Tyr Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Ser Asn
            20                  25                  30

Ala Val Ser Trp Tyr Gln Gln Leu Pro Gly Thr Ala Pro Lys Leu Leu
        35                  40                  45

Ile Phe Thr Asn Asp Gln Arg Pro Ser Gly Val Pro Asp Arg Phe Ser
    50                  55                  60

Gly Ser Lys Ser Gly Thr Ser Ala Pro Leu Ala Ile Ser Gly Leu Gln
65                  70                  75                  80

Ser Glu Asp Glu Ser Asp Tyr Tyr Cys Ala Thr Trp Asp Asp Ser Leu
                85                  90                  95

Asn Gly Trp Val Phe Gly Gly Gly Thr Lys Val Thr Val
            100                 105

<210> SEQ ID NO 7
<211> LENGTH: 12
<212> TYPE: PRT
<213> ORGANISM: artificial sequence
<220> FEATURE:
<223> OTHER INFORMATION: synthetic peptide

<400> SEQUENCE: 7

Lys Pro Ile Pro Asn Pro Leu Leu Gly Leu Asp Ser
1               5                   10

<210> SEQ ID NO 8
<211> LENGTH: 40
<212> TYPE: PRT
<213> ORGANISM: artificial sequence
<220> FEATURE:
<223> OTHER INFORMATION: synthetic peptide

<400> SEQUENCE: 8

Asp Ser Ser Val Ile Asp Ala Leu Gln Tyr Lys Leu Glu Gly Thr Thr
1               5                   10                  15

Arg Leu Thr Arg Lys Arg Gly Leu Lys Leu Ala Thr Ala Leu Ser Leu
            20                  25                  30

Ser Asn Lys Phe Val Glu Gly Ser
            35                  40

<210> SEQ ID NO 9
<211> LENGTH: 250
<212> TYPE: PRT
<213> ORGANISM: artificial sequence
<220> FEATURE:
<223> OTHER INFORMATION: synthetic polypeptide

<400> SEQUENCE: 9

```
Met Glu Gln Val Asn Leu Arg Glu Ser Gly Ala Glu Val Lys Lys Pro
1               5                   10                  15

Gly Ala Ser Val Lys Val Ser Cys Lys Val Ser Gly Tyr Thr Phe Thr
            20                  25                  30

Gly Tyr Tyr Met His Trp Val Arg Gln Ala Pro Gly Gln Gly Leu Glu
        35                  40                  45

Trp Met Gly Trp Ile Asn Ser Asn Ser Gly Ala Thr Lys Tyr Ala Gln
    50                  55                  60

Lys Phe Gln Gly Arg Val Thr Met Thr Arg Asp Thr Ser Ile Thr Thr
65                  70                  75                  80

Ala Tyr Met Glu Leu Ser Ser Leu Arg Ser Asp Asp Thr Ala Val Tyr
                85                  90                  95

Tyr Cys Ala Arg Gly Ala Arg Asp Gly Tyr Gly Phe Asp Tyr Trp Gly
            100                 105                 110

Gln Gly Thr Leu Val Thr Val Leu Ala Gly Gly Gly Ser Gly Gly
        115                 120                 125

Gly Gly Ser Gly Gly Gly Gly Ser Gly Ala Pro Ser Tyr Val Leu Thr
    130                 135                 140

Gln Pro Pro Ser Ala Ser Gly Thr Pro Gly Gln Arg Val Thr Ile Ser
145                 150                 155                 160

Cys Ser Gly Gly Ser Ser Asn Ile Gly Ser Asn Ala Val Ser Trp Tyr
                165                 170                 175

Gln Gln Leu Pro Gly Thr Ala Pro Lys Leu Leu Ile Phe Thr Asn Asp
            180                 185                 190

Gln Arg Pro Ser Gly Val Pro Asp Arg Phe Ser Gly Ser Lys Ser Gly
        195                 200                 205

Thr Ser Ala Pro Leu Ala Ile Ser Gly Leu Gln Ser Glu Asp Glu Ser
    210                 215                 220

Asp Tyr Tyr Cys Ala Thr Trp Asp Asp Ser Leu Asn Gly Trp Val Phe
225                 230                 235                 240

Gly Gly Gly Thr Lys Val Thr Val Arg Ser
                245                 250
```

<210> SEQ ID NO 10
<211> LENGTH: 750
<212> TYPE: DNA
<213> ORGANISM: artificial sequence
<220> FEATURE:
<223> OTHER INFORMATION: synthetic nucleotide

<400> SEQUENCE: 10

```
atggagcagg tcaacttaag ggagtctggg gccgaggtga agaagcctgg ggcctcagta    60
aaggtctcct gcaaggtttc tggatacacc ttcaccggct actatatgca ctgggtgcga   120
caggcccctg gacaaggact tgagtggatg ggatggatca actctaacag tggtgccaca   180
aagtatgcac agaagtttca gggcagggtc accatgacca gggacacgtc catcaccaca   240
gcctacatgg agttgagcag cctgagatct gacgacacgg ccgtgtatta ctgtgcgaga   300
ggtgcgagag atggctacgg atttgactac tggggccagg gaaccctggt caccgtcttg   360
```

```
gccggtggcg gtggcagcgg cggtggtggg tccggtggcg gcggatctgg cgcgccatcc    420
tatgtgctga ctcagccacc ctcagcgtct gggaccccccg ggcagagggt caccatctct    480
tgttctggag gcagctccaa catcggaagt aatgctgtaa gctggtacca gcagctccca    540
ggaacggccc ccaaactcct catctttact aatgatcagc ggccctcagg ggtccctgac    600
cgattctctg gctccaagtc tggcacctca gccccctgg ccatcagtgg gctccagtca    660
gaggatgagt ctgattatta ctgtgcaaca tgggatgaca gcctgaatgg ttgggtgttc    720
ggcggaggga ccaaggtcac cgtccgatca                                      750
```

```
<210> SEQ ID NO 11
<211> LENGTH: 23
<212> TYPE: PRT
<213> ORGANISM: artificial sequence
<220> FEATURE:
<223> OTHER INFORMATION: synthetic peptide

<400> SEQUENCE: 11

Asp Ala Gly Leu Lys Ala Glu Glu Ala Gly Ile Gly Asp Thr Pro Ser
1               5                   10                  15

Leu Glu Asp Glu Ala Ala Gly
            20

<210> SEQ ID NO 12
<211> LENGTH: 7
<212> TYPE: PRT
<213> ORGANISM: artificial sequence
<220> FEATURE:
<223> OTHER INFORMATION: synthetic peptide

<400> SEQUENCE: 12

Ala His Arg Glu Arg Met Ser
1               5

<210> SEQ ID NO 13
<211> LENGTH: 6
<212> TYPE: PRT
<213> ORGANISM: artificial sequence
<220> FEATURE:
<223> OTHER INFORMATION: synthetic peptide

<400> SEQUENCE: 13

Ala Arg Glu Arg Met Ser
1               5
```